United States Patent
Rincon et al.

(10) Patent No.: US 10,350,262 B2
(45) Date of Patent: Jul. 16, 2019

(54) MCJ AGONISTS AND USES THEREFOR

(71) Applicant: University of Vermont and State Agricultural College, Burlington, VT (US)

(72) Inventors: Mercedes Rincon, Burlington, VT (US); Thomas Roberts, Denver, CO (US); Tina Thornton, Westford, VT (US)

(73) Assignee: University of Vermont and State Agricultural College, Burlington, VT (US)

(*) Notice: Subject to any disclaimer, the term of this patent is extended or adjusted under 35 U.S.C. 154(b) by 0 days.

(21) Appl. No.: 15/551,995

(22) PCT Filed: Feb. 18, 2016

(86) PCT No.: PCT/US2016/018406
§ 371 (c)(1),
(2) Date: Aug. 18, 2017

(87) PCT Pub. No.: WO2016/134110
PCT Pub. Date: Aug. 25, 2016

(65) Prior Publication Data
US 2018/0028599 A1 Feb. 1, 2018

Related U.S. Application Data

(60) Provisional application No. 62/117,530, filed on Feb. 18, 2015.

(51) Int. Cl.
| | | |
|---|---|---|
| *A61K 38/08* | (2019.01) | |
| *A61K 38/10* | (2006.01) | |
| *A61K 38/17* | (2006.01) | |
| *A61K 47/48* | (2006.01) | |
| *A61K 38/16* | (2006.01) | |
| *C07K 7/06* | (2006.01) | |
| *C07K 7/08* | (2006.01) | |
| *C07K 14/47* | (2006.01) | |
| *A61K 47/64* | (2017.01) | |
| *A61K 38/04* | (2006.01) | |
| *C07K 11/00* | (2006.01) | |
| *A61K 31/704* | (2006.01) | |

(52) U.S. Cl.
CPC .......... *A61K 38/16* (2013.01); *A61K 31/704* (2013.01); *A61K 38/04* (2013.01); *A61K 38/08* (2013.01); *A61K 38/10* (2013.01); *A61K 38/17* (2013.01); *A61K 38/1709* (2013.01); *A61K 47/64* (2017.08); *C07K 7/06* (2013.01); *C07K 7/08* (2013.01); *C07K 11/00* (2013.01); *C07K 14/47* (2013.01); *C07K 14/4703* (2013.01); *C07K 2319/01* (2013.01); *C07K 2319/07* (2013.01); *C07K 2319/10* (2013.01)

(58) Field of Classification Search
CPC ........ A61K 38/08; A61K 38/10; A61K 38/17; A61K 38/1709; A61K 47/64; C07K 7/06; C07K 7/08; C07K 14/00; C07K 14/47; C07K 14/4702; C07K 14/4703; C07K 2319/07
See application file for complete search history.

(56) References Cited

U.S. PATENT DOCUMENTS

| | | |
|---|---|---|
| 5,922,567 A | 7/1999 | Au-Young et al. |
| 6,001,598 A | 12/1999 | Au-Young et al. |
| 6,043,222 A | 3/2000 | Au-Young et al. |
| 6,222,029 B1 | 4/2001 | Edwards et al. |
| 6,916,609 B1 | 7/2005 | Au-Young et al. |
| 8,354,237 B2 | 1/2013 | Rincon et al. |
| 2008/0261217 A1 | 10/2008 | Melnikov et al. |
| 2010/0129931 A1 | 5/2010 | Rincon et al. |
| 2012/0165269 A1* | 6/2012 | Kim .................. C07K 14/4747 514/19.3 |
| 2015/0202257 A1 | 7/2015 | Rincon et al. |
| 2018/0125930 A1 | 5/2018 | Rincon et al. |

FOREIGN PATENT DOCUMENTS

| | | | |
|---|---|---|---|
| WO | 2006068440 A1 | 6/2006 | |
| WO | 2008097467 A1 | 8/2008 | |
| WO | 2014011742 A1 | 1/2014 | |
| WO | WO-2014011742 A1 * | 1/2014 | ............. A61K 38/17 |

OTHER PUBLICATIONS

Witham et al. Transient ectopic expression as a method to detect genes conferring drug resistance. International Journal of Cancer. vol. 122, pp. 2641-2645. (Year: 2008).*
Gottesman, M. et al., "Multidrug Resistance in Cancer: Role of ATP-Dependent Transporters." Nature Reviews Cancer, Jan. 2002, vol. 2, pp. 48-58.Gottesman, M. et al., "Multidrug Resistance in Cancer: Role of ATP-Dependent Transporters." Nature Reviews Cancer, Jan. 2002, vol. 2, pp. 48-58.
Gussow, D. et al., "Humanization of Monoclonal Antibodies." Methods in Enzymology, 1991, vol. 203, pp. 99-121.
Guy, et al., "Induction of Mammary Tumors by Expression of Polyomavirus Middle T Oncogene: A Transgenic Mouse Model for Metastatic Disease." Mol. Cell. Biol. 12, (1992); pp. 954-961.
Halazonetis, T. et al., "c-Jun Dimerizes with Itself and with c-Fos, Forming Complexes of Different DNA Binding Affinities." Cell, Dec. 2, 1988, vol. 55, pp. 917-924.
Hamanaka, RB. and Chan Del, N.S., "Mitochondrial reactive oxygen species regulate cellular signaling and dictate biological outcomes." Trends Biochem Sci, Sep. 2010, vol. 35, pp. 505-513.
Harbottle, A. et al., "Role of Glutathione S-Transferase P1, P-Glycoprotein and Multidrug Resistance-Associated Protein 1 in Acquired Doxorubicin Resistance." Int J Cancer, Jun. 15, 2001, vol. 92, pp. 777-783.

(Continued)

*Primary Examiner* — Jeffrey E. Russel
(74) *Attorney, Agent, or Firm* — Pierce Atwood LLP

(57) ABSTRACT

The invention relates, in part, to compounds, compositions, and methods useful to treat cancer in cells and subjects. In some aspects the invention includes contacting a cancer cell with one or more exogenous methylation-controlled J protein (MCJ) agonist compounds to increase sensitivity of the cancer cell to one or more chemotherapeutic agents. In certain aspects the invention includes compounds and methods useful to kill cancer cells.

19 Claims, 9 Drawing Sheets

Specification includes a Sequence Listing.

(56) References Cited

OTHER PUBLICATIONS

Harker, W. et al., "Multidrug (Pleiotropic) Resistance in Doxorubicin-selected Variants of the Human Sarcoma Cell f-ine MES-SA." Cancer Research, Sep. 1985, vol. 45, pp. 4091-4096.
Hatle, K. et al., "Methylation-controlled J protein promotes c-Jun degradation to prevent ABCB1 transporter expression." Molecular and Cellular Biology, American Society for Microbiology, vol. 27, No. 8, Apr. 1, 2007, pp. 2952-2966.
Hatle, K., et al., "MCJ/DnaJC15, an Endogenous Mitochondrial Repressor of the Respiratory Chain that Controls Metabolic Alterations." Mol. Cell. Biol. 33, (2013); pp. 2302-2314.
Hayashi, M. et al., "A crucial role of mitochondrial Hsp40 in preventing dilated cardiomyopathy." Nat Med, Jan. 2006, vol. 12, pp. 128-132.
Hogquist, K.A. et al., "T cell receptor antagonist peptides induce positive selection." Cell, Jan. 1994, vol. 76, pp. 17-27.
Holm, P. et al., "Functional mapping and single chain construction of the anti-cytokeratin 8 monoclonal antibody TS1." Molecular Immunology, Feb. 2007, vol. 44, pp. 1075-1084.
Horton, et al., "Mitochondria-Penetrating Peptides." (2008) Chemistry & Biology 15: 375-382.
Hosoda, A., et al., "Positive contribution of ERdj5/JPDI to endoplasmic reticulum protein quality control in the salivary," Biochem J, Sep. 2009, vol. 425, pp. 117-125.
Hu, YB and XY Liu, "Protective effects of SP600125 in a diet-induced rat model of non-alcoholic steatohepatitis." Scand J Gastroenlerol., 2009, vol. 44, pp. 1356-1362. (Abstract only, 1 page).
Hunter, P.J. et al., "Mrj encodes a DnaJ-related co-chaperone that is essential for murine placental development." Development, Mar. 1999, vol. 126, pp. 1247-1258.
Huston et al., "Protein engineering of antibody binding sites: Recovery of specific activity in an anti-digoxin single-chain Fv analogue produced in *Escherichia coli*." Proc. Natl. Acad. Sci. USA, 85, (1988); pp. 5879-5883.
Izadi, et al., "Innate immune responses to B. burgdorderi mediated by JNK1 and the cochaperone, methylation controlled DNAJ (MCJ)." Disseration for Doctor of Philosphy, Department of Veterinary & Animcal Sciences, University of Massachusetts,—Amherst, MA USA, 2011, pp. 1-85.
Izawa, I., et al., "Identification of Mrj, a DnaJ/Hsp40 Family Protein, as a Keratin 8/18 Filament Regulatory Protein." Journal of Biological Chemistry, Nov. 3, 2000, Vo. 275, pp. 34521-34527.
Kampinga, H.H. et al., "Guidelines for the nomenclature of the human heat shock proteins." Cell Stress Chaperones, Jan. 2009, vol. 14, pp. 105-111.
Kawakami, K. et al., "Identification and purification of a human immunoglobulin-enhancer-binding protein (NF-KB) hat activates transcription from a human immunodeficiency virus type 1 promoter in vitro." Proc Natl Acad Sci. USA, Jul. 1988, vol. 85, pp. 4700-4704.
Khalil, AA. et al., "Heat shock proteins in oncology: diagnostic biomarkers or therapeutic targets"? Biochimica et Biophysica Acta (BBA)—Reviews on Cancer, Dec. 2011, vol. 1816, pp. 89-104.
Klement, G. et al., "Differences in Therapeutic Indexes of Combination Metronomic Chemotherapy and an Anti-VEGFR-2 Antibody in Multidrug-resistant Human Breast Cancer Xenografts." Clinical Cancer Research, Jan. 2002, vol. 8, pp. 221-232.
Kohler, G., et al., "Derivation of specific antibody-producing tissue culture and tumor lines by cell fusion." Eur J Immunol., Jul. 1976, vol. 6, pp. 511-519.
Koppenol, W.H. et al., "Otto Warburg's contributions to current concepts of cancer metabolism." Nat Rev Cancer, May 2011, vol. 11, pp. 325-337.
Landschulz, W. et al., "The DNA Binding Domain of the Rat Liver Nuclear Protein C/EBP is Bipartite." Science, Mar. 31, 1989, vol. 243, pp. 1681-1688.
Lapuente-Brun, et al., "Supercomplex Assembly Determines Electron Flux in the Mitochondrial Electron Transport Chains." Science vol. 340, (2013); pp. 1567-1570.
Leachman, S. et al., "First-in-human Mutation-targeted siRNA Phase lb Trial of an Inherited Skin Disorder." American Society of Gene & Cell Therapy, Feb. 2010, vol. 18, gs. 442-446.
Lee, D. et al., "Involvement of the Molecular Chaperone Ydj1 in the Ubiquitin-Dependent Degradation of Short-Lived and Abnormal Proteins in *Saccharomyces cerevisiae*." Molecular Cell Biology, Sep. 1996, vol. 16, pp. 4773-4781.
Lee, W. et al., "Purified Transcription Factor AP-1 Interacts with TPA-Inducible Enhancer Elements." Cell, Jun. 19, 1987 , vol. 49, pp. 741-752.
Levine, A.J. and Puzio-Kuter, A.M., "The control of the metabolic switch in cancers by oncogenes and tumor suppressorgenes." Science, Dec. 2010, vol. 330, pp. 1340-1344.
Lindsey, J. et al., "Epigenetic inactivation of MCJ (DNAJD1) in malignant paediatric brain tumors." Int J Cancer, Jan. 15, 2006, vol. 118, pp. 346-352.
Lingzhou et al., "Advances in research on targeting mitochondria for cancer therapy." Anhui Medical and Pharmaceutical, vol. 15, No. 11, 1329-1331, (2011).
Lo et al., "Tid1, a cochaperone of the heat shock 70 protein and the mammalian counterpart of the *Drosophila* tumor suppressor 1(2)tid, is critical for early embryonic development and cell survival." Mol. Cell. Biol. Mar. 2004, vol. 24, pp. 2226-2236.
Longley, D.B. et al., "Molecular mechanisms of drug resistance." Journal of Pathology, Jan. 2005, vol. 205, pp. 275-292.
MacCallum, R. et aL, "Antibody-antigen Interactions: Contact Analysis and Binding Site Topography." Journal of Molecular Biology, Oct. 11, 1996, vol. 262, pp. 732-745.
Maines, T. R et al., "Transmission and pathogenesis of swine-origin 2009 A(H1N1) influenza viruses in ferrets and mice." Science, Jul. 2009, vol. 325, pp. 484-487.
Mariuzza, RA et al., "The Structural Basis of Antigen-Antibody Recognition." Annu. Rev. Biophys., Biophys. Chem., 1987, vol. 16, pp. 139-159.
McKenzie, M. and Ryan, M.T., "Assembly factors of human mitochondrial complex I and their defects in disease." UBMB Life, Jul. 2010, vol. 62, pp. 497-502.
Mechetner, E. et aL, "Levels of Multidrug Resistance (MDR1) P-Glycoprotein Expression by Human Breast Cancer Correlate with in Vitro Resistance to Tazol and Doxorubicin." Clinical Cancer Research, Feb. 1998, vol. 4, pp. 389-398.
Mitra, A et al., "Multi-faceted role of HSP40 in cancer." Clin Exp Metastasis, 2009, vol. 26, pp. 559-567.
Mokranjac, D. et al., "The import motor of the yeast mitochondrial TIM23 preprotein translocase contains two different J proteins, Tim14 and Mdj2." J Biol Chem, Sep. 2005, vol. 280, pp. 31608-31614.
Mokranjac, D. et al., "Tim14, a novel key component of the import motor of the TIM23 protein translocase of mitochondria." EMBO Journal, Oct. 1, 2003, vol. 22, pp. 4945-4956.
Musti, A. et al., "Differential Regulation of c-Jun and Juno by Ubiquitin-Dependent Protein Degradation." Biol Chem., Oct. 1996, vol. 377, pp. 619-624.
Musti, A. et al., "Reduced Ubiquitin-Dependent Degradation of c-Jun After Phosphorylation by MAP Kinases." Science, Jan. 17, 1997, vol. 275, pp. 400-402.
Nabhan, J. et al., "The 19 S Proteasomal Subunit POH1 Contributes to the Regulation of c-Jun Ubiquitination, Stability, and Subcellular Localization." Journal of Biological Chemistry, Jun. 9, 2006, vol. 281, pp. 16099-16107.
Nambudiri et al., "Small Interfering RNA." Journal of Investigative Dermatology (2013) 133: e15 doi: 10.1038/id.2013.411.
Nateri, A. et al., "The Ubiquitin Ligase SCFFbw7 Antagonizes Apoptotic JNK Signaling." Science, Feb. 27, 2004, vol. 303, pp. 1374-1378.
Negro, Francesco, "Mechanisms and significance of liver steatosis in hepatitis C virus infection." World Journal of Gastroenterology, Nov. 14, 2006, vol. 12, pp. 6756-6765.
Noonan, K.E. et al., "Quantitative analysis of MDR1(multidrug resistance) gene expression in human tumors by Dloymerase chain reaction." Proc Natl Acad Sci. USA, Sep. 1990, vol. 87, pp. 7160-7164.

(56) References Cited

OTHER PUBLICATIONS

Ohnishi, T. et al., "Structure-function studies of iron-sulfur clusters and semiquinones in the NADH-Q oxidoreductase segment of the respiratory chain." Biochim Biophys Acta, Jun. 1998, vol. 1365, pp. 301-308.
Orthwein, A. et al., "Optimal functional levels of activation-induced deaminase specifically require the Hsp40 DnaJa1." EMBO J, Feb. 2012, vol. 31, pp. 679-691.
Pedraza-Alva et al., "Activation of p38 MAP kinase byDNA double-strand breaks in V(D)J recombination induces a G2/M cell cycle checkpoint." The EMBO Journal (2006) 25, pp. 763-773, European Molecular Biology Organization.
Phillips, A., "The challenge of gene therapy and DNA delivery." J Pharm Pharmacology, 2001; 53: 1169-1174.
Pirollo et al., "Targeted Delivery of Small Interfering RNA: Approaching Effective Cancer Therapies." Cancer Res. 2008; 68(5): 1247-1250.
Plavinskaya, T. et al., "Effects of acute and chronic low density lipoprotein exposure on neutrophil function." Pulm Pharmacol Ther., Aug. 2013, vol. 26, pp. 405-411.
Quark Pharmaceuticals, "In a Phase 2 Study PF-04523655 (RTP801I-14) Showed Improved Vision over Standard of Care in Patients with Diabetic Macular Edema at 12 Months." Mar. 18, 2011, 4 pgs.
Qui et al., "The diversity of the DnaJ/Hsp40 family, the crucial partners for Hsp70 chaperones." Cellular and Molecular Life Science, 63 (2006) 2560-2570.
Rincon, M. et al., "Interleukin-6, multi-drug resistance protein-1 expression and response to paclitaxel in women with metastatic breast cancer: results of cancer and leukemia group B trial 159806." Breast Cancer Research Treat, Dec. 2006, vol. 100, pp. 301-308.
Rincon, M. et al., "Prostaglandin E2 and the increase of intracellular cAMP inhibit the expression of interleukin 2 receptors in human T cells." Eur J Immunol, Nov. 1988, vol. 18, pp. 1791-1796.
Rudikoff, S. et al., "Single amino acid substitution altering antigen-binding specificity." Proc. Natl. Acad. Sci. USA, Mar. 1982, vol. 79, pp. 1979-1983.
Saibara, T. et al., "Acute hepatic failure with swollen mitochondria and microvesicular fatty degeneration of hepatocytes triggered by free radical initiator." Lab Invest., Apr. 1994, vol. 70, abstract only, 1page.
Salceda, S. et al., "Hypoxia-inducible Factor 1alpha (HIF-1a) Protein Is Rapidly Degraded by the Ubiquitin-Proteasome System under Normoxic Conditions. Its stabilization by hypoxia depends on redox-induced changes." Journal of Biological Chemistry, Sep. 5, 1997, vol. 272, pp. 22642-22647.
Saraswathi, V. et al., "Dietary Fish Oil Exerts Hypolipidemic Effects in Lean and Insulin Sensitizing Effects in Obese LDLR-1-Mice1-3", The Journal of Nutrition, Oct. 2009, pp. 2380-2386.
Saraswathi, V. et al., "Fish Oil Increases Cholesterol Storage in White Adipose Tissue with Concomitant Decrease in Inflammation, Hepatic Steatosis, and Atherosclerosis in Mice 1,2", The Journal of Nutrition, May 2007, pp. 1776-1782.
Scheufler, C. et al., "Structure of TPR Domain-Peptide Complexes: Critical Elements in the Assembly of the Hsp70-Hsp90 Mullichaperone Machine." Cell, Apr. 14, 2000, vol. 101, pp. 199-210.
Schusdziarra et al., "Methylation-controlled J-protein MCJ acts in the import of proteins into human mitochondria." Human Molecular Genetics, vol. 22, No. 7, Apr. 1, 2013, pp. 1348-1357.
Scotto K., "Transcriptional regulation of ABC drug transporters." Oncogene, Oct. 20, 2003, vol. 22, pp. 17496-17511.
Shi et al., "Biodistribution of Small Interfering RNA at the Organ and Cellular Levels after Lipid Nanoparticle-mediated Delivery." Journal of Histochemistry & Cytochemistry 59(8), 727-740, (2011).
Shridhar, V. et al., "Loss of expression of a new member of the DNAJ protein family confers resistance to chemotherapeutic agents used in the treatment of ovarian cancer." Cancer Research, American Association for Cancer Research, vol. 61, No. 10, May 15, 2001, pp. 4258-4265.
Sladowski, D. et al., "An improved MTT assay." Journal of Immunological Methods, Jan. 4, 1993, vol. 157, pp. 203-207.
Sondermann, H. et al., "Structure of a Bag/Hsc70 Complex: Convergent Functional Evolution of Hsp70 Nucleotide Exchange Factors." Science, Feb. 23, 2001, vol. 291, pp. 1553-1557.
Sozio, MS. et al., "The role of lipid metabolism in the pathogenesis of alcoholic and nonalcoholic hepatic steatosis." Semin Liver Dis. Nov. 2010, vol. 30, pp. 378-390. (Abstract only, 1 page).
Sterrenberg, J.N. et al., "Human DNAJ in cancer and stem cells." Cancer Lett, Dec. 2011, vol. 312, pp. 129-142.
Stone, R.M., et al., "Acute Myeloid Leukemia." American Society of Hematology (2004), pp. 98-117.
Strathdee. G. et al., "Demethylation of the MCJ gene in stage III/IV epithelial ovarian cancer and response to thermotherapy." Gynecologic Oncology, Jun. 2005, vol. 97, pp. 893-903.
Strathdee et al., "Cell type-specific methylation of an intronic CpG island controls expression of the MCJ gene." Carcinogenesis May 2004; 25(5), pp. 693-701.
Terada, K. et al., "A type I DnaJ homolog, DjA 1, regulates androgen receptor signaling and spermatogenesis." EMBO J, Feb. 2005, vol. 24, pp. 611-622.
Teratini et al., "A high-cholesterol diet exacerbates liver fibrosis in mice via accumulation of free cholesterol in hepatic stellate cells." Gastroenterology, Jan. 2012, vol. 142, pp. 152-164.
Treier, M. et al., "Ubiquitin-Dependent c-Jun Degradation in Vivo Is Mediated by the 1:i Domain." Cell, Sep. 9, 1994, vol. 78, pp. 787-798.
Ungewickell, E. et al., "Role of auxilin in uncoating clathrin-coated vesicles." Nature, Dec. 7, 1995, vol. 378, pp. 632-635.
Vajdos, F. et al., "Comprehensive Functional Maps of the Antigen-binding Site of an Anti-ErbB2 Antibody Obtained With Shotgun Scanning Mutagenesis." Journal of Molecular Biology, Jul. 5, 2002, vol. 320, pp. 415-428.
Van Der Windt, G.J. et al., "Mitochondrial respiratory capacity is a critical regulator of COB+ T cell memory development." Immunity, Jan. 2012, vol. 36, pp. 68-78.
Vidal et al., "Making sense of antisense." European Journal of Cancer, (2005), 41: 2812-2818.
Wahl, R. et al., "Improved Radioimaging and Tumor Localization with Monoclonal F(ab')2.", Journal of Nuclear Medicine., Apr. 1983, vol. 24, pp. 316-325.
Walsh, P. et al., "The J-protein family: modulating protein assembly, disassembly and translocation." EMBO Rep, Jun. 2004, vol. 5, pp. 567-571.
Wang, et al., "The brown fat-enriched secreted factor Nrg4 preserves metabolic homeostasis through attenuation of hepatic lipogenesis." Nature Medicine, 2014; 20: 1436-1445.
Warburg, J., "On Respiratory Impairment in Cancer Cells." Science, Aug. 10, 1956, vol. 124, pp. 267-272.
Watts, J. and D Corey, "Silencing disease genes in the laboratory and the clinic", Journal of Pathology, 2012, vol. 226, pp. 365-379.
Winkler, K et al., "Changing the Antigen Binding Specificity by Single Point Mutations of an Anti-p24 (HIV-1) antibody." Journal of Immunology, Oct. 15, 2000, vol. 165, pp. 4505-4514.
Wu et al., "Humanization of a Murine Monoclonal Antibody by Simultaneous Optimization of Framework and CDR Residues." J. Mol. Biol. (1999) 294, pp. 151-162.
Affidavit Regarding Deposited Microorganism Pursuant to 37 C.F.R 1.808 filed in U.S. Appl. No. 12/449,265, (signed Sep. 27, 2012).
Ahn, BY et al., "Tid1 is a new regulator of p53 mitochondrial translocation and apoptosis in cancer." Oncogene, Feb. 2010, vol. 29, pp. 1155-1166.
Alakhova, E.Y., et al., "Differential Metabolic Responses to Pluronic in MDR and non-MDR Cells: A Novel Pathway for Chemosensitization of Drug Resistant Cancers." J. Control Release (2010) 142(1): 89-100.
Alley, M. et al., "Feasibility of Drug Screening with Panels of Human Tumor Cell Lines Using a Micoculture Wetrazolium Assay", Cancer Research, Feb. 1, 1988, vol. 48, pp. 589-601.
Alverez-Calderon, et al., "Tyrosine Kinase Inhibition in Leukemia Induces an Altered Metabolic State Senstive to Mitochondrial Perurbations." Clin. Cancer Res. 21(6), (2015); pp. 1360-1372.
Angel, P. et al., "Phorbol Ester-Inducible Genes Contain a Common Cis Element Recognized by a TPA-Modulated Wrans-Acting Factor." Cell, Jun. 19, 1987, vol. 49, pp. 729-739.

(56) References Cited

OTHER PUBLICATIONS

Araki, K. et al., "mTOR regulates memory CD8 T cell differentiation." Nature, Jul. 2009, vol. 460, pp. 108-112.
Auphan, N. et al., "Consequences of intrathymic TCR engagement by partial agonist on selection events and peripheral T cell activation program." J Immunol, May 1998, vol. 160, pp. 4810-4821.
Baerga-Ortiz et al., "Epitope mapping of a monoclonal antibody against human thrombin by H/D-exchange mass specgtromBIRD et al., "Single-Chain Antigen-Binding Proteins." Science 242, (1988); pp. 423-426etry reveals selection of a diverse sequence in a highly conserved protein." Protein Science 11, (2002), pp. 1300-1308.
Bird, R., et al, "Single-Chain Antigen-Binding Proteins." Science, Oct. 21, 1988, vol. 242, pp. 423-426.
Brummelkamp, T. et al., "A System for Stable Expression of Short Interfering RNAs in Mammalian Cells." Science, Apr. 19, 2002, vol. 296, pp. 550-553.
Ehrlich, M. et al., "Hypomethylation and hypermethylation of DNA in Wilms tumors", Oncogene, Sep. 26, 2002, vol. 21, pp. 6694-6702.
Fairchild, C. et al., "Isolation of Amplified and Overexpressed DNA Sequences from Adriamycin-resistant Human Breast Cancer Cells". Cancer Research, Oct. 1, 1987, vol. 47, pp. 5141-5148.
Fairchild, C. et al., "Multidrug Resistance in Cells Transfected with Human Genes Encoding a Variant Pglycoprotein and Glutathione S-Transferase-n." Molecular Pharmacology, Jun. 1990, vol. 37, pp. 801-809.
Fang, D. et al., "Ubiquitin-mediated fluorescence complementation reveals that Jun ubiquitinated by Itch/AIP4 is ocalized to lysosomes." Proc Natl Acad Csi US A, Oct. 12, 2004, Vo1. 101, pp. 14782-14787.
Finlay, D and Cantrell, DA., "Metabolism, migration and memory in cytotoxic T cells." Nat Rev Immunol, Feb. 2011, vol. 11, pp. 109-117.
Fuchs, S. et al., "Phosphorylation-dependent targeting of c-Jun ubiquitination by Jun N-kinase." Oncogene, Oct. 8, 1996, vol. 13, pp. 1531-1535.
Garcia-Ruiz, C. et al., "Metabolic therapy: lessons from liver diseases." Curr Pharm Des., Dec. 2011, vol. 17, pp. 3933-3944. (Abstract only, 1 page).
Genbank Submission; NIH/NCBI, Accession No. AAD38506; Shridhar et al.; May 25, 2001, 2 pages.
Genbank Submissoin; NIH/NCBI, Accession No. AF126743; Shridhar et al., May 25, 2001, 2 pages.
Genbank Submission; NIH/NCBI, Accession No. NP _037370; Hendrickson et al.; Jul. 29, 2011, 2 pages.
George, J. et al., "Differential Effects of Anti-B2-Glycoprotein I Antibodies on Endothelial Cells and on the Manifestations of Experimental Antiphospholipid Syndrome." American Heart Association, 1998, vol. 97, pp. 900-906.
Gao, et al., "Jun Turnover is Controlled Through JNK-Dependent Phosphorylation of the E3 Ligase Itch." Oct. 8, 2004, vol. 306, 271-5.
Witham, J. et al., "Transient ectopic expression as a method to detect genes conferring drug resistance." International Journal of Cancer, vol. 122, No. 11, Jan. 1, 2008, pp. 2641-2645.
Yang, ZX, et al., "Effects of nuclear receptor FXR on the regulation of liver lipid metabolism in patients with non-alcoholic fatty liver disease." Hepatol Int, 2010, vol. 4, pp. 741-748.
Yin et al., "Silencing heat shock factor 1 by small interfering RNA abrogates heat shock-induced cardioprotection against ischemia-reperfusion injury in mice." Journal of Molecular and Cellular Cardiology, 2005; 39: 681-689.
Young, J. et al., "More than folding: localized functions of cytosolic chaperones." Trends in Biochemical Science, Oct. 2003, vol. 28, pp. 541-547.
Zhang, J. et al., "Osthole improves alcohol-induced fatty liver in mice by reduction of hepatic oxidative stress." Phytother Res., May 2011, vol. 25, pp. 638-643. (Abstract only, 1 page).

Zhu, F. et al., "COOH-terminal Src Kinase-Medicated c-Jun Phosphorylation Promotes c-Jun Degradation and Inhibits Cell Transformation." Cancer Research, Jun. 1, 2006, vol. 66, pp. 5729-5736.
Non-Final Office Action for U.S. Appl. No. 12/449,265 dated Jan. 5, 2012, 46 pages.
Response to Office Action dated Jan. 5, 2012 for U.S. Appl. No. 12/449,265, filed Apr. 18, 2012, 22 pages.
International Preliminary Report on Patentability and the Written Opinion from the International Searching Authority dated Aug. 4, 2009 from corresponding PCT/US2008/001357, 10 pages.
International Preliminary Report on Patentability and the Written Opinion from the International Searching Authority dated Jan. 13, 2015 from corresponding PCT/US2013/049885, 7 pages.
International Search Report dated Jan. 16, 2014 from corresponding PCT/US2013/049885, 6 pages.
International Preliminary Report on Patentability and the Written Opinion from the International Searching Authority dated Aug. 22, 2017 from corresponding PCT/US2016/018406, 8 pages.
International Search Report dated Aug. 25, 2016 from corresponding PCT/US2016/018406, 6 pages.
Vermont EPSCoR Annual State Meeting, "Adaptation to Climate Change in the Lake Champlain Basin: New Understanding through Complex Systems Modeling (RAAC)." Aug. 5, 2014, Hilton Burlington Hotel, Burlington, Vermont, 4 pages.
Acin-Perez, R., et al., "Respiratory Active Mitochondrial Supercomplexes." Mol. Cell. 32, (2008); pp. 529-539.
Addya, S. et al., "Targeting of NH2-terminal-processed Microsomal Protein to Mitochondria: A Novel Pathway for the Biogenesis of Hepatic Mitochondrial P450MT2." The Journal of Cell Biology, Nov. 3, 1997, vol. 139, pp. 589-599.
Cairns, R.A. et al., "Regulation of cancer cell metabolism." Nat Rev Cancer, Feb. 2011, vol. 11, pp. 85-95.
Caldas, C. et al., "Humanization of the anti-CD18 antibody 6. 7: an unexpected effect of framework residue in binding to antigen." Molecular Immunology, May 2003, vol. 39, pp. 941-952.
Campbell, A., Monoclonal Antibody Technology, Laboratory Techniques in Biochemistry and Molecular Biology, 1984, Elsevier Science Publishers BV.: Amsterdam, The Netherlands vol. 13, pp. 1-32, Chapter 1: General Properties and Applications of Monoclonal Antibodies.
Casset, F. et al., "A peptide mimetic of an anti-CD4 monoclonal antibody by rational design." Biochemical and Biophysical Research Communication, Jul. 18, 2003, vol. 307, pp. 198-205.
Chen, Y. et al., "Characterization of Adriamycin-resistant Human Breast Cancer Cells Which Display Overexpression of a Novel Resistance-related Membrane Protein." Journal of Biological Chemistry, Jun. 15, 1990, vol. 265, pp. 10073-10080.
Chen, Y. et al., "In Situ Biochemical Demonstration that P-Glycoprotein Is a Drug Efflux Pump with Broad Specificity." Journal of Cellular Biology, Mar. 6, 2000, vol. 148, pp. 863-870.
Chien, N. et al., "Significant structural and functional change of an antigen-binding site by a distant amino acid Substitution: Proposal of a structural mechanism." Pree. Natl. Acad. Sci., USA, Jul. 1989, vol. 86, pp. 5532-5536.
Clason, T. et al., "The structure of eukaryotic and prokaryotic complex I." J Struct Biol, Jan. 2010, vol. 169, pp. 81-88.
Comerford , K.et al., "Hypoxia-inducible Factor-1-dependent Regulation of the Multidrug Resistance (MDR1) Gene." Cancer Research, Jun. 15, 2002, vol. 62, pp. 3387-3394.
Conze et al., "Autocrine p\Production of Interleukin 6 Causes Multidrug Resistance in Breast Cancer Cells." Cancer Research, Dec. 15, 2001, vol. 61, pp. 8851-8858.
Conze, D. et al., "c-Jun NH(2)-terminal kinase (JNK)1 and JNK2 have distinct roles in COB(+) T cell activation." J Exp Med, Apr. 2002, vol. 195, pp. 811-823.
Craig, EA et al., "The diverse roles of J-proteins, the obligate Hsp70 co-chaperone." Rev Physiol Biochem Pharmacol., 2006, vol. 156, pp. 1-21.
Czauderna et al., "Structural variations and stabilizing modifications of synthetic siRNAs in mammalian cells." Nucleic Acids Research, 2003 vol. 31, No. 11, 2705-2716.

(56) References Cited

OTHER PUBLICATIONS

Da Cruz, S. et al., "Proteomic analysis of the mouse liver mitochondrial inner membrane." J. Biol. Chem., Oct. 2003, vol. 278, pp. 41566-41571.
De Pascalis, R et al., "Grafting of "Abbreviated" Complementary-Determining Regions Containing Specificity-Determining Residues Essential for Ligand Contact to Engineer a Less immunogenic Humanized Monoclonal Antibody." Journal of Immunology, 2002, vol. 169, pp. 3076-3084.
Del Gaizo, V. et al., "Targeting proteins to mitochondria using TAT." Molecular Genetics and Metabolism, 2003, vol. 80, pp. 170-180.
Derijard, B. et al., "JNK1: A Protein Kinase Stimulated by UV Light and Ha-Ras That Binds and Phosphorylates the c-Jun Activation Domain." Cell., Mar. 25, 1994, vol. 76, pp. 1025-1037.
Devincenzo et al., "A randomized, double-blind, placebo-controlled study of an RNAi-based therapy directed against respiratory syncytial virus." PNAS, May 11, 2010, vol. 107, pp. 8800-8805.
Diah, S. et al., "Resistance to Mitoxantrone in Multidrug-resistant MCF7 Breast Cancer Cells: Evaluation of Mitoxantrone Transport and the Role of Multidrug Resistance Protein Family Proteins." Cancer Research, Jul. 15, 2001, vol. 61, pp. 5461-5467.
Diekert, K. et al., "An internal targeting signal directing proteins into the mitochondrial intermembrane space." PNAS Oct. 12, 1999, vol. 96, pp. 11752-11757.
Doyle, L et al., "Multidrug resistance mediated by the breast cancer resistance protein BCRP (ABCG2)." Oncogene, Oct. 20, 2003, vol. 22, pp. 7340-7358.
Dykxhoorn, D.M. et al., "The silent treatment: siRNAs as small molecule drugs." Gene Therapy, 2006, vol. 13, pp. 541-552.
Genbank Submission; NIH/NCBI, Accession No. AAD38506; Shridhar et al.; May 25, 2001, 1 page.
Genbank Submissoin; NIH/NCBI, Accession No. AF126743; Shridhar et al., May 25, 2001, 1 page.
George, J. et al., "Differential Effects of Anti-B2-Glycoprotein I Antibodies on Endothelial Cells and on the Manifestations of Experimental Antiphospholipid Syndrome." American Heart Association, 1997, vol. 97, pp. 900-906.
Giusti, A. et al., "Somatic diversification of S107 from an antiphosphocholine to an anti-DNA autoantibody is due to a single base change in its heavy chain variable region." Proc. Natl. Acad. Sci. USA, May 1987, vol. 84, pp. 2926-2930.

* cited by examiner

Figure 15A
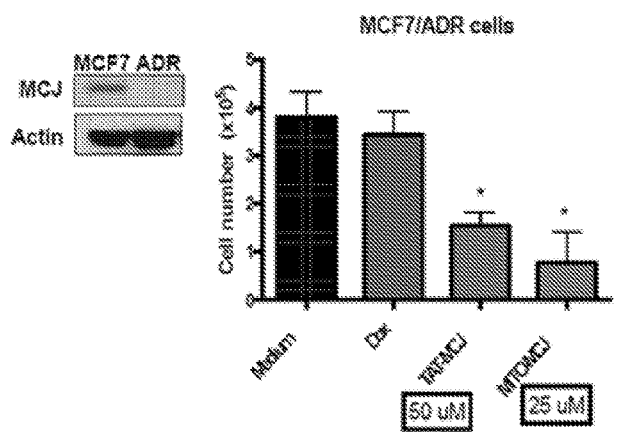
Figure 15B
Figure 15C
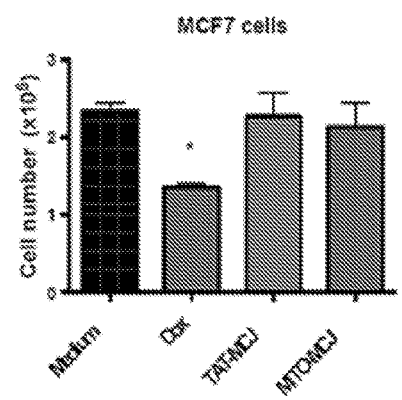
Figure 16A
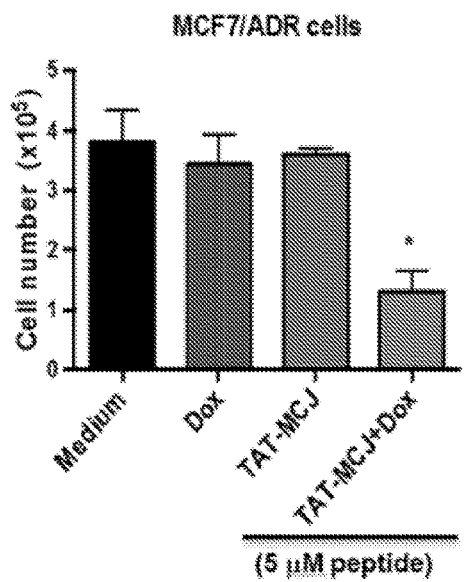
Figure 16B
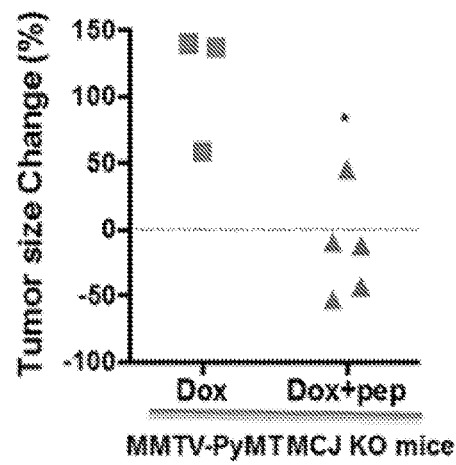

MCJ AGONISTS AND USES THEREFOR

RELATED APPLICATIONS

This application is a National Stage Filing under U.S.C. § 371 of PCT International Application PCT/US16/18406, filed Feb. 18, 2016 which was published under PCT Article 21(2) in English, which claims benefit under 35 U.S.C. § 119(e) of U.S. Provisional Application No. 62/117,530, filed Feb. 18, 2015 and the content of each is incorporated by reference herein in its entirety.

GOVERNMENT INTEREST

This invention was made with government support under grant numbers AI094027 and CA127099 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Feb. 25, 2019, is named W7134834.txt and is 19.5 KB in size.

FIELD OF THE INVENTION

The invention relates, in part, to methods and compounds to increase sensitivity of cancer cells to chemotherapeutic agents, to reduce resistance of cancer cells to chemotherapeutic agents, and to increase cancer cell death.

BACKGROUND OF THE INVENTION

Treatment for various cancers may include administration of chemotherapeutic agents to kill fast-dividing cells in a subject with the cancer. A problem arises in chemotherapy when cancer cells develop resistance to one or more chemotherapeutic agents, making the cancer refractory to the treatment. Resistance to the therapeutic agents reduces the efficacy of chemotherapies and increases the instance of treatment failure. Cancer treatment is complicated by the relatively few compounds or agents that kill cancer cells and can be safely administered to cancer patients. Also, the development of resistance to chemotherapeutic agents reduces the availability of cancer treatment options.

SUMMARY OF THE INVENTION

According to one aspect of the invention, methods increasing a chemo-sensitivity of a cancer cell are provided. The methods include, contacting a cancer cell with one or more exogenous MCJ agonist compounds in an amount effective to increase sensitivity of the cancer cell to one or more chemotherapeutic agents. In some embodiments, the exogenous MCJ agonist compound comprises an MCJ molecule. In some embodiments, the MCJ molecule is an MCJ polypeptide or a polynucleotide that encodes an MCJ polypeptide. In certain embodiments, contacting the cancer cell includes administering the exogenous MCJ agonist compound in a pharmaceutical composition in a manner to contact the cancer cell with the MCJ agonist compound. In some embodiments, the pharmaceutical composition also includes a pharmaceutically acceptable carrier. In some embodiments, the exogenous MCJ agonist compound includes one or more targeting agents. In some embodiments, the one or more targeting agents include a cell penetrating peptide, a cell internalization agent, an HIV-derived TAT sequence, a small molecule, a polynucleotide, a liposome, mitochondrial-targeting agent, a synthetic polypeptide, a PEGylated liposome, an aquasome, a biodegradable polymer, a nanoparticle, an oligonucleotide, or a polypeptide. In some embodiments, the cell internalization agent includes a TAT polypeptide sequence, and optionally includes a TAT polypeptide sequence set forth as YGKKRRQRRG (SEQ ID NO: 9), or a variant thereof. In certain embodiments, the exogenous MCJ agonist compound includes one or more mitochondrial targeting agents. In some embodiments, the one or more mitochondrial targeting agent include mitochondria-targeting peptide; a nanoparticle that traffics to mitochondria, or a liposome-based delivery systems for mitochondria. In some embodiments, the one or more mitochondrial-targeting agent is a polypeptide, and optionally the polypeptide includes the amino acid sequence set forth as GTRTWVPKGLKSP (SEQ ID NO: 10), or a variant thereof. In some embodiments, the mitochondrial-targeting peptide comprises the amino acid sequence set forth as $F_xRF_xKF_xRF_xK$ (SEQ ID NO:37), or a variant thereof. In some embodiments, the MCJ polypeptide includes a sequence set forth as MAARGVIAPVGESLRY-AEYLQPSAKRPDADVDQQRLVRSL (SEQ ID NO: 1), MAARGVIAPVGESLRYAEYL (SEQ ID NO: 2), VIAPVGESL (SEQ ID NO: 3), or VGESLRYAEY (SEQ ID NO: 4), MAARGVIAPVGESLRYAEYLQPSAK*RPDA DVDQQRLVRSL (SEQ ID NO: 5), or a variant thereof. In certain embodiments, the variant of SEQ ID NO: 1, 2, 3, 4, or 5 has at least 75%, 80%, 85%, 90%, 95%, 97%, 98%, 99%, or 100% sequence identity to the amino acid sequence of SEQ ID NO: 1, 2, 3, 4, or 5, respectively. In some embodiments, the variant of the MCJ polypeptide comprises a fragment of the MCJ polypeptide amino acid sequence set forth as SEQ ID NO: 1, 2, 3, 4, or 5. In some embodiments, the MCJ polypeptide variant includes a fragment of the amino acid sequence of the MCJ polypeptide and the fragment has at least 75%, 80%, 85%, 90%, 95%, 97%, 98%, 99%, or 100% sequence identity to the region of the amino acid sequence of the MCJ polypeptide with which it aligns. In certain embodiments, the exogenous MCJ agonist compound includes a polypeptide having an amino acid sequence set forth as: YGKKRRQRRGMAARGVI-APVGESLRYAEYLGTRTWVPKGLKSP (SEQ ID NO: 6), YGKKRRQRRGVIAPVGESLGTRTWVPKGLKSP (SEQ ID NO: 7), YGKKRRQRRGVGESLRYAEYGTRTWVPK-GLKSP (SEQ ID NO: 8), or a variant thereof. In some embodiments, the cancer cell is a vertebrate cancer cell, and optionally is a mammalian cancer cell. In some embodiments, the cancer cell is a dermal cell, a breast tissue cell, a muscle cell, a circulatory cell, a connective tissue cell, a bone cell, an exocrine cell, an endocrine cell, an organ cell, a mesenchyme cell, a connective tissue cell, an epithelial cell, an endothelial cell, a neuronal cell, a glial cell, a glandular cell, a stromal cell, a renal cell, a thyroid cell, a stem cell, a hematopoietic cell, a lymphoid cell, a myeloid cell, an erythroid cell, a cardiomyocyte, an hepatocyte, an astrocyte, an oligodendrocyte, or an adipocyte. In some embodiments, the cancer of the cancer cell is a carcinoma, a sarcoma, a leukemia, a lymphoma, a myeloma, a glioma, breast cancer, ovarian cancer, epithelial cancer, uterine cancer, vaginal cancer, prostate cancer, testicular cancer, penile cancer, colon cancer, rectal cancer, cervical cancer, throat cancer, oral cancer, pancreatic cancer, kidney cancer, liver cancer, lung cancer, melanoma, basal cell carcinoma, squamous cell carcinoma, head and neck cancer, stomach cancer, bone cancer, connective tissue cancer, bladder cancer, ocular cancer, nasal cancer, adipose cancer, thyroid cancer, non-Hodgkin lymphoma, small intestine cancer, Wilms tumor, gastrointestinal cancer, CNS cancer, PNS cancer, esophageal cancer, Karposi sarcoma, gallbladder cancer, mesothelioma, Hodgkin lymphoma, multiple myeloma, osteoscarcoma, neuroblastoma, rhabdomyoscarcoma, sinus cancer, retinoblastoma, and salivary cancer. In certain embodiments, the cancer cell is in a subject. In some embodiments, the method also includes contacting the cancer cell with one or more chemotherapeutic agents. In some embodiments, the chemotherapeutic agent is a taxane, an anthracycline, a cytotoxin, a platinum-based drug, an antimetabolite, a base analog, a nucleoside analogue, a nucleotide analogue, an antifolate, methotrexate, an alkaloid, vincristine, vinblastine, irinotecan, etoposide, velcade, a tyrosine kinase inhibitor, a serine/threonine kinase inhibitor, bleomycin, cyclophosphamide, cytoxan, everolimus, or metformin. In certain embodiments, the exogenous MCJ agonist compound reduces mitochondrial ATP production in the cancer cell. In some embodiments, the exogenous MCJ agonist compound decreases a level of ABC-transporters in the cancer cell. In some embodiments, the cancer cell does not include an endogenous MCJ molecule. In some embodiments, the cancer cell includes an endogenous MCJ molecule. In certain embodiments, the cancer cell is one of a plurality of cancer cells. In some embodiments, the plurality of cancer cells includes one or more cancer cells that include an endogenous MCJ molecule. In some embodiments, the plurality of cancer cells includes one or more cancer cells that do not include an endogenous MCJ molecule. In certain embodiments, the plurality of cancer cells includes one or more cancer cells that do not include an endogenous MCJ molecule and one or more cancer cells that include an endogenous MCJ molecule. In certain embodiments, the MCJ polypeptide includes one or more acetylated amino acid residues. In some embodiments, the acetylated amino acid residue is a lysine (K) residue, and optionally corresponds to the K25 position in the sequence set forth as SEQ ID NO: 1 when the amino acid sequence of the MCJ polypeptide is aligned with amino acid sequence set forth as SEQ ID NO: 1.

According to another aspect of the invention, methods of treating a cancer in one or more cells are provided. The methods include contacting one or more cancer cells with an effective amount of at least one exogenous MCJ agonist compound to treat the cancer in the one or more cancer cells. In some embodiments, the exogenous MCJ agonist compound includes an MCJ molecule. In certain embodiments, the MCJ molecule is an MCJ polypeptide or a polynucleotide that encodes an MCJ polypeptide. In certain embodiments, contacting the one or more cancer cells includes administering the exogenous MCJ agonist compound in a pharmaceutical composition in a manner to contact the one or more cancer cells with the exogenous MCJ agonist compound. In some embodiments, the pharmaceutical composition further includes a pharmaceutically acceptable carrier. In some embodiments, the exogenous MCJ agonist compound includes one or more targeting agents. In some embodiments, the one or more targeting agents include a cell penetrating peptide, mitochondrial-targeting agent, a synthetic polypeptide, a cell internalization agent, an HIV-derived TAT sequence, a small molecule, a polynucleotide, a liposome, a PEGylated liposome, an aquasome, a biodegradable polymer, a nanoparticle, an oligonucleotide, or a polypeptide. In certain embodiments, the cell internalization agent includes a TAT polypeptide sequence, and optionally includes a TAT polypeptide sequence set forth as YGKKRRQRRG (SEQ ID NO: 9) or a variant thereof. In some embodiments, the exogenous MCJ agonist compound includes one or more mitochondrial targeting agents. In some embodiments, the one or more mitochondrial targeting agent includes a mitochondria-targeting peptide; a nanoparticle that traffics to mitochondria, or a liposome-based delivery systems for mitochondria. In some embodiments, the one or more mitochondrial-targeting agent is a polypeptide, and optionally the polypeptide includes the amino acid sequence set forth as GTRTWVPKGLKSP (SEQ ID NO: 10), or a variant thereof. In some embodiments, the mitochondrial-targeting peptide comprises the amino acid sequence set forth as $F_xRF_xKF_xRF_xK$ (SEQ ID NO:37), or a variant thereof. In certain embodiments, the MCJ polypeptide includes a sequence set forth as MAARGVIAPVGESLRYAEYLQPSAKRPDADVDQQRLVRSL (SEQ ID NO: 1), MAARGVIAPVGESLRYAEYL (SEQ ID NO: 2), VIAPVGESL (SEQ ID NO: 3), or VGESLRYAEY (SEQ ID NO: 4), MAARGVIAPVGESLRYAEYLQPSAK*RPDADVDQQRLVRSL (SEQ ID NO: 5), or a variant thereof. In some embodiments, the variant of SEQ ID NO: 1, 2, 3, 4, or 5 has at least 75%, 80%, 85%, 90%, 95%, 97%, 98%, 99%, or 100% sequence identity to the amino acid sequence of SEQ ID NO: 1, 2, 3, 4, or 5, respectively. In some embodiments, the variant of the MCJ polypeptide includes a fragment of the MCJ polypeptide amino acid sequence set forth as SEQ ID NO: 1, 2, 3, 4, or 5. In some embodiments, the MCJ polypeptide variant includes a fragment of the amino acid sequence of the MCJ polypeptide and the fragment has at least 75%, 80%, 85%, 90%, 95%, 97%, 98%, 99%, or 100% sequence identity to the region of the amino acid sequence of the MCJ polypeptide with which it aligns. In certain embodiments, the exogenous MCJ agonist compound includes a polypeptide having an amino acid sequence set forth as: YGKKRRQRRGMAARGVIAPVGESLRYAEYLGTRTWVPKGLKSP (SEQ ID NO: 6), YGKKRRQRRGVIAPVGESLGTRTWVPKGLKSP (SEQ ID NO: 7), YGKKRRQRRGVGESLRYAEYGTRTWVPKGLKSP (SEQ ID NO: 8), or a variant thereof. In some embodiments, the one or more cancer cells is a vertebrate cancer cell, and optionally is a mammalian cancer cell. In some embodiments, the one or more cancer cells is a dermal cell, a breast tissue cell, a muscle cell, a circulatory cell, a connective tissue cell, a bone cell, an exocrine cell, an endocrine cell, an organ cell, a mesenchyme cell, a connective tissue cell, an epithelial cell, an endothelial cell, a neuronal cell, a glial cell, a glandular cell, a stromal cell, a renal cell, a thyroid cell, a stem cell, a hematopoietic cell, a lymphoid cell, a myeloid cell, an erythroid cell, a cardiomyocyte, an hepatocyte, an astrocyte, an oligodendrocyte, or an adipocyte. In certain embodiments, the cancer of the one or more cancer cells is a carcinoma, a sarcoma, a leukemia, a lymphoma, a myeloma, a glioma, breast cancer, ovarian cancer, epithelial cancer, uterine cancer, vaginal cancer, prostate cancer, testicular cancer, penile cancer, colon cancer, rectal cancer, cervical cancer, throat cancer, oral cancer, pancreatic cancer, kidney cancer, liver cancer, lung cancer, melanoma, basal cell carcinoma, squamous cell carcinoma, head and neck cancer, stomach cancer, bone cancer, connective tissue cancer, bladder cancer, ocular cancer, nasal cancer, adipose cancer, thyroid cancer, non-Hodgkin lymphoma, small intestine cancer, Wilms tumor, gastrointestinal cancer, CNS cancer, PNS cancer, esophageal cancer, Karposi sarcoma, gallbladder cancer, mesothelioma, Hodgkin lymphoma, multiple myeloma, osteoscarcoma, neuroblastoma, rhabdomyoscarcoma, sinus cancer, retinoblastoma, and salivary cancer. In some embodiments, the one or more cancer cells do not include an endogenous MCJ molecule. In some embodiments, the one or more cancer cells include an endogenous MCJ molecule. In some embodiments, the one or more cancer cells is in a subject. In certain embodiments, the exogenous MCJ agonist compound reduces mitochondrial ATP production in the one or more cancer cells. In some embodiments, the exogenous MCJ agonist compound decreases the level of ABC-transporters in the one or more cancer cells. In some embodiments, the method also includes contacting the one or more cancer cells with an effective amount of one or more chemotherapeutic agents. In some embodiments, the one or more chemotherapeutic agent is agent is a taxane, a cytotoxic agent, an anthracycline, a platinum-based drug, an anti-metabolite, a base analog, a nucleoside analogue, a nucleotide analogue, an antifolate, methotrexate, an alkaloid, vincristine, vinblastine, irinotecan, etoposide, velcade, a tyrosine kinase inhibitor, a serine/threonine kinase inhibitor, bleomycin, cyclophosphamide, cytoxan, everolimus, or metformin. In certain embodiments, the one or more cancer cell is one or more of a plurality of cancer cells. In some embodiments, the plurality of cancer cells includes one or more cancer cells that do not include an endogenous MCJ molecule. In some embodiments, the plurality of cancer cells includes one or more cancer cells comprising an endogenous MCJ molecule. In certain embodiments, the plurality of cancer cells includes one or more cancer cells that do not include an endogenous MCJ molecule and one or more cancer cells that include an endogenous MCJ molecule. In some embodiments, the MCJ polypeptide includes one or more acetylated amino acid residues. In some embodiments, the acetylated amino acid residue is a lysine (K) residue, and optionally corresponds to the K25 position in the sequence set forth as SEQ ID NO: 1 when the amino acid sequence of the MCJ polypeptide is aligned with amino acid sequence set forth as SEQ ID NO: 1.

According to yet another aspect of the invention, methods of assessing an effect of an exogenous MCJ agonist compound on a chemotherapeutic agent's efficacy in a treating cancer are provided. The methods include (a) contacting a test cancer cell with a chemotherapeutic agent; (b) further contacting the test cancer cell with an exogenous MCJ agonist compound; (c) determining the efficacy of the chemotherapeutic agent in treating the cancer in the further contacted test cancer cell; and (d) comparing the determined efficacy of the chemotherapeutic agent on the test cancer cell to an efficacy of chemotherapeutic agent in treating the cancer in a control cancer cell not contacted with the exogenous MCJ agonist compound; wherein a different efficacy of the chemotherapeutic agent in treating the cancer in the test cancer cell compared with the efficacy of the chemotherapeutic agent in treating the cancer in the control cancer cell indicates an effect of the exogenous MCJ agonist compound on the efficacy of the chemotherapeutic agent in treating the cancer. In some embodiments, the exogenous MCJ agonist compound includes an MCJ molecule. In certain embodiments, the MCJ molecule is an MCJ polypeptide or a polynucleotide that encodes an MCJ polypeptide. In some embodiments, the exogenous MCJ agonist compound includes one or more targeting agents. In some embodiments, the one or more targeting agents include a mitochondrial-targeting agent, a cell penetrating peptide, a cell internalization agent, a synthetic polypeptide, an HIV-derived TAT sequence, a small molecule, a polynucleotide, a liposome, a PEGylated liposome, an aquasome, a biodegradable polymer, a nanoparticle, an oligonucleotide, or a polypeptide. In certain embodiments, the cell internalization agent includes a TAT polypeptide sequence, and optionally includes a TAT polypeptide sequence set forth as YGKKRRQRRG (SEQ ID NO: 9), or a variant thereof. In some embodiments, the exogenous MCJ agonist compound includes one or more mitochondrial targeting agents. In some embodiments, the one or more mitochondrial targeting agent includes mitochondria-targeting peptide; a nanoparticle that traffics to mitochondria, or a liposome-based delivery systems for mitochondria. In certain embodiments, the one or more mitochondrial-targeting agent is a polypeptide, and optionally the polypeptide includes the amino acid sequence set forth as GTRTWVPKGLKSP (SEQ ID NO: 10), or a variant thereof. In some embodiments, the mitochondrial-targeting peptide comprises the amino acid sequence set forth as $F_xRF_xKF_xRF_xK$ (SEQ ID NO: 39), or a variant thereof. In some embodiments, the exogenous MCJ agonist compound reduces mitochondrial ATP production in the contacted cell. In some embodiments, the exogenous MCJ agonist compound decreases the level of ABC-transporters in the contacted cell. In certain embodiments, the MCJ polypeptide includes a sequence set forth as MAARGVIAPVGESLRYAEYLQPSAKRPDADVDQQR-LVRSL (SEQ ID NO: 1), MAARGVIAPVGESLRYAEYL (SEQ ID NO: 2), VIAPVGESL (SEQ ID NO: 3), or VGESLRYAEY (SEQ ID NO: 4), MAARGVI APVGESLRYAEYLQPSAK*RPDADVDQQRLVRSL (SEQ ID NO: 5), or a variant thereof. In some embodiments, the variant of SEQ ID NO: 1, 2, 3, 4, or 5 has at least 75%, 80%, 85%, 90%, 95%, 97%, 98%, 99%, or 100% sequence identity to the amino acid sequence of SEQ ID NO: 1, 2, 3, 4, or 5, respectively. In some embodiments, the variant of the MCJ polypeptide includes a fragment of the MCJ polypeptide amino acid sequence set forth herein as SEQ ID NO: 1, 2, 3, 4, or 5. In some embodiments, the MCJ polypeptide variant includes a fragment of the amino acid sequence of the MCJ polypeptide and the fragment has at least 75%, 80%, 85%, 90%, 95%, 97%, 98%, 99%, or 100% sequence identity to the region of the amino acid sequence of the MCJ polypeptide with which it aligns. In certain embodiments, the exogenous MCJ agonist compound includes a polypeptide having an amino acid sequence set forth as: YGK-KRRQRRGMAARGVIAPVGESLRYAEYLGTRTWVPK-GLKSP (SEQ ID NO: 6), YGKKRRQRR GVIAPVGESLGTRTWVPKGLKSP (SEQ ID NO: 7), YGKKRRQRRGVGESLRYAEYGTRTWVPKGLKSP (SEQ ID NO: 8), or a variant thereof. In some embodiments, the cancer cell is a vertebrate cancer cell, and optionally is a mammalian cancer cell. In some embodiments, the cancer cell is a dermal cell, a breast tissue cell, a muscle cell, a circulatory cell, a connective tissue cell, a bone cell, an exocrine cell, an endocrine cell, an organ cell, a mesenchyme cell, a connective tissue cell, an epithelial cell, an endothelial cell, a neuronal cell, a glial cell, a glandular cell, a stromal cell, a renal cell, a thyroid cell, a stem cell, a hematopoietic cell, a lymphoid cell, a myeloid cell, an erythroid cell, a cardiomyocyte, an hepatocyte, an astrocyte, an oligodendrocyte, or an adipocyte. In certain embodiments, the cancer of the cancer cell is a carcinoma, a sarcoma, a leukemia, a lymphoma, a myeloma, a glioma, breast cancer, ovarian cancer, epithelial cancer, uterine cancer, vaginal cancer, prostate cancer, testicular cancer, penile cancer, colon cancer, rectal cancer, cervical cancer, throat cancer, oral cancer, pancreatic cancer, kidney cancer, liver cancer, lung cancer, melanoma, basal cell carcinoma, squamous cell carcinoma, head and neck cancer, stomach cancer, bone cancer, connective tissue cancer, bladder cancer, ocular cancer, nasal cancer, adipose cancer, thyroid cancer, non-Hodgkin lymphoma, small intestine cancer, Wilms tumor, gastrointestinal cancer, CNS cancer, PNS cancer, esophageal cancer, Karposi sarcoma, gallbladder cancer, mesothelioma, Hodgkin lymphoma, multiple myeloma, osteosarcoma, neuroblastoma, rhabdomyoscarcoma, sinus cancer, retinoblastoma, and salivary cancer. In some embodiments, the exogenous MCJ agonist compound reduces mitochondrial ATP production in the contacted test cancer cell. In some embodiments, the exogenous MCJ agonist compound decreases the level of ABC-transporters in the contacted test cancer cell. In some embodiments, the chemotherapeutic agent is a taxane, an anthracyclines, a platinum-based drug, an anti-metabolite, a base analog, a nucleoside analogue, a nucleotide analogue, an antifolate, methotrexate, an alkaloid, vincristine, vinblastine, irinotecan, etoposide, velcade, a tyrosine kinase inhibitor, a serine/threonine kinase inhibitor, bleomycin, cyclophosphamide, cytoxan, everolimus, or metformin. In certain embodiments, the test cancer cell does not comprise an endogenous MCJ molecule. In some embodiments, the test cancer cell includes an endogenous MCJ molecule. In some embodiments, if the test cancer cell does not include an endogenous MCJ molecule the control cell does not include the endogenous MCJ molecule and if the test cancer cell does include an endogenous MCJ molecule, the control cell includes an endogenous MCJ molecule. In certain embodiments, the MCJ polypeptide includes one or more acetylated amino acid residues. In some embodiments, the acetylated amino acid residue is a lysine (K) residue, and optionally corresponds to the K25 position in the sequence set forth as SEQ ID NO: 1 when the amino acid sequence of the MCJ polypeptide is aligned with the amino acid sequence set forth as SEQ ID NO: 1.

According to another aspect of the invention, compositions are provided. The compositions include one or more MCJ agonist compounds that include one or more MCJ molecules, one or more targeting agents, and optionally, one or more cell internalization agents. In some embodiments, the MCJ molecule is an MCJ polypeptide. In certain embodiments, the exogenous MCJ agonist compound includes one or more targeting agents. In some embodiments, the one or more targeting agents include a cell penetrating peptide, a synthetic polypeptide, a cell internalization agent, an HIV-derived TAT sequence, a small molecule, a polynucleotide, a liposome, a PEGylated liposome, an aquasome, a biodegradable polymer, a nanoparticle, an oligonucleotide, or a polypeptide. In some embodiments, the cell internalization agent includes a TAT polypeptide sequence, and optionally includes a TAT polypeptide sequence set forth as YGKKRRQRRG (SEQ ID NO: 9), or a variant thereof. In certain embodiments, the exogenous MCJ agonist compound includes one or more mitochondrial targeting agents. In some embodiments, the one or more mitochondrial targeting agent includes mitochondria-targeting peptide; a nanoparticle that traffics to mitochondria, or a liposome-based delivery systems for mitochondria. In some embodiments, the one or more mitochondrial-targeting agent is a polypeptide, and optionally the polypeptide includes the amino acid sequence set forth as GTRTWVP-KGLKSP (SEQ ID NO: 10), or a variant thereof. In some embodiments, the mitochondrial-targeting peptide comprises the amino acid sequence set forth as $F_xRF_xKF_xRF_xK$ (SEQ ID NO:37), or a variant thereof. In certain embodiments, the MCJ polypeptide includes a sequence set forth as MAARGVIAPVGESLRYAEYLQPSAKRPDADVDQQR-LVRSL (SEQ ID NO: 1), MAARGVIAPVGESLRYAEYL (SEQ ID NO: 2), VIAPVGESL (SEQ ID NO: 3), or VGESLRYAEY (SEQ ID NO: 4), MAARGVIAPVGESLRYAEYLQPSAK*RPDADVDQQ RLVRSL (SEQ ID NO: 5), or a variant thereof. In some embodiments, the variant of SEQ ID NO: 1, 2, 3, 4, or 5 has at least 75%, 80%, 85%, 90%, 95%, 97%, 98%, 99%, or 100% sequence identity to the amino acid sequence of SEQ ID NO: 1, 2, 3, 4, or 5, respectively. In some embodiments, the variant of the MCJ polypeptide includes a fragment of the MCJ polypeptide amino acid sequence set forth herein as SEQ ID NO: 1, 2, 3, 4, or 5. In some embodiments, the MCJ polypeptide variant includes a fragment of the amino acid sequence of the MCJ polypeptide and the fragment has at least 75%, 80%, 85%, 90%, 95%, 97%, 98%, 99%, or 100% sequence identity to the region of the amino acid sequence of the MCJ polypeptide with which it aligns. In certain embodiments, the MCJ polypeptide includes one or more acetylated amino acid residues. In some embodiments, the acetylated amino acid residue is a lysine (K) residue, and optionally corresponds to the K25 position in the sequence set forth as SEQ ID NO: 1 when the amino acid sequence of the MCJ polypeptide is aligned with the amino acid sequence set forth as SEQ ID NO: 1.

According to yet another aspect of the invention, pharmaceutical compositions are provided. The pharmaceutical compositions include any embodiment of the aforementioned compositions of the invention, and optionally also includes a pharmaceutically acceptable carrier.

According to another aspect of the invention, methods of killing a cancer cell are provided. The methods include contacting a cancer cell with any embodiment of the aforementioned compositions of the invention, in an amount effective to kill the cancer cell. In some embodiments, the cancer cell does not include an endogenous MCJ molecule. In some embodiments, the cancer cell includes an endogenous MCJ molecule. In certain embodiments, the cancer cell is in a subject. In some embodiments, the subject is a mammal, and optionally is a human.

Brief Description of the Sequences

SEQ ID NO: 1 is a 40 amino acid, N-terminal MCJ polypeptide:
MAARGVIAPVGESLRYAEYLQPSAKRPDADVDQQRLVRSL.

SEQ ID NO: 2 is a 20 amino acid, N-terminal MCJ polypeptide:
MAARGVIAPVGESLRYAEYL.

SEQ ID NO: 3 is a 9 amino acid MCJ polypeptide: VIAPVGESL.

SEQ ID NO: 4 is a 10 amino acid MCJ polypeptide: VGESLRYAEY.

SEQ ID NO: 5 is the 40 amino acid polypeptide of SEQ ID NO: 1 with an acetylated lysine at position 25: MAARGVIAPVGESLRYAEYLQPSAK*RPDADVDQQRLVRSL.
(Note K* is acetylated amino acid residue)

-continued

Brief Description of the Sequences

SEQ ID NO: 6 is an MCJ agonist compound that has the amino acid sequence set forth as
SEQ ID NO: 2, a TAT amino acid sequence, and a mitochondrial delivery amino acid
sequence, it is also referred to herein as a TAT-N-MCJ-MTS polypeptide:
YGKKRRQRRGMAARGVIAPVGESLRYAEYLGTRTWVPKGLKSP.

SEQ ID NO: 7 is an MCJ agonist compound that has the amino acid sequence set forth as
SEQ ID NO: 3, a TAT amino acid sequence, and a mitochondrial delivery amino acid
sequence: YGKKRRQRRGVIAPVGESLGTRTWVPKGLKSP.

SEQ ID NO: 8 is an MCJ agonist compound that has the amino acid sequence set forth as
SEQ ID NO: 4, a TAT amino acid sequence, and a mitochondrial delivery amino acid
sequence: YGKKRRQRRGVGESLRYAEYGTRTWVPKGLKSP.

SEQ ID NO: 9 is an amino acid sequence of a TAT targeting polypeptide to which a "G"
spacer amino acid has been added in the final amino acid position: YGKKRRQRRG.

SEQ ID NO: 10 is an amino acid sequence of a mitochondrial delivery polypeptide to which
a "G" spacer has been added in the first amino acid position: GTRTWVPKGLKSP.

SEQ ID NO: 11 is amino acid sequence of human DNAJ domain-containing protein MCJ set
forth as GENBANK ® Accession No. AAD38506.1.
MAARGVIAPVGESLRYAEYLQPSAKRPDADVDQQGLVRSLIAVGLGVAALAFAGRY
AFRIWKPLEQVITETAKKISTPSFSSYYKGGFEQKMSRREAGLILGVSPSAGKAKIRTA
HRRVMILNHPDKGGSPYVAAKINEAKDLLETTTKH.

SEQ ID NO: 12 is mRNA sequence of human DNAJ domain-containing protein MCJ set
forth as GENBANK ® Accession No. AF126743.1
ggtcaggaaagctcaggcaagcccaccctcaggcattacagctagactccgagcttactgggcagtcatctgattcgaccaacatcag
ttcgcagggcttaagcccagtcccttacggcggctggggagggaccaggcccaagtatataaagctccctgagggtccgcgttggct
ttgcgcctgtgagtgtgattcaagaacgtcccagtgcccttggctcctttcggagtgtgaccccgtgcttgcacgggacacgttacccag
ctcgggtgagaagggtatcttccgggaacctcgcctttaatagcacaacgagcgcagagtccactggatctgcgagaagaaaccgcg
ctaactagtttgtccctacggccgcctcgtagtcactgccgcggcgccttgagtctccgggccgcttgccatggctgccgtggtgtc
atcgctccagttggcgagagtttgcgctacgctgagtacttgcagccctcggccaaaccggccagacgccgacgtcgaccagcaggg
actggtaagaagtttgatagctgtaggactgggtgttgcagctcttgcatttgcaggtcgctacgcatttcggatctggaaacctctagaa
caagttatcacagaaactgcaaagaagatttcaactcctagcttttcatcctactataaaggaggatttgaacagaaaatgagtaggcga
gaagctggtcttattttaggtgtaagcccatctgctggcaaggctaagattagaacagctcataggagagtcatgattttgaatcacccag
ataaaggtggatctccttacgtagcagccaaaataaatgaagcaaaagacttgctagaaacaaccaccaaacattgatgcttaaggacc
acactgaaggaaaaaaaagaggggacttcgaaaaaaaaaaagccctgcaaaatattctaaaacatggtatataattttctatatgg
attgaccacagtcttatcttccaccattaagctgtataacaataaaatgttaatagtcttgcttttattatcttttaaagatctccttaaattct.

SEQ ID NO: 13 is amino acid sequence of a mouse DNAJ domain-containing protein.
MATGGGVTSRESLRYAEYLPPSAQRSDADIDHTAGRRLIAVGLGVAAVAFAGRYAF
QIWKPLEQVITATARKISSPSFSSYYKGGFEQKMSKREASLILGVSPSAGKAKIRTAHK
RIMILNHPDKGGSPYVASKINEAKDLLEASSKAN.

SEQ ID NO: 14 is amino acid sequence of a human DnaJ (Hsp40) homolog of subfamily C
set forth as GENBANK ® Accession No. AAH95400.1
MAARGVIAPV GESLRYAEYL QPSAKRPDAD VDQQRLVRSL IAVGLGVAAL
AFAGRYAFRI WKPLEQVITE TAKKISTPSF SSYYKGGFEQ KMSRREAGLI
LGVSPSAGKA KIRTAHRRVM ILNHPDKGGS PYVAAKINEA KDLLETTTKH.

SEQ ID NO: 15 is nucleotide sequence of human DnaJ (HSP40) homolog of subfamily C set
forth as GENBANK ® AccessionNo. BC095400.1
agtctccgggccgccttgccatggctgcccgtggtgtcatcgctccagttggcgagagtttgcgctacgctgagtacttgcagccctcg
gccaaacggccagacgccgacgtcgaccagcagagactggtaagaagtttgatagctgtaggcctgggtgttgcagctcttgcatttg
caggtcgctacgcatttcggatctggaaacctctagaacaagttatcacagaaactgcaaagaagatttcaactcctagatttcatccta
ctataaaggaggatttgaacagaaatgagtaggcgagaagctggtggtcttatttttaggtgtaagcccatctgctggcaaggctaagattag
aacagctcataggagagtcatgattttgaatcacccagataaaggtggatctccttacgtagcagccaaaataaatgaagcaaaagact
tgctagaaacaaccaccaaacattgatgcttaaggaccacactgaaggaaaaaaaagaggggacttcaaaaaaaaaaaaaagcc
ctgcaaaatattctaaaacatggtcttcttaattttctatatggattgaccacagtcttatcttccaccattaagctgtataacaataaaatgtta
atagtatgattttattatcttttaaagatctccttaaattctctaaactgatcttttttcttattttgtttgtgacattcatacattttaagattttttgttat
gttctgaattccccctacacacacacacacacacacacacacgtgcaaaaaatatgatcaagaatgcaattgggatttgtgagc
aatgagtagacctatattgtttatatttgtaccctcattgtcaatttttttttagggaatttgggactctgcctatataaggtgttttaaatgtcttg
agaacaagcactggctgatacctcttggagatatgatctgaaatgtaatggaatttattaaatggtgtttagtaaagtaggggttaaggact
tgttaaagaaccccactatctctgagaccctataggccaaagcatgaggacttggagagctactaaaatgattcaggtttacaaaatgagc
cctgtgaggaaaggttgagagaagtctgaggagtttgtatttaattatagtatccagtactgtatattcattcattctacaaatattt
attgaccccttttgatgtgcaaggcactatcgtgcgtcccctgagagttgcaagtatgaagcagtcatggatcatgaaccaaaggaactt
atatgtagaggaaggataaatcacaaatagtgaatactgttagatacagatgatatattttaaaagttcaaaggaagaaaagaatgtgtta
aacactgcatgagaggaggaataagtggcatagagctaggctttagaaaagaaaaatattccgataccatatgattggtgaggtaagtg
ttattctgagatgagaattagcagaaatagatatatcaatcggagtgattagagtgcagggtttctggaaagcaaggtttggacagagtg
gtcatcaaaggccagccctgtgacttacactgcattaaattaatttatagaacatagtccctgatcattatcacttttactattccaaaggtga
gagaacagattcagatagagtgccagcattgtttcccagtattccttttacaaatcttgggttcattccaggtaaactgaactactgcattgttt
ctatcttaaaatacttttttagatatcctagatgcatctttcaacttctaacattctgtagtttaggagttctcaaccttggcattattgacatgttag
gccaaataatttttttgtggggagggtctcttgtgcgttttagatgattagcaataatccctgacctgttatctactaaagactagtcgtttctcat
cagttgtgacaacaaaatggttccagatattgccaaatgccattagaggacagtaatcgcccccagttgagaaccatttcagtaaaac
tttaattactatttttctttggtttataaaataatgatcctgaattaaattgatggaaccttgaagtcgataaaatatatttcttgctttaaagtcc

Brief Description of the Sequences

```
ccatacgtgtcctactaattttctcatgctttagtgttttcacttttctcctgttatccttgtacctaagaatgccatcccaatcccagatgtcca
cctgcccaaagtctaggcatagctgaaggccaagctaaaatgtatccctcttttctggtacatgcagcaaaagtaatatgaattatcagc
tttctgagagcaggcattgtatctgtatgtttggtgttacattggcacccaataaatatttgttgagcgaaaaaaaaaaaaaaa.
```

SEQ ID NO: 16 is a 21 amino acid, N-terminal MCJ polypeptide that includes a "C" residue at its C terminal: MAARGVIAPVGESLRYAEYLC.

SEQ ID NO: 17 is a 38 amino acid MCJ polypeptide
MAARGVIAPVGESLRYAEYLQPSAKRPDADVDQQRLVR.

SEQ ID NO: 18 is the amino acid sequence of a TAT-N-MCJ polypeptide
YGKKRRQRRGMAARGVIAPVGESLRYAEYL.

SEQ ID NO: 19 MAARGVIAPVGESLRYAEYLQPSAKRPDA.

SEQ ID NO: 20 MAARGVIAPVGESLRYAEYLQPSA.

SEQ ID NO: 21 MAARGVIAPVGESLRYAE.

SEQ ID NO: 22 RGVIAPVGESLRYAEYLC.

SEQ ID NO: 23 AARGVIAPVGESLRYAEYL.

SEQ ID NO: 24 MAARGVIAPVGESLRYAEYLQPSAKRPDADV.

SEQ ID NO: 25 MAARGVIAPVGESLRYAEYLQPSAKRPDADVDQQGLVRS.

SEQ ID NO: 26 MAARGVIAPVGESLRYAEYLQPSAKRPDADVDQQGL.

SEQ ID NO: 27 MAARGVIAPVGESLRYAEYLQPSAKRPDADVD.

SEQ ID NO: 28 MAARGVIAPVGESLRYAEYLQPSAK.

SEQ ID NO: 29 MAARGVIAPVGESLRYAEYLQPSAKRPDAD.

SEQ ID NO: 30 MAARGVIAPVGESLRYAEYLQP.

SEQ ID NO: 31 MAARGVIAPVGESLRYAEYLQPSAKR.

SEQ ID NO: 32 GVIAPVGESLRYAEYL.

SEQ ID NO: 33 ARGVIAPVGESLRYAEYL.

SEQ ID NO: 34 VIAPVGESLRYAEYL.

SEQ ID NO: 35 MAARGVIAPVGES.

SEQ ID NO: 36 is an amino acid sequence of a TAT targeting polypeptide YGKKRRQRR.

SEQ ID NO: 37 is an amino acid sequence of a mitochondrial delivery polypeptide TRTWVPKGLKSP.

SEQ ID NO: 38 is the amino acid sequence of MITO-N-MCJ. In the sequence "$F_x$" is cyclohexylalanine: $F_xRF_xKF_xRF_xK$MAARGVIAPVGESLRYAEYL.

SEQ ID NO: 39 is the cyclohexylalanine-containing sequence: $F_xRF_xKF_xRF_xK$.

BRIEF DESCRIPTION OF THE DRAWINGS

FIG. 9 illustrates that administering to a mouse that has a tumor comprising cancer cells lacking endogenous MCJ polypeptide, an MCJ agonist compound and a chemotherapeutic agent resulted in a greater reduction in tumor size than administering the chemotherapeutic agent to a similar mouse that is not administered the MCJ agonist compound.

FIG. 10 illustrates that of the three treatments the most successful at reducing tumor size was treatment with the doxorubicin in combination with the MCJ agonist compound [dox/pep].

FIG. 11A includes all patients regardless of therapy received (n=1,660). FIG. 11B includes all patients known to be treated with chemotherapy (n=104). FIG. 11C includes all patients known to have received endocrine therapy (n=185). FIG. 11D includes only triple negative (TN) patients known to have received chemotherapy (n=53). Hazard ratio (HR) and logrank p value are shown.

FIG. 12A shows results of Oxygen Consumption Rate (OCR) analysis determined using the MitoStress assay in human breast cancer MCF7 cells and in MCF7/siMCJ cells. FIG. 12B shows results when mammary tumors were harvested from wildtype MMTV (WT) and MCJ KO MMTV (MCJ KO) mice, tumor cells were isolated and used for OCR analysis as described for FIG. 12A.

FIG. 14A-B shows results when MCF7/ADR cells were plated on the Seahorse culture plate overnight. Cells pretreated with medium alone (medium), TAT-N-MCJ-mts peptide (TAT peptide) (50 µM) (FIG. 14A) or MITO-N-MCJ peptide (Mito peptide) (25 µM) (FIG. 14B) for the last 9 h prior to the MitoStress assay as described elsewhere herein. Standard flow chart for the treatments as recommended by the manufacturer (Seahorse Bioscience, Billerica, Mass.) was used: oligomycin (O), FCCP (F) and rotenone and antimycin (R+A). FIG. 14C shows result when MCF7/ADR cells were plated on the Seahorse culture plate for 24 h and directly assayed for OCR using the MitoStress assay. Oligomycin was replaced by vehicle (buffer) or MITO-N-MCJ peptide.

FIG. 15A-C provides a blot and graphs demonstrating that treatment with agonist polypeptides can overcome chemoresistance in breast cancer cells. FIG. 15A provides results of Western blot analysis for MCJ in MCF7 cells and MCF7/ADR (ADR) cells. Actin was used as loading control. FIG. 15B shows results when MCR7/ADR cells ($8 \times 10^4$) were plated and after 18-20 h were treated with medium alone, doxorubicin (Dox) (3 µM), TAT-N-MCJ-mts peptide (50 µM) or MITO-N-MCJ peptide (25 µM). Viable cells were counted 2 days later. FIG. 15C shows results when MCF7 cells ($8 \times 10^4$) were plated, treated, harvested and counted as described for FIG. 15B.

FIG. 16A-B provides graphs showing response to MCJ agonists. FIG. 16A shows results when MCR7/ADR cells ($8 \times 10^4$) were plated and after 18-20 h, were treated with medium alone, doxorubicin (Dox) (3 µM), TAT-N-MCJ-mts peptide (5 µM) or the combination of both. Cells were harvested 2 days later and viable cells were counted. FIG. 16B shows results when MCJ KO MMTV mice (n=3) were treated with doxorubicin alone (Dox) (2 mg/Kg) by i.p. administration, or in combination with the TAT-N-MCJ-mts peptide administered s.c. (10 mg/Kg) at day 0, day 2 and day 3. Mice were harvested at day 4. The size of a tumor over time was determined by caliper measurements, and is represented as a percentage relative to the initial size prior to the treatment. p<0.05 as determined by a paired t-test.

FIG. 17A-B show results when Molm13 cells ($10^4$ cells) were incubated in the presence of medium, TAT-N-MCJ-mts peptide (TAT) (25 µM), MITO-N-MCJ peptide (25 µM), AC220 (2 nM) or the combination of the peptides with AC220. Numbers of viable cells was measured after 3 days. FIG. 17B shows isolated results for AC220 treated cells from in FIG. 17A. FIG. 17C shows results from Molm13 cells what were treated as in FIG. 17A (except that TAT was used at 50 µM) and after 22 hr cells were labeled with TMRE and examined by flow cytometry. The percentage of live cells negative for TMRE (TMREneg) is shown. FIG. 17D shows results from Molm13 cells that were treated as in FIG. 17C and after 22 h cells were labeled with mito-PY1 and examined by flow cytometry. The percentage of live PY1$^+$ cells is shown.

DETAILED DESCRIPTION

Figure 1:
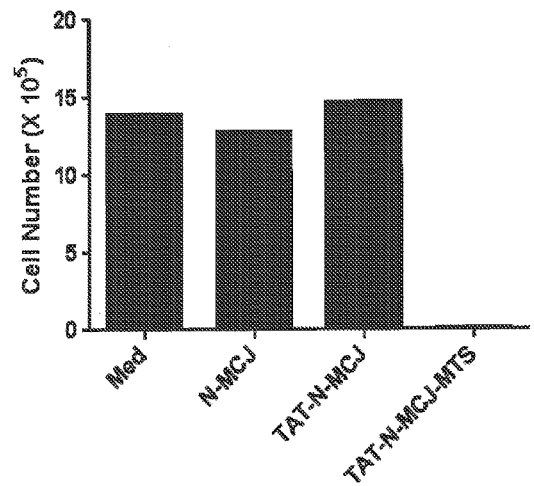
FIG. 1 shows a graph illustrating results from MCF7/ADR cells that were incubated (using standard procedures) for three days in media alone (Med) or in media plus a concentration of 50 μM of an MCJ polypeptide (N-MCJ, SEQ ID NO: 2); a TAT-N-MCJ polypeptide (TAT-N-MCJ, SEQ ID NO: 18); or a TAT-N-MCJ-MTS polypeptide (TAT-N-MCJ-MTS, SEQ ID NO:6). Significantly more cell death occurred in the cell set that was incubated with the TAT-N-MCJ-MTS polypeptide than under the other incubation conditions.

Due to the complex and varied nature of cancers it has remained difficult to understand the diverse physiological mechanisms that may play a role in the development of cancer and/or its treatment. Possible physiological effects of MCJ polypeptides in cancer cells have previously been examined and positive correlations between increased levels of MCJ polypeptides in cancer cells and increased tumor growth have been reported, suggesting not only that treatments to increase MCJ levels in cancer cells would be ineffective to treat the cancer, but that the MCJ increase would likely increase tumor growth. It has now been identified that, surprisingly, administration of an MCJ agonist compound and a chemotherapeutic agent to one or more cancer cells increases cancer cell death and treats the cancer. In certain aspects of the invention, administration of an MCJ agonist compound and a chemotherapeutic agent to a cancer cell and/or a subject with cancer may result in a synergistic treatment effect in which more cancer cell death results from the treatment than occurs when the chemotherapeutic agent is administered to the cancer cell in the absence of the administered MCJ agonist compound. It has also now been identified that, unexpectedly, administration of an MCJ agonist compound to a cancer cell may result in death of the cancer cell. Thus, certain aspects of the invention include contacting one or more cancer cells with one or more MCJ agonist compounds to treat cancer in a cell, tissue, or subject.

It has now been discovered that methods and compounds that include certain MCJ agonist compounds may be used to treat cancer and/or to increase cancer cell sensitivity to chemotherapeutic agents. Methylation-Controlled J protein (MCJ) is a small protein of 150 amino acids and is a unique member of the DnaJC family. MCJ contains a J-domain located at the C-terminus, as opposed to the common N-terminal position, and MCJ's N-terminal region has no homology with other known proteins. In addition, MCJ also contains a transmembrane domain although most DnaJ proteins are soluble. The amino acid sequence of human DNAJ domain-containing protein MCJ of GENBANK® Accession No. AAD38506.1 is set forth herein as SEQ ID NO:11. SEQ ID NO:12 is mRNA sequence of human DNAJ domain-containing protein MCJ set forth as GENBANK® Accession No. AF126743.1. GENBANK® Accession No. AAH95400.1 is an amino acid sequence of a human DnaJ (Hsp40) homolog of subfamily C, provided herein as SEQ ID NO:14. SEQ ID NO:15 is nucleotide sequence of human DnaJ (HSP40) homolog of subfamily C set forth as GENBANK® Accession No. BC095400.1.

The invention, in part, pertains to methods and MCJ agonist compounds that are useful to treat cancer in cells, tissues, and subjects. In certain aspects of the invention an MCJ agonist compound includes an MCJ molecule that is an MCJ polypeptide or a polynucleotide that encodes an MCJ polypeptide; optionally includes one or more targeting agents; and optionally includes one or more mitochondrial targeting agents. In certain embodiments of the invention treatment with an exogenous MCJ agonist compound may comprise contacting one or more cancer cells with one or more MCJ molecules, wherein the contacting increases chemotherapeutic-sensitivity in the cell and decreases the cell's resistance to chemotherapeutic agents. In certain embodiments of the invention, a treatment with an exogenous MCJ agonist compound may include contacting one or more cancer cells with one or more exogenous MCJ molecules, wherein the contact results in the death of one or more of the contacted cancer cells.

The term "exogenous" as used herein in reference to an MCJ agonist compound or an MCJ molecule means a compound or molecule that is administered to a cancer cell. Thus, for example, an MCJ polypeptide administered to a cell is an exogenous MCJ molecule even if the same MCJ molecule is naturally present in a cell. As used herein, an MCJ molecule that is present in a cell due to natural expression in the cell is referred to as an endogenous MCJ molecule. Thus, in certain aspects of the invention, contacting a cancer cell with an exogenous MCJ agonist compound and/or administering an exogenous MCJ agonist compound to a cell or subject, means that the cell was contacted contact with an exogenous MCJ molecule and/or the cell or subject was administered an exogenous MCJ molecule.

In certain aspects of an invention, an MCJ molecule may be administered to a cancer cell to treat the cancer. An MCJ molecule (polypeptide or encoding polynucleotide) that is administered to a cancer cell may be referred to herein as an exogenous MCJ molecule. A naturally expressed MCJ molecule that is present in a cell due to natural expression in that cell, and not due to administration of an exogenous MCJ molecule, is referred to herein as an "endogenous" MCJ molecule. An MCJ molecule, a non-limiting example of which is set forth herein as SEQ ID NO:1, may be administered to a cancer cell either alone or as part of a compound of the invention, and thus be an exogenous MCJ molecule. It will be understood that an MCJ molecule, a non-limiting example of which is the sequence set forth as SEQ ID NO:1, that is present in a cell because of its natural expression in the cell may be referred to herein as an "endogenous" MCJ molecule. Thus, an MCJ molecule may be an exogenous MCJ molecule or an endogenous MCJ molecule, depending on whether the MCJ molecule was administered to a cell, for example using a compound, composition, and/or method of the invention; or the MCJ molecule is expressed in a cell and is not present in the cell as a result of a treatment or compound of the invention.

Molecules, compounds, compositions, and methods of the invention may be used to treat a subject having, or at risk of having a cancer. Thus, methods and compounds of the invention are useful to treat cancers in cells and in subjects. The invention in part, also relates to increasing a sensitivity of a cancer cell to contact with one or more chemotherapeutic agents and reducing resistance of a cancer cell to contact with chemotherapeutic agents. Although not intended to be limiting, in certain aspects of the invention, contacting a cancer cell with an exogenous MCJ agonist compound may decrease a level of ABC-transporters in the cancer cell and in some aspects of the invention, contacting a cancer cell with an exogenous MCJ agonist compound may decrease mitochondrial ATP production in the cancer cell. An increase in sensitivity of a cancer cell to a chemotherapeutic agent may result from contacting the cancer cell with an MCJ agonist compound that in an amount effective to decrease mitochondrial ATP production in the cancer cell and/or to decrease a level of ABC-transporters in the cancer cell, which may assist in maintaining the presence of one or more chemotherapeutic agents in the cancer cell, which may result in increased efficacy in killing the cancer cell by the chemotherapeutic agent. Increasing sensitivity of a cancer cell to one or more chemotherapeutic agent, either increasing from no sensitivity (a level of zero) to a higher level of sensitivity, or increasing from an existing level of sensitivity that is greater than zero to a higher level of sensitivity, may prevent failure of the cancer cell to respond to one or more chemotherapeutic agents. Increasing sensitivity of a cancer cell to one or more chemotherapeutic agents may increase the response of the cancer cell to treatment with the one or more chemotherapeutic agents, resulting in death of the cancer cell.

Cells that may be treated using an MCJ agonist compound of the invention include but are not limited to cancer cells. A cancer cell that is treated using a method, compound, or composition of the invention may be in vitro or in vivo. An in vivo cell may be in a subject. As used herein the term "one or more" when used in reference to a cell means a single cell or a plurality of cells. A plurality of cells includes at least 2, 3, 4, 5, 6, 7, 8, 9, 10, 20, 50, 100, 500, 1,000, 5,000, 10,000, 50,000, 100,000, 500,000, 1,000,000, 5,000,000, 100,000,000, or more cells, including all integers in between. In some aspects of the invention a cell or plurality of cells may be in cell culture or may be in a subject. A plurality of cells may be a homogeneous or heterogeneous set of cells. As used herein, a homogeneous plurality of cells means a plurality of cells in which one or more cell characteristics of interest are the same for all of the cells in the plurality. It will be understood that a homogeneous plurality of cells may be considered to be homogeneous on the basis that each of the cells has the one or more characteristics of interest that are the same, but the cells need not be entirely identical and features or characteristics, other than the characteristics of interest may differ in different cells of the plurality. For example, a plurality of cells may be referred to as homogeneous if (1) all of the cells naturally express an MCJ molecule or (2) none of the cells naturally express an MCJ molecule, irrespective of other similarities or differences between the cells in the plurality. As used herein a heterogeneous plurality of cells means a plurality of cells in which one or more cell characteristics of interest are different in different cells. For example, a plurality of cells may be referred to as heterogeneous if one or more of the cells in the plurality naturally express an MCJ molecule and one or more of the cells do not naturally express an MCJ molecule, irrespective of other similarities or differences between the cells in the plurality. In certain aspects of the invention, a plurality of cells is in a subject. It will be understood that a cancer cell may naturally express different MCJ molecules at different stages and times. For example, an endogenous MCJ polypeptide or polynucleotide may not be expressed in a cancer cell at certain stages of the cancer cell's life and may be expressed at other stages in the cancer cell's life. Thus, a plurality of cells may include cells that currently have an endogenous MCJ molecule and other cancer cells that do not have an endogenous MCJ molecule and the composition of the plurality of cells with respect to the presence of one or more endogenous MCJ molecules may change at different stages of a cancer. In some aspects of the invention, plurality of cancer cells may be a homogenous plurality or a heterogeneous plurality with respect to expression of one or more MCJ molecules and the plurality of cells may change between being homogeneous and heterogeneous at different stages of one or more cancer cells in the plurality.

As used herein, a subject shall mean a vertebrate animal including but not limited to a human, mouse, rat, guinea pig, rabbit, cow, dog, cat, horse, goat, and primate, e.g., monkey. In certain aspects of the invention, a subject may be a domesticated animal, a wild animal, or an agricultural animal. Thus, the invention can be used to treat diseases or conditions in human and non-human subjects. For instance, methods and compositions of the invention can be used in veterinary applications as well as in human prevention and treatment regimens. In some embodiments of the invention, the subject is a human. In some embodiments of the invention, a subject has one or more cancers.

MCJ agonist compounds of the invention may be administered to a cell, tissue, and/or subject to treat one or more different types of cancer, including but not limited: to a carcinoma, a sarcoma, a leukemia, a lymphoma, a myeloma, a glioma, breast cancer, ovarian cancer, epithelial cancer, uterine cancer, vaginal cancer, prostate cancer, testicular cancer, penile cancer, colon cancer, rectal cancer, cervical cancer, throat cancer, oral cancer, pancreatic cancer, kidney cancer, liver cancer, lung cancer, melanoma, basal cell carcinoma, squamous cell carcinoma, head and neck cancer, stomach cancer, bone cancer, connective tissue cancer, bladder cancer, ocular cancer, nasal cancer, adipose cancer, thyroid cancer, non-Hodgkin lymphoma, small intestine cancer, Wilms tumor, gastrointestinal cancer, central nervous system (CNS) cancer, peripheral nervous system (PNS) cancer, esophageal cancer, Karposi sarcoma, gallbladder cancer, mesothelioma, Hodgkin lymphoma, multiple myeloma, osteoscarcoma, neuroblastoma, rhabdomyoscarcoma, sinus cancer, retinoblastoma, and salivary cancer.

MCJ agonist compounds of the invention may be utilized and administered to treat numerous different types of cells, including but not limited to: a dermal cell, a breast tissue cell, a muscle cell, a circulatory cell, a connective tissue cell, a bone cell, an exocrine cell, an endocrine cell, an organ cell, a mesenchyme cell, a connective tissue cell, an epithelial cell, an endothelial cell, a neuronal cell, a glial cell, a glandular cell, a stromal cell, a renal cell, a thyroid cell, a stem cell, a hematopoietic cell, a lymphoid cell, a myeloid cell, an erythroid cell, a cardiomyocyte, an hepatocyte, an astrocyte, an oligodendrocyte, and an adipocyte. In certain aspects of the invention a cell treated by a method and/or MCJ compound of the invention may be a cancer cell, and the cancer may be any of the aforementioned cancers or other art-known cancers or neoplasms.

In certain aspects of the invention a tumor comprises a plurality of cancer cells is a tumor, which comprises cancer cells in spatial proximity to each other. In some aspects of the invention a plurality of cells may not be in spatial proximity to each other, for example they may be in a subject but may be spatially separated in two or more different spatial regions, tissues, and/or organs of the subject. In some aspects of the invention, a plurality of cancer cells comprises one or more of a primary cancer and a secondary cancer (for example a metastasis); one or more primary cancers; and/or one or more secondary cancers. As used herein a primary cancer is used in reference to the initial, originating cancer and a secondary cancer comprises cancer cells that have broken away from a primary cancer and traveled to and are present in a different tissue or organ in the subject. A cancer cell from a secondary cancer may be the same cancer type as the originating primary cancer. In certain embodiments, a subject may have more than one cancer type. In certain embodiments of the invention a cancer cell is a metastatic cancer cell. In certain aspects of the invention, a cancer cell is resistant to one or more chemotherapeutic agents. In certain embodiments a chemo-resistant cancer cell is cancer cell is a metastatic cancer cell that is part of a metastasis.

Non-limiting examples of subjects to which methods and compounds of the present invention can be applied are subjects who are diagnosed with, suspected of having, or at risk of having one or more cancers. Methods of the invention may be applied to a subject who, at the time of treatment using a method and/or MCJ agonist compound of the invention, has been diagnosed with a cancer and is (1) undergoing treatment for one or more cancers, (2) has undergone treatment for one or more cancers, and/or (3) will be administered a treatment for one or more cancers.

In some aspects of the invention, a subject is at risk of having or developing one or more cancers. A subject at risk of developing a cancer has an increased probability of developing the cancer, compared to a control risk of developing the cancer. In some embodiments of the invention, a level of risk may be statistically significant compared to a control level of risk. A subject at risk may include, for instance, a subject having a genetic abnormality, the presence of which has been demonstrated to have a correlative relation to a higher likelihood of developing a cancer; a subject who has undergone a treatment for a primary cancer (for example, but not intended to be limiting, removal of a primary tumor) but who considered to be at risk for a secondary cancer and/or metastasis and/or another type of cancer; a subject undergoing cancer treatment other than a cancer treatment of the invention; a subject having a family and/or personal medical history of one or more cancers; a subject exposed to agents such as chemical toxins, or activities; and/or subject who has previously been treated for the cancer and is in apparent remission.

In some aspect of the invention, increasing a level in a cancer cell of an MCJ molecule, for example, an MCJ polypeptide encoding polynucleotide or an MCJ polypeptide; may treat the cancer. In some embodiments of the invention, contacting a cancer cell with an exogenous MCJ molecule increases the level of the MCJ molecule in the cell and increases sensitivity of the cancer cell to one or more chemotherapeutic agents, as compared to a substantially similar cancer cell not contacted with the exogenous MCJ molecule. Increasing sensitivity of a cancer cell to a chemotherapeutic agent means that when the cancer cell is contacted by a chemotherapeutic agent, the cell is more likely to respond to the chemotherapeutic agent by dying, as compared to a substantially similar cancer cell that does not have the increased sensitivity to the chemotherapeutic agent. Thus, some embodiments of the invention include methods of administering an exogenous MCJ agonist compound to a cell, tissue, or subject in an amount effective to increase the level of the exogenous MCJ polypeptide activity in the cell, tissue, or subject as a treatment for the cancer.

MCJ polypeptide activity (e.g., level of MCJ polypeptide and/or function of MCJ polypeptide) can be determined and compared to control values of MCJ polypeptide activity according to the invention. A control value may be a predetermined value, which can take a variety of forms. It can be a single cut-off value, such as a median or mean. It can be established based upon comparative groups, such as in groups of cells or individuals having normal amounts of MCJ polypeptide activity and groups of cells or individuals having abnormal amounts of MCJ polypeptide activity. Another example of comparative groups may be groups of cells or subjects having one or more symptoms of or a diagnosis of a cancer and groups of cells or subjects without one or more symptoms of or a diagnosis of a cancer. Another comparative group may be a group of subjects with a history of a cancer and a group of subjects without such a history. The predetermined value, of course, will depend upon the particular population selected. For example, an apparently healthy population of cells may have a different "normal" range than a population of cancer cells. Accordingly, the predetermined value selected may take into account the category in which an individual or cell falls. Appropriate ranges and categories can be selected with no more than routine experimentation by those of ordinary skill in the art. As used herein, "abnormal" means significantly different as compared to a normal control. By abnormally low level of an MCJ polypeptide it is meant low relative to a selected control, and may include a decrease in the level of 0.1%, 0.5%, 1%, 5%, 10%, 20%, 30%, 40%, 50%, 60%, 70%, 80%, 90%, or 100% in a subject or cell as compared to the level in a normal control.

It will be understood that controls according to the invention may be, in addition to predetermined values, samples of materials tested in parallel with the experimental materials. Examples include samples from control populations or control samples generated through manufacture to be tested in parallel with the experimental samples; and also a control may be a sample from a subject prior to, during, or after a cancer treatment, including but not limited to a treatment of the invention.

In certain aspects of the invention, one or more exogenous MCJ molecules are administered to one or more cancer cells in a manner to contact the one or more cells with the exogenous MCJ molecule and to increase the level of the MCJ molecule in the one or more cells. An increase may be, in some aspects of the invention, from a level of an exogenous MCJ molecule previously administered to the cell and/or an endogenous MCJ molecule present in the cell due to natural expression. In certain aspects of the invention, an increase may be from a level of zero to a level greater than zero. In some embodiments of the invention, a level of an MCJ molecule in a cell may increase by at least 0.5%, 1%, 5%, 10%, 20%, 30%, 40%, 50%, 60%, 70%, 80%, 90%, 100%, 200%, 500%, or more from the level of the MCJ molecule in the cell prior to administration of the exogenous MCJ molecule.

Compounds, Molecules, and Methods

The invention in some aspects relates to methods for increasing the level of an MCJ molecule in a cell, tissue, and/or subject. In certain aspects of the invention, increasing the level of an MCJ molecule in a cell may increase MCJ activity in the cell. In some embodiments of the invention, a level of MCJ polypeptide can be increased by increasing expression of an MCJ polypeptide. Thus, some embodiments of the invention methods may include increasing the level of an MCJ polypeptide-encoding polynucleotide in a cell, tissue, or subject, which may result in an increase of one or more of a level and activity of the MCJ polypeptide in the cell, tissue, or subject. In certain embodiments of the invention, methods include increasing the level of an MCJ polypeptide in a cell, tissue, or subject, by delivering the MCJ polypeptide into the cell, tissue or subject, to treat a cancer in the cell, tissue, or subject.

As used herein, the terms "treat", "treated", or "treating" when used with respect to a cancer may refer to a prophylactic treatment that decreases the likelihood of a subject developing the disease or condition, and also may refer to a treatment after the subject has developed the cancer in order to eliminate or ameliorate the cancer, prevent the cancer from becoming more advanced (e.g., metastasizing, spreading, enlarging, etc.), and/or slow the progression of the cancer compared to in the absence of the therapy.

In certain embodiments of the invention, contacting a cancer cell with an exogenous MCJ molecule increases the activity of the MCJ polypeptide in the cancer cell. Examples of MCJ molecules include MCJ polypeptides or polynucleotides that encode MCJ polypeptides. Non-limiting examples of MCJ polypeptides of the invention include: SEQ ID NOs:1-5, 11, 13, 14, 16, 17, and 19-35. One of ordinary skill in the art will understand how to prepare additional MCJ polypeptides that are fragments of a longer MCJ polypeptide and/or fragments of a full-length MCJ polypeptide for use in the methods of the invention. Non-limiting examples of an MCJ polypeptide fragment are set forth as SEQ ID NOs: 30, 31 and 32, which is each a fragment of SEQ ID NO:1 and also a fragment of SEQ ID NO:11, and SEQ ID NO:32 is also a fragment of SEQ ID NO:30 and SEQ ID NO:31. It will be understood that in some embodiments of the invention, a fragment of a full-length MCJ polypeptide may have an amino acid sequence that corresponds to the amino acid sequence set forth as SEQ ID NO:11, or a variant thereof, but without 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, or 145 amino acids corresponding to the full-length MCJ polypeptide sequence set forth as SEQ ID NO:11. Such polypeptides are readily envisioned by one of ordinary skill in the art. For example, though not intended to be limiting, 1, 2, 3, 4 5, 6, 7, 8, 9, 10, 11, 12, or more amino acids may be added to the C terminal end of the sequence that comprises the amino acid sequence set forth as MAARGVIAPVGESLRYAEYL (SEQ ID NO:2), or another MCJ polypeptide sequence disclosed herein. In some aspects of the invention the added amino acids may correspond to the amino acids in the same position as the full-length MCJ polypeptide sequence with the fragment sequence and the full-length sequences are aligned. MCJ polypeptides that are fragments of a full-length MCJ (for example a fragment of SEQ ID NO:11) can be used in embodiments of treatment methods of the invention.

In certain aspects of the invention, an MCJ agonist compound includes an MCJ polypeptide or MCJ-encoding polynucleotide and one or more targeting agents. A non-limiting example of a targeting agent is a cell penetrating peptide, a cell internalization agent, an HIV-derived TAT sequence, a small molecule, a polynucleotide, a liposome, a PEGylated liposome, an aquasome, a biodegradable polymer, a nanoparticle, an oligonucleotide, and a polypeptide. In certain embodiments of the invention a targeting agent assists in one or more of: directing an MCJ agonist compound to a specific cell or tissues, internalization of an MCJ agonist compound into a cell, etc. In certain aspects of the invention, a targeting agent is a cell internalization agent comprising a TAT polypeptide sequence, and optionally comprising a TAT polypeptide sequence set forth as YGKKRRQRR (SEQ ID NO: 36), or a variant thereof, or YGKKRRQRRG (SEQ ID NO: 9), which is SEQ ID NO: 36 with a glycine "G" spacer amino acid, or a variant thereof. In some aspects of the invention, an MCJ agonist compound comprises one or more mitochondrial targeting agents, a non-limiting example of which is a mitochondria-targeting peptide; a nanoparticle that traffics to mitochondria, and a liposome-based delivery system for mitochondria. In certain aspects of the invention, a mitochondrial-targeting agent is a polypeptide, and optionally the polypeptide comprises the amino acid sequence set forth as TRTWVPKGLKSP (SEQ ID NO: 37) or a variant thereof, or GTRTWVPKGLKSP (SEQ ID NO: 10), which is SEQ ID NO: 37 with a glycine "G" spacer amino acid, or a variant thereof. In certain aspects of the invention a mitochondrial-targeting agent is a synthetic polypeptide, and optionally the polypeptide comprises the amino acid sequence set forth as SEQ ID NO: 39, which includes the amino acid sequence $F_xRF_xKF_xRF_xK$ wherein $F_x$ represents a cyclohexylalanine amino acid residue. A non-limiting example of an MCJ agonist polypeptide of the invention that includes the amino acid sequence $F_xRF_xKF_xRF_xK$ (SEQ ID NO: 39) and an MCJ polypeptide is MITO-N-MCJ, the sequence of which is: $F_xRF_xKF_xR$-$F_x$KMAARGVIAPVGESLRYAEYL (SEQ ID NO: 38).

In certain aspects of the invention, an exogenous MCJ agonist compound comprises an MCJ polypeptide, and one or more targeting polypeptides. A peptide in an MCJ agonist compound may, in some embodiments of the invention, be a variant of a polypeptide described herein. Thus, an MCJ polypeptide in an agonist compound of the invention may have a sequence set forth herein or a variant thereof. Similarly, in certain embodiments of the invention, a targeting agent may be targeting agent described herein, another art-known targeting polypeptide, or a variant thereof. In embodiments that include a polypeptide targeting agent the polypeptide may comprise an amino acid sequence such as one set forth herein, the amino acid sequence of another art-known targeting polypeptide, or a variant thereof. It will be understood that variants of targeting agents are also encompassed in some aspects of the invention. For example, an amino acid sequence of a peptide targeting agent may be modified from one described herein, or from another art-known targeting polypeptide sequence. A skilled artisan can prepare and utilize variant targeting agents using standard methods in conjunction with the disclosure set forth herein.

A variant polypeptide (also referred to herein as a "modified" polypeptide) may include deletions, point mutations, truncations, amino acid substitutions and/or additions of amino acids or non-amino acid moieties. Modifications of a polypeptide of the invention may be made by modification of the nucleic acid sequence that encodes the polypeptide or alternatively, modifications may be made directly to the polypeptide, such as by cleavage, addition of a linker molecule, addition of a detectable moiety, such as a fluorescent label, and the like. Modifications also embrace fusion proteins comprising all or part of the polypeptide's amino acid sequence. In certain embodiments of the invention, a modification of a polypeptide may be acetylation of the polypeptide. In a non-limiting example, an MCJ polypeptide variant may be an MCJ polypeptide that is acetylated at one or more amino acid residues. SEQ ID NO:5 is a non-limiting example of an MCJ polypeptide that includes an acetylated lysine residue. An MCJ polypeptide of the invention may comprise one or more acetylated amino acid residues, and in certain embodiments of the invention, an MCJ polypeptide includes an acetylated lysine (K) residue. In certain embodiments of the invention the position of an acetylated lysine residue in the amino acid sequence of an MCJ polypeptide corresponds to the K25 position in the sequence set forth as SEQ ID NO:1 when the amino acid sequence of the MCJ polypeptide is aligned with amino acid sequence set forth as SEQ ID NO:1. In certain embodiments of the invention, in addition to or in the absence of an acetylated lysine that corresponds to K25 of the sequence of SEQ ID NO:1, one or more other amino acid residues in an MCJ polypeptide of the invention may be acetylated.

In certain embodiments of the invention, a polypeptide variant may be a polypeptide that is modified specifically to alter a feature of the polypeptide unrelated to its physiological activity. For example, cysteine residues can be substituted or deleted to prevent unwanted disulfide linkages. A residue may be added at the N or C-terminal end of the polypeptide, for example, SEQ ID NO:16, includes a cysteine residue (C) at the extreme C-terminal end of the MCJ polypeptide set forth as (SEQ ID NO:2). Polypeptides can be synthesized with modifications and/or modifications can be made in a polypeptide by selecting and introducing an amino acid substitution, deletion, or addition. Modified polypeptides then can be tested for one or more activities (e.g., increasing sensitivity of a cancer cell to a chemotherapeutic agent, efficacy in killing a cancer cell, etc.) to determine which modification provides a modified polypeptide with the desired properties.

The skilled artisan will also realize that conservative amino acid substitutions may be made in a polypeptide to provide functionally equivalent polypeptides, i.e., a modified MCJ polypeptide, or modified MCJ agonist compound that retains a functional capability of an unmodified MCJ polypeptide, or unmodified MCJ agonist compound, respectively. As used herein, a "conservative amino acid substitution" refers to an amino acid substitution that does not alter the relative charge or size characteristics of the polypeptide in which the amino acid substitution is made. Conservative substitutions of amino acids may, in some embodiments of the invention, include substitutions made amongst amino acids within the following groups: (a) M, I, L, V; (b) F, Y, W; (c) K, R, H; (d) A, G; (e) S, T; (f) Q, N; and (g) E, D. Polypeptide variants can be prepared according to methods for altering polypeptide sequence and known to one of ordinary skill in the art such. Non-limiting examples of functionally equivalent polypeptide variants are MCJ polypeptides with conservative amino acid substitutions of an MCJ polypeptide, and/or are fragments of an MCJ polypeptide. In certain embodiments of the invention, an MCJ polypeptide variant comprises a fragment of the amino acid sequence of an MCJ polypeptide and the fragment has at least 75%, 80%, 85%, 90%, 95%, 97%, 98%, 99%, or 100% sequence identity to the region of the amino acid sequence of the MCJ polypeptide with which it aligns.

As used herein the term "modified" or "modification" in reference to a polynucleotide or polypeptide sequence refers to a change of one, two, three, four, five, six, or more nucleic acids or amino acids, respectively, in the sequence as compared to the corresponding unmodified sequence. For example, though not intended to be limiting, a modified polypeptide sequence may be identical to that of a first MCJ polypeptide sequence except that it has one, two, three, four, five, or more amino acid substitutions, deletions, insertions, or combinations thereof, and thus is a variant of the first MCJ polypeptide sequence.

The invention, in some aspects, includes polypeptides having one or more substitutions or other modifications from those described herein. For example, though not intended to be limiting, a sequence of a MCJ polypeptide can be modified with one or more substitutions, deletions, insertions, or other modifications and can be tested using methods described herein for characteristics including, but not limited to: expression; cell localization; efficacy in increasing sensitivity of a cancer cell to a chemotherapeutic agent; efficacy in reducing resistance of a cancer cell to a chemotherapeutic agent; and efficacy of the polypeptide to kill a cancer cell. MCJ molecules of the present invention include MCJ polypeptide and nucleic acid sequences provided herein and variants that have at least about 75%, 80%, 85%, 90%, 95%, 96%, 97%, 98%, or 99% identity to an amino acid or nucleic acid sequence, respectively, described herein. MCJ agonist compounds of the present invention may, in some embodiments, include one or more MCJ and targeting polypeptide sequences provided herein and variants that may have an amino acid sequence with at least 75%, 80%, 85%, 90%, 95%, 96%, 97%, 98%, or 99% identity to an amino acid sequence described herein. It will be understood that a polynucleotide that encodes a polypeptide MCJ agonist compound of the invention may comprise a nucleic acid sequence that has least 75%, 80%, 85%, 90%, 95%, 96%, 97%, 98%, or 99% identity to a nucleic acid sequence encoding a polypeptide sequence described herein.

Sequence identity can be determined using standard techniques known in the art. To determine the percent identity (similarity) of two amino acid sequences the sequences are aligned for optimal comparison purposes (e.g., gaps may be introduced in the sequence of one protein for optimal alignment with the other protein). The amino acid residues at corresponding amino acid positions are then compared. When a position in one sequence is occupied by the same amino acid residue as the corresponding position in the other sequence, then the molecules have identity/similarity at that position. The percent identity or percent similarity between the two sequences is a function of the number of identical positions shared by the sequences (i.e., % identity or % similarity=number of identical positions/total number of positions×100). Such an alignment can be performed using any one of a number of well-known computer algorithms designed and used in the art for such a purpose. Similarly, percent identity/similarity of polynucleotide sequences encoding a polypeptide of the invention can be determined using art-known alignment and comparison methods for nucleic acids. MCJ and/or targeting polypeptides of the invention may be shorter or longer than MCJ and/or targeting polypeptide sequences, respectively, set forth herein. In addition, nucleic acids of the invention may be used to obtain additional coding regions, and thus additional polypeptide sequences, using techniques known in the art.

Modified sequences, (which are also referred to herein as variants) may in some embodiments be prepared by site specific mutagenesis of nucleic acids in the DNA encoding a polypeptide of the invention, using cassette or PCR mutagenesis or other techniques known in the art, to produce DNA encoding the polypeptide, and thereafter expressing the DNA in recombinant cell culture. Where amino acid substitutions are made to a small fragment of a polypeptide, the substitutions can be made by directly synthesizing the polypeptide. In certain embodiments of the invention, activity of variant or fragment of a polypeptide can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

Amino acid substitutions are typically of single residues and in certain embodiments of the invention, 1, 2, 3, 4, 5, 6, 7 8, 9, 10, 11, 12, 13, 14, 15, 16, 17, 18, 19, 20 or more substitutions can be made in the amino acid sequence of an MCJ and/or targeting polypeptide of the invention, for example, though not intended to be limiting, in a sequence set forth here as SEQ ID NOs:1-35. Amino acid insertions in the amino acid sequence of an MCJ and/or targeting polypeptide of the invention, for example, though not intended to be limiting, in a sequence set forth here as SEQ ID NOs:1-35 may include insertion of 1, 2, 3, 4, 5, 6, 7, 8, 9, 10, 11, 12, 13, 14, 15, 16, 17, 18, 19, or 20 amino acids, although larger insertions may be tolerated. Amino acid deletions in the sequence of an MCJ and/or targeting polypeptide of the invention, for example, though not intended to be limiting, in a sequence set forth here as SEQ ID NOs:1-35 may include deletions of 1, 2, 3, 4, 5, 6, 7, 8, 9, 10, 11, 12, 13, 14, or 15 amino acids, although larger deletions may be tolerated. Substitutions, deletions, insertions or any combination thereof may be used to arrive at a final modified MCJ and/or targeting polypeptide that may be components of certain MCJ agonist compounds of the invention. Generally these changes are done on a few amino acids to minimize the alteration of the molecule. However, larger changes may be tolerated in certain circumstances. A modified MCJ and/or targeting polypeptide of the invention may, in some embodiments, incorporate unnatural amino acids as well as natural amino acids. An unnatural amino acid can be included in an MCJ and/or targeting polypeptide of the invention to enhance a characteristic such as cell penetration, targeting, delivery, function, stability, or to lower toxicity, etc.

Treatments and Methods

Exogenous MCJ agonist compounds of the invention that increase a level of the MCJ molecule in a cancer cell may be administered in an effective amount to a subject in need of treatment of a cancer. Administering to a subject an exogenous MCJ agonist compound that increases a MCJ polypeptide level and/or activity may reduce a cancer in the subject. An exogenous MCJ agonist compound useful to treat a cancer may, in some embodiments of the invention be a polynucleotide that encodes an MCJ polypeptide. Thus, a method of the invention may include administering an exogenous MCJ polypeptide or exogenous MCJ polypeptide-encoding nucleic acid to a subject.

As used herein, the terms "protein" and "polypeptide" are used interchangeably and thus the term polypeptide may be used to refer to a full-length protein and may also be used to refer to a fragment of a full-length protein. As used herein, the terms "polynucleotide" and "nucleic acid sequence" may be used interchangeably and may comprise genetic material including, but not limited to: RNA, DNA, mRNA, cDNA, etc., which may include full length sequences and/or fragments thereof. As used herein the terms: "MCJ polypeptide" or "MCJ-encoding polynucleotide" of the invention will be understood to refer to MCJ sequences disclosed herein and variants of such sequences. As used herein with respect to polypeptides, proteins, or fragments thereof, and polynucleotides that encode such polypeptides the term "exogenous" means the compound is administered to a cell or subject and was not naturally present in the cell or subject. It will be understood that an exogenous MCJ polypeptide or MCJ polypeptide-encoding nucleic acid sequence may be identical to an endogenous MCJ polypeptide or MCJ polypeptide-encoding nucleic acid sequence, respectively, in terms of its sequence, but was administered to the cell or subject.

Nomenclature used herein for MCJ polypeptides may, in certain embodiments of the invention, include reference to the N-terminal end of the MCJ polypeptide as an indicator of the region of a MCJ polypeptide in relation to a full-length MCJ polypeptide. Thus, an "N-" or "-N-" indicator used in some MCJ sequences herein refers to the correspondence of the sequence of the MCJ polypeptide to the N-terminal region of a full-length MCJ polypeptide. It will be understood that nomenclature used herein in relation to MCJ polypeptides of the invention, may but need not include an "-N-" or "N-" in reference to the "N-terminal". Thus, an MCJ polypeptide that is referred to herein as an "N-MCJ polypeptide" may also be referred to as an "MCJ polypeptide". Similarly, an MCJ agonist compound of the invention referred to herein as "TAT-N-MCJ-MTS" may also be referred to herein as "TAT-MCJ-MTS". The "N", which refers to the MCJ amino acid sequence as beginning at the N-terminal amino acid of MCJ. It will be understood some but not all MCJ polypeptides that are useful in embodiments of methods and compounds of the invention include the N-terminal amino acid, which is Methionine (M). In certain embodiments of methods and compounds of the invention, an MCJ agonist compound may comprise an MCJ polypeptide that does not include the amino acid in the residue position that corresponds to position 1, 2, 3, 4, 5, 6 (which correspond to amino acids: M, A, A, R, G, V, respectively) or higher beginning at the N-terminal of an MCJ polypeptide such as SEQ ID NO:1, SEQ ID NO:2, and SEQ ID NO:11, which each include the N-terminal amino acid (M). Non-limiting examples of MCJ polypeptide sequences that do not include the N-terminal amino acid "M" but are useful in methods and compounds of the invention are SEQ ID NOs:3, 4, 22, 23, and 32-34.

According to some aspects of the invention, one or more exogenous MCJ polypeptides may be administered in methods of the invention. In some embodiments of the invention, a level or function of a MCJ polypeptide may be modulated by genetically introducing an MCJ polypeptide into a cell and/or mitochondria, and reagents and methods are provided for genetically targeted expression of MCJ polypeptides. Genetic targeting can be used to deliver MCJ polypeptides to specific cell types, to specific cell subtypes, to specific spatial regions within an organism, and to sub-cellular regions within a cell. Genetic targeting also relates to the control of the amount of an MCJ polypeptide expressed, and the timing of the expression. Some embodiments of the invention include a reagent for genetically targeted expression of an MCJ polypeptide, wherein the reagent comprises a vector that contains a nucleic acid that encodes an MCJ polypeptide or encodes a functional fragment of an MCJ polypeptide.

As used herein, the term "vector" refers to a polynucleotide molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert MCJ polypeptides into dividing and non-dividing cells and can insert MCJ polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. In certain embodiments of the invention, a vector may be a lentivirus comprising a nucleic acid or gene that encodes an MCJ polypeptide of the invention or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of an MCJ polypeptide in a wide variety of cell types—thus a promoter for a gene that is widely expressed in a variety of cell types, for example a "housekeeping gene" can be used to express an MCJ polypeptide in a variety of cell types. Non-limiting examples of general promoters are provided elsewhere herein and suitable alternative promoters are well known in the art. In certain embodiments of the invention, a promoter may be an inducible promoter, examples of which include, but are not limited to tetracycline-on or tetracycline-off, etc.

Additional compounds that may be administered in treatment methods of the invention include small molecule or chemical MCJ agonists that increase MCJ polypeptide activity. Methods of identifying and testing such small molecules and chemicals may include use of art-known library screening and testing procedures in conjunction with the teaching provided herein.

Administration Strategies

MCJ agonist compounds of the invention may be administered singly or in combination with one or more additional compounds. In some embodiments, an MCJ agonist compound of the invention may act in a synergistic manner with one or more additional therapeutic agents or treatments and increase the effectiveness of the one or more therapeutic agents or activities. Thus, for example, administration of an MCJ agonist compound to a cancer cell in conjunction with chemotherapeutic agent may enhance the cancer cell killing efficacy of the chemotherapeutic agent. Thus, an MCJ agonist compound may increase the effectiveness of one or more chemotherapeutic agents or treatments that are administered to treat a cancer. A non-limiting example of a chemotherapeutic agent is: a taxane, an anthracyclines, a platinum-based drug, an anti-metabolite, a base analog, a nucleoside analogue, a nucleotide analogue, an antifolate, methotrexate, an alkaloid, vincristine, vinblastine, irinotecan, etoposide, velcade, a tyrosine kinase inhibitor, a serine/threonine kinase inhibitor, bleomycin, cyclophosphamide, cytoxan, everolimus, and metformin. Treatment methods of the invention may also result in increased sensitivity of a cancer cell to other art-known chemotherapeutic agents as the result of the cancer cell being contacted with an MCJ agonist compound of the invention.

It will be understood that additional MCJ agonist compounds can be identified and used in methods of the invention. For example, assays and methods presented herein can be used to assess candidate compounds for their ability to increase MCJ polypeptide levels and/or activity and their ability to treat a cancer when administered to a cell and/or subject. MCJ agonist compounds of the invention described herein can be used alone or in conjunction with other molecules such as targeting agents, labeling agents, and/or cytotoxic agents in treatment methods of the invention.

Targeting agents useful in some aspects of the invention are targeting agents that direct or assist in directing an MCJ agonist compound of the invention to a specific cell type to be treated such as a dermal cell, a breast tissue cell, a muscle cell, a stem cell, a circulatory cell, a connective tissue cell, a bone cell, an exocrine cell, an endocrine cell, an organ cell, a mesenchyme cell, a connective tissue cell, an epithelial cell, an endothelial cell, a neuronal cell, a glial cell, a glandular cell, a stromal cell, a renal cell, a thyroid cell, a stem cell, a hematopoietic cell, a lymphoid cell, a myeloid cell, an erythroid cell, a cardiomyocyte, an hepatocyte, an astrocyte, an oligodendrocyte, an oocyte, or an adipocyte. Certain targeting agents useful in some aspects of the invention may be agents that direct or assist in directing an MCJ agonist compound to an organelle such as a mitochondrion.

A targeting agent of choice will depend upon the nature of the cancer. In some instances it may be desirable to target the MCJ agonist compound to one or more dermal cells, breast tissue cells, muscle cells, circulatory cells, connective tissue cells, stem cells, bone cells, exocrine cells, endocrine cells, organ cell, mesenchyme cells, connective tissue cells, epithelial cells, endothelial cells, neuronal cells, glial cells, glandular cells, stromal cells, renal cells, thyroid cells, stem cells, hematopoietic cells, lymphoid cells, myeloid cells, erythroid cells, cardiomyocytes, hepatocytes, astrocytes, oligodendrocytes, oocytes, and adipocytes. Those of ordinary skill in the art will be aware of and will be able to select and use suitable targeting agents in embodiments of the invention using routine methods. A non-limiting example of a targeting agent useful in certain embodiments of the invention is a cell-penetrating peptide, a cell internalization agent, an HIV-derived TAT sequence, a small molecule, a polynucleotide, a liposome, a PEGylated liposome, an aquasome, a biodegradable polymer, a nanoparticle, an oligonucleotide, and other targeting polypeptides. A non-limiting example of a cell targeting polypeptide that may be used to deliver an MCJ agonist compound into a cell in certain embodiments of the invention is a TAT polypeptide comprising the sequence: YGKKRRQRRG (SEQ ID NO:9), or a variant thereof.

The invention in some aspects includes a targeting agent to deliver an MCJ agonist compound of the invention to mitochondria. A non-limiting example of a mitochondrial targeting agent is a Gramicidin S based mitochondrial targeting agent, a mitochondria-targeting peptide; a nanoparticle that traffics to mitochondria, and a liposome-based delivery systems for mitochondria, an agent utilizing the carnitine-acylcarnitine translocase system, cytochromes, and malate dehydrogenase. Additional examples of targeting signals that may be used in some embodiments of the invention are set forth in Diekert, K., et al., PNAS (1999) vol 96, No. 21, 11752-11757; Addya, S., et al., J. Cell Biology, (1997) Vol. 139, No. 3, 589-599; Del Gaizo, V., et al., (2003) Mol. Gen. and Metabol., Vol. 80, 170-180, which are incorporated herein by reference. In certain aspects of the invention, a mitochondrial-targeting agent is a polypeptide, and optionally the polypeptide comprises the amino acid sequence set forth as GTRTWVPKGLKSP (SEQ ID NO:10), or a variant thereof.

Labeling agents may be used in certain embodiments of methods and compounds of the invention to determine the location of MCJ agonist compounds in cells and tissues and also, may be used to assess the cell, tissue, or organelle location of treatment compounds that have been administered. Procedures for attaching and utilizing labeling agents such as enzymatic labels, dyes, radiolabels, fluorescent labels, etc. are well known in the art.

Compositions, compounds, and methods of the invention may be enhanced by utilization in combination with other procedures for treating a cancer. In some instances a treatment procedure may involve administration of another therapeutic agent or treatment such a medicament and/or surgery, radiation therapy, etc. Thus, in some embodiments of the invention, administration of an MCJ agonist compound of the invention may be performed at one of more of: prior to, coincident with, or after administration of another therapy for treating the cancer. Treatment methods of the invention that include administration of an MCJ agonist compound can be used at any stages of a cancer including in a pre-cancer, dysplasia, tumor, metastasis, remission, relapse, etc. Methods of the invention may also be used for subjects who have previously been treated with one or more other anti-cancer medicament, chemotherapeutic, surgery, or radiation methods that were not successful, were minimally successful, and/or are no longer successful at slowing or stopping progression of the cancer in the subject. For example, though not intended to be limiting, an MCJ agonist compound of the invention may be administered to a subject, or contacted to a cancer cell, when the subject or cell is chemotherapy resistant. Administration of an MCJ agonist to one or more cancer cells may reduce chemoresistance of one or more of the contacted cancer cells and increase sensitivity of one or more of the contacted cancer cells to treatment with a chemotherapeutic agent.

Effective Amounts

MCJ agonist compounds of the invention are administered to a cell or subject in an effective amount for treating a cancer. An "effective amount for treating a cancer" is an amount necessary or sufficient to realize a desired biologic effect. For example, an effective amount of an MCJ agonist compound of the invention could be that amount necessary to do one or more of (i) slowing or halting progression of the cancer; (ii) killing a plurality of cancer cells, and (iii) reversing one or more symptoms of the cancer. According to some aspects of the invention, an effective amount is that amount of an MCJ agonist compound of the invention alone or in combination with another medicament or treatment, which when combined or co-administered or administered alone, results in a desired therapeutic response in the cancer, either in the prevention or the treatment of the cancer. In some aspects of the invention, a desired biological effect may be one or more of: death of a plurality of cancer cells; an increase in sensitivity of one or more cancer cells to a chemotherapeutic agent; the amelioration and or absolute elimination of symptoms resulting from the cancer; the complete abrogation of the cancer, as evidenced for example, by a diagnostic test that indicates the subject is free of the cancer, or that one or more of the presence, level, or tumor size, and severity of the cancer is reduced.

Typically an effective amount of an MCJ agonist compound will be determined in clinical trials, establishing an effective dose for a test population versus a control population in a blind study. In some embodiments, an effective amount will be that results in a desired response, e.g., an amount that diminishes a cancer; increases chemo-sensitivity of one or more cancer cells, maintains a cancer in remission in cells and/or a subject with the cancer. Thus, an effective amount to treat a cancer may be the amount that when administered increases the amount of an exogenous MCJ polypeptide in the subject to an amount that is above the amount that would occur in the subject or tissue without the administration of the MCJ agonist compound. In the case of treating a cancer a desired response to a treatment of the invention may be reducing or eliminating one or more symptoms or physiological characteristics of the cancer in a cell, tissue, and/or subject. The reduction or elimination may be temporary or may be permanent. The status of the cancer can be monitored using art-known methods. In some aspects of the invention, a desired response to treatment of a cancer may comprise delaying or preventing onset of the cancer, slowing, delaying, or stopping a cancer's progression, maintaining remission of a cancer, etc.

An effective amount of an MCJ agonist compound of the invention may also be determined by assessing physiological effects of administration of the MCJ agonist compound on a cell or subject, such as a an increase in cancer cell death, a decrease of the cancer, an increase in chemo-sensitivity of the cancer, etc. following administration. As herein the term "administrating" when used in reference to treating one or more cancer cells means contacting the one or more cancer cells with the MCJ agonist compound. Similarly, in some embodiments of treatment methods of the invention, administrating an MCJ agonist compound to a subject comprises contacting one or more cancer cells of the subject with the administered MCJ agonist compound. In certain embodiments of the invention, an MCJ agonist compound is part of a pharmaceutical composition. An MCJ agonist compound of the invention may be administered as part of a pharmaceutical composition, wherein the manner of administration is suitable to contact one or more cancer cells with the MCJ agonist compound. A pharmaceutical composition of the invention that includes an MCJ agonist compound may also include a pharmaceutically acceptable carrier.

Assays suitable to determine efficacy of an MCJ agonist compound of the invention will be known to those skilled in the art and can be employed for measuring the level of the response to a treatment and an amount of an MCJ agonist compound administered to a subject can be modified based, at least in part, on such measurements. Non-limiting examples of measurements of response to a cancer treatment of the invention include cancer diagnostic testing, staging, tumor measure, scans, etc. The amount of a treatment may be varied for example by one or more of: increasing or decreasing the amount of a pharmaceutical composition administered, changing the pharmaceutical composition administered, changing the route of administration, changing the dosage timing, changing administration of another therapeutic agent, a non-limiting example of which is a chemotherapeutic agent, and so on. The effective amount will vary with the particular cancer being treated, the age and physical condition of the subject being treated; the stage and severity of the cancer, the duration of the treatment, the nature of a prior, concurrent, or impending therapy (if any), the specific route of administration, and additional factors within the knowledge and expertise of the health practitioner. For example, an effective amount may depend upon the degree to which an individual has endogenous MCJ molecules present in one or more cancer cells, and/or whether the subject's cancer cells are chemo-resistant, or other factors.

An effective amount of one or more of an MCJ agonist compound, an MCJ molecule, an MCJ polypeptide or its encoding polynucleotide for treatment of a cancer may vary depending upon the specific compound or molecule, the mode of delivery of the compound or molecule, and whether it is used alone or in combination with another therapeutic agent or compound. The effective amount for any particular application can also vary depending on such factors as the cancer being treated, the particular compound being administered, the size of the subject, or the severity of the metabolic disease or condition. A skilled artisan can empirically determine the effective amount of a particular compound of the invention without necessitating undue experimentation. Combined with the teachings provided herein, by choosing among the various active MCJ agonist compounds and MCJ molecule and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat a cancer in a particular subject.

A pharmaceutical composition dosage and/or dosage of an MCJ molecule may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, an MCJ agonist compound of the invention can be administered at least daily, every other day, weekly, every other week, monthly, etc. Doses may be administered once per day or more than once per day, for example, 2, 3, 4, 5, or more times in one 24 hour period.

Pharmaceutical compositions of the invention may be administered alone, in combination with each other, and/or in combination with other drug therapies, or other treatment regimens that are administered to subjects with a metabolic disease or condition. Pharmaceutical compositions used in the embodiments of the invention preferably are sterile and contain an effective amount of an MCJ agonist compound to do one or more of (1) increase sensitivity to a chemotherapeutic agent in a contacted cancer cell, (2) decrease resistance to a chemotherapeutic agent in a contacted cancer cell, (3) kill a contacted cancer cell, (4) produce the desired therapeutic response in a unit of weight or volume suitable for administration to a subject.

The doses of a pharmaceutical composition and/or an MCJ agonist compound to treat a cancer that is administered to a subject can be chosen in accordance with different parameters, in particular in accordance with the mode of administration used and the state of the subject. Other factors may include the desired period of treatment. In the event that a response in a subject is insufficient at the initial doses applied, higher doses (or effectively higher doses by a different, more localized delivery route) may be employed to the extent that patient tolerance permits.

Administration Methods

A variety of administration routes for an MCJ agonist compound are available. The particular delivery mode selected will depend upon the particular condition being treated and the dosage required for therapeutic efficacy. Methods of this invention, generally speaking, may be practiced using any mode of administration that is medically acceptable, meaning any mode that produces effective levels of treatment without causing clinically unacceptable adverse effects. In some embodiments of the invention, an MCJ agonist compound of the invention may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, an MCJ agonist compound of the invention may be placed within a slow release matrix and administered by placement of the matrix in the subject. In some aspects of the invention, an MCJ agonist compound may be administered to a cell and/or subject using nanoparticles coated with a delivery agent that targets a specific cell or organelle, a non-limiting example of which is a mitochondrion.

An MCJ agonist compound of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a pharmaceutical composition. In general, a pharmaceutical composition comprises the compound of the invention and a pharmaceutically-acceptable carrier. Pharmaceutically acceptable carriers are well known to the skilled artisan and may be selected and utilized using routine methods. As used herein, a pharmaceutically-acceptable carrier means a non-toxic material that does not interfere with the effectiveness of the biological activity of the active ingredients, e.g., the ability of the MCJ agonist compound to increase sensitivity of a contacted cancer cell to a chemotherapeutic agent and/or the ability of the MCJ agonist compound to kill a cancer cell.

Pharmaceutically acceptable carriers may include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In some embodiments of the invention, an MCJ agonist compound maybe administered directly to a tissue. In some embodiments, the tissue to which the compound is administered is a tissue in which cancer is present or is likely to be present or to arise. Direct tissue administration may be achieved by direct injection, or other art-known means. An MCJ agonist compound may be administered once, or alternatively may be administered in a plurality of administrations. If administered multiple times, an MCJ agonist compound may be administered via different routes. For example, the first (or the first few) administrations may be made directly into the affected tissue while later administrations may be systemic.

An MCJ agonist compound, when it is desirable to have it administered systemically, may be formulated for parenteral administration by injection, e.g., by bolus injection or continuous infusion. Formulations for injection may be presented in unit dosage form, e.g., in ampoules or in multi-dose containers, with or without an added preservative. The pharmaceutical compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of one or more MCJ agonist compounds.

In yet other embodiments, a delivery vehicle is a biocompatible microparticle or implant that is suitable for implantation into the mammalian recipient. Exemplary bioerodible implants that are useful in accordance with this method are described in PCT Publication No. WO 95/24929 (incorporated by reference herein), which describes a biocompatible, biodegradable polymeric matrix for containing a biological macromolecule. Such delivery means are well known in the art and can be used to achieve sustained release of a compound of the invention in a subject, and may be selected not to degrade, but rather, to release by diffusion over an extended period of time.

Both non-biodegradable and biodegradable polymeric matrices can be used to deliver one or more MCJ agonist compounds of the invention to a cell and/or subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In certain embodiments of the invention, an MCJ agonist compound may be delivered using the bioerodible implant by way of diffusion, or by degradation of the polymeric matrix. Exemplary synthetic polymers for such use are well known in the art. Biodegradable polymers and non-biodegradable polymers can be used for delivery of one or more MCJ agonist compounds of the invention using art-known methods. Bioadhesive polymers such as bioerodible hydrogels (see H. S. Sawhney, C. P. Pathak and J. A. Hubell in Macromolecules, 1993, 26, 581-587, the teachings of which are incorporated herein) may also be used to deliver one or more MCJ agonist compounds of the invention for treatment. Additional suitable delivery systems can include time-release, delayed release or sustained-release delivery systems. Such systems can avoid repeated administrations of an MCJ agonist compound, increasing convenience to the subject and the physician. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be particularly suitable for prophylactic treatment of subjects and for subjects at risk of developing a recurrent cancer. Long-term release, as used herein, means that the implant is constructed and arranged to delivery therapeutic levels of the active ingredient for at least 30 days, 60 days, 90 days or longer. Long-term sustained release implants are well-known to those of ordinary skill in the art and include some of the release systems described above.

Therapeutic formulations of one or more MCJ agonist compounds of the invention may be prepared for storage by mixing the MCJ agonist compound having the desired degree of purity with optional pharmaceutically acceptable carriers, excipients or stabilizers [Remington's Pharmaceutical Sciences $21^{st}$ edition, (2006)], in the form of lyophilized formulations or aqueous solutions. Acceptable carriers, excipients, or stabilizers are nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Efficacy Determination and Assays

Certain aspects of the invention include methods to assess the efficacy of an MCJ agonist compound in treatment of a cancer. Such methods may include comparing the effect on a cancer test cell contacted with an MCJ agonist compound to the status of a substantially similar cancer control cell that is not contacted with the MCJ agonist compound. A change in one or more of desirable effects such as, but not limited to: increased chemo-sensitivity, increased likelihood of cell death, and decreased chemo-resistance of the contacted test cell compared to the control cell indicates effectiveness of the MCJ agonist compound for treatment of cancer. In some embodiments of the invention, assay methods may include obtaining a biological sample from a subject, contacting with an MCJ agonist compound, optionally contacting the cell with a chemotherapeutic agent and assessing the cell's response (e.g., increased chemo-sensitivity, increased likelihood of cell death, decreased chemo-resistance, etc.). The test cell's response may be compared to a control cancer cell. As used herein a biological sample may be an in vitro biological sample, or may a sample that is detected (e.g., obtained) in vivo. As used herein, a biological sample may be a cell sample, tissue sample, blood sample, bodily fluid sample, subcellular sample, etc. A biological sample may include cells, tissues, or organelles and may include cell types such as but not limited to: dermal cells, breast tissue cells, muscle cells, circulatory cells, connective tissue cells, stem cells, bone cells, exocrine cells, endocrine cells, organ cell, mesenchyme cells, connective tissue cells, epithelial cells, endothelial cells, neuronal cells, glial cells, glandular cells, stromal cells, renal cells, thyroid cells, stem cells, hematopoietic cells, lymphoid cells, myeloid cells, erythroid cells, cardiomyocytes, hepatocytes, astrocytes, oligodendrocytes, oocytes, and adipocytes. In some embodiments of the invention, a biological sample may comprise one or more cancer cells.

Assays to assess a cancer may include but are not limited to (1) characterizing the efficacy of an MCJ agonist compound in treating a cancer in a subject; (2) evaluating a combination treatment comprising administering one or more MCJ agonist compounds and administering one or more chemotherapeutic agents, radiation treatments, surgical treatments, and other therapeutic treatments, (3) selecting a treatment for a cancer based at least in part on the determined efficacy of the MCJ agonist compound alone or in combination; and (4) administering an MCJ agonist as at least a portion of a treatment of a cancer in a subject. Thus, subjects can be characterized, treatment regimens can be monitored, treatments can be selected and diseases status can be better understood using embodiments of methods of the present invention.

The invention, in some aspects, includes various assays to determine the efficacy of an MCJ polypeptide administered to a cancer cell and/or subject. Methods of the invention that are useful to determine MCJ polypeptide efficacy in cells, tissues, subjects, and samples (e.g., from subjects, in culture, etc.), include, but are not limited to: diagnostic assays to determine cancer cell death, chemo-sensitivity of cancer cells, etc. Assessments of efficacy of an MCJ polypeptide to treat a cancer can be done in vitro, for example in cell culture, cell samples, cell suspensions, etc. or can be done in vivo, for example in a living subject using art-known cancer diagnostic assessments and tracking methods. Assessment of efficacy of candidate MCJ agonist compounds to treat a cancer may also be done using assays of the invention in cells from culture—e.g., as screening assays to assess candidate MCJ agonist compounds ability to do one or more of: increase chemo-sensitivity, decrease chemo-resistance, and increase cancer cell death. MCJ agonist compounds that effectively increase chemo-sensitivity, increase cancer cell death, and/or decrease chemo-resistance in a cell, tissue, or subject may be used in the treatment of a cancer in one or more therapeutic regimens, non-limiting examples of which include: administration of one or more MCJ agonist compounds to a cell or subject: alone, prior to, during, or following administration of a chemotherapeutic agent, a radiation therapy, cancer surgery, etc. It will be understood that a therapeutic regimen may be either prophylactic or a treatment of a cancer in a subject.

In some embodiments of the invention, a cancer treatment efficacy of an MCJ agonist compound that comprises an MCJ polypeptide can be assessed by determining whether contacting a cancer cell with an MCJ agonist compound increases the level and/or activity of the MCJ polypeptide in a cell or tissue. In certain embodiments of the invention, an activity in a cancer cell that can be assessed to determine efficacy of an administered MCJ polypeptide may be one or more of mitochondrial ATP production in a cancer cell contacted with the MCJ polypeptide, a level of ABC-transporters in a cancer cell contacted with the MCJ polypeptide, and death of a cancer cell contacted with the MCJ polypeptide. One or more of a reduction in mitochondrial ATP production in the cancer cell, a decrease in a level of ABC-transporters in the cancer cell, and death of the cancer cell contacted with an MCJ agonist compound indicates efficacy of the administered MCJ polypeptide as a treatment for cancer.

As will be appreciated by those of ordinary skill in the art, the evaluation of a treatment also may be based upon an evaluation of the symptoms or clinical end-points of a cancer and such evaluations can be used in conjunction with methods of the invention to assess the status of a cancer and/or the efficacy of a treatment of the invention for a cancer.

Kits

Also within the scope of the invention are kits that comprise compounds and pharmaceutical compositions of the invention and instructions for use. Kits of the invention may include one or more of an MCJ agonist compound, which may be used to treat a cancer. Kits containing one or more MCJ agonist compounds can be prepared for treatment methods of the invention. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more components such as one or more MCJ agonist compounds, one or more MCJ polypeptides, one or more MCJ polypeptide encoding polynucleotides, one or more targeting agents, etc.

A kit of the invention may also include instructions. Instructions typically will be in written form and will provide guidance for carrying out the preparation of an MCJ agonist compound of the invention, and/or use of an MCJ agonist compound of the invention in a cancer treatment or assay.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Materials and Methods for Examples

Cell Culture. MCF7 and MCF7/ADR cells were a kind gift from Dr. Ken Cowan (National Cancer Institute, Bethesda, Md.). MCF7/siMCJ cells were generated by stable transfection with a plasmid expressing a shRNA for MCJ (siMCJ) as described in Hatle, K. M., et al., Mol Cell Biol 27, 2952-2966 (2007). All cells were maintained at 37 C, 5% $CO_2$ in RPMI-1640 (Life technologies, Inc., Gaithersburg, Md.) containing 5% FBS.

Mice. MCJ knock out (KO) mice have been previously described in Hatle, K., et al. Mol Cell Biol 33, 2302-2314, (2013). MCJ KO mice were crossed with the previously described MMTV-PyMT mice [see: Guy, C. T., et. al., Mol Cell Biol 12, 954-961 (1992)] to generate MCJ KO MMTV mice. Wildtype MMTV mice and MCJ KO MMTV mice were used for the experiments. All mice were housed under sterile conditions at the animal care facility at the University of Vermont. The procedures were approved by the University of Vermont Institutional Animal Care and Use Committee.

Confocal microscopy for doxorubicin accumulation. MCF7/siMCJ cells were seeded on BD Biocoat coverslips (BD Biosciences, Bedford, Mass.) the day before the treatment. At 20 h, oligomycin (5 µM) or medium was added to the cell. After 3 h, doxorubicin (3 µM) was added and cells were further incubated for 4 h. Cells were washed with PBS and fixed in 3.7% paraformaldehyde. Doxorubicin has an intrinsic fluorescence that can be visualized at the confocal microscope. For nuclear staining, DAPI (Molecular Probes, Eugene, Oreg.) was used. Cells were visualized by confocal microscopy (Zeiss LSM 510 META Confocal Laser Scanning Imaging System, Carl Ziess Microimaging Inc, Thronwood, N.Y.). The term: MCF7/siMCJ and siMCJ/MCF7 is used interchangeably herein.

Bright Field Microscopy. Live cells were imaged at an inverted bright field microscope (Leica Microsystems). 400× magnification was used.

Cell count. Cells were trypsinized, washed, and resuspended in medium. Number of viable cells was measured by counting using Trypan blue dye to exclude dead cells (visualized as blue).

Doxorubicin and peptides treatment in vitro. Doxorubicin (Sigma-Aldrich) was used at 3 µM final concentration. The three different peptides described in the examples (SEQ ID NO: 2, 18 or 6) were resuspended at 10 mM stock concentration in PBS. The peptides were used a different concentration as indicated for each example (1, 10, or 50 µM). Cells were plated the day prior the treatment (18-20 h prior to the treatment). For treatments with peptides only, peptides were added to the plates at the indicated concentrations, and after 2 or 3 days (as indicated for each example) cells were trypsinized, resuspended, and counted. For the treatment with doxorubicin and peptides, cells were pretreated with the corresponding peptide for 4 h prior to adding doxorubicin.

Doxorubicin and peptides treatment in vivo. MTV mice and MCJ KO MMTV mice were used to assay response to doxorubicin and MCJ peptides. The treatments were initiated around 2.5-3 months of age when the mammary tumor these mice develop reach 300 $mm^3$. Doxorubicin was administered intreperitoneal in PBS (100 µl per mouse) at a dose of 2 mg/Kg. TAT-N-MCJ-mts peptide (SEQ ID NO: 6) was administered at the time of doxorubicin by a subcutaneous injection in PBS (100 µl per mouse) at a dose of 10 mg/Kg. Administrations of doxorubicin and peptide were performed every other day for the indicated period of time. Perpendicular tumor diameters were measured using a vernier scale caliper and tumor volume estimated using the formula for ellipsoid (width×high×length)/2.

Complex I activity. Analysis of complex I activity was performed using mitochondrial extracts generated following the protocol for the purification of Complex I (MitoScience). The activity assay using the Complex I Enzyme Activity Microplate assay kit from MitoScience and the protocol recommended by the manufacturer. Mitochondrial extracts (5 µg) from MCF7/siMCJ cells were used for the assay, as described in Hatle, K., et al. Mol Cell Biol 33, 2302-2314, (2013). The N-MCJ peptide (for example, the polypeptide set forth as SEQ ID NO: 28) was added to the extracts at 0 (no peptide), 50 or 100 µM final concentration.

Example 1: Experiments 1 and 2

MCJ has been identified as an endogenous negative regulator of mitochondrial respiratory chain and mitochondria-derived ATP production. Cancer cells mostly use glycolysis as a pathway to generate ATP and rapidly grow, instead of using mitochondria-derived ATP. As a result mitochondria have not been considered a major target for cancer treatment because it was believed that inhibition of mitochondria would increase cancer growth.

A recombinant peptide was generated that contained the N-terminal region of MCJ, a targeting agent, and a mitochondrial-targeting agent. The targeting agent directed the recombinant peptide to penetrate a cancer cell and the mitochondrial-targeting agent directed the recombinant peptide to the mitochondria in the penetrated cell. In this experiment, the targeting agent comprises a TAT-tag, and a mitochondrial targeting signal. The combined recombinant polypeptide acted as an agonist of MCJ function in the mitochondria of the penetrated cell. Treatment of breast cancer cells that do not naturally contain MCJ (do not contain endogenous MCJ polypeptide) with this MCJ recombinant peptide by itself caused death of the cancer cells, demonstrating that the TAT-N-MCJ-MTS polypeptide was a novel therapeutic agent to treat cancers that do not include endogenous MCJ polypeptide.

Experiment 1

MCF7/ADR cells were incubated (using standard procedures) for three days in media alone or in media plus three different MCJ based polypeptides each at a concentration of 50 µM in media. The cells of set one were incubated in media and served as a control set. The cells of set two were incubated in media that included a 50 µM concentration of a MCJ polypeptide without a targeting agent polypeptide. The amino acid sequence of the N-MCJ polypeptide without a targeting agent polypeptide was MAARGVIAPVGESLRYAEYL (SEQ ID NO:2). The cells of set three were incubated in media that included a 50 µM concentration of a TAT-N-MCJ polypeptide. The amino acid sequence of the TAT-N-MCJ polypeptide was: YGKKRRQRRG-MAARGVIAPVGESLRYAEYL (SEQ ID NO:18). The cells of set four were incubated in media that included a 50 µM concentration of a TAT-N-MCJ-MTS polypeptide, which had an amino acid sequence: YGKKRRQRRG-MAARGVIAPVGESLRYAEYLGTRTWVPKGLKSP (SEQ ID NO:6). Results are illustrated in FIG. 1, which shows a graph of the cell number under each condition after the three day incubation. Significantly more cell death occurred in the cell set that was incubated with the TAT-N-MCJ-MTS polypeptide (Set four).

Experiment 2

MCF7 cells and MCF7/ADR cells were incubated (using standard procedures) for two days in media alone or in media that included different concentrations of the TAT-N-MCS-MTS polypeptide having the amino acid sequence set forth as:

```
                                          (SEQ ID NO: 6)
YGKKRRQRRGMAARGVIAPVGESLRYAEYLGTRTWVPKGLKSP.
```

Figure 2A:
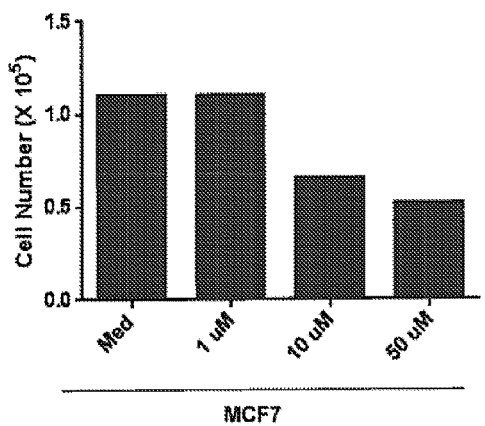
FIG. 2A-B shows two graphs of showing a significantly greater reduction in the cell number when MCF (FIG. 2A) or MCF7/ADR (FIG. 2B) cells were incubated in media that included a 10 μM or a 50 μM concentration of the TAT-N-MCJ-MTS polypeptide (SEQ ID NO:6), than when cells were incubated in media alone, or in 1 μM concentration of the TAT-N-MCJ-MTS polypeptide (SEQ ID NO:6).
Figure 2B:
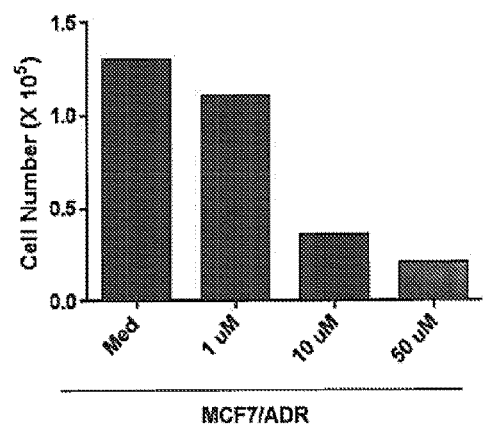
Figure 3:
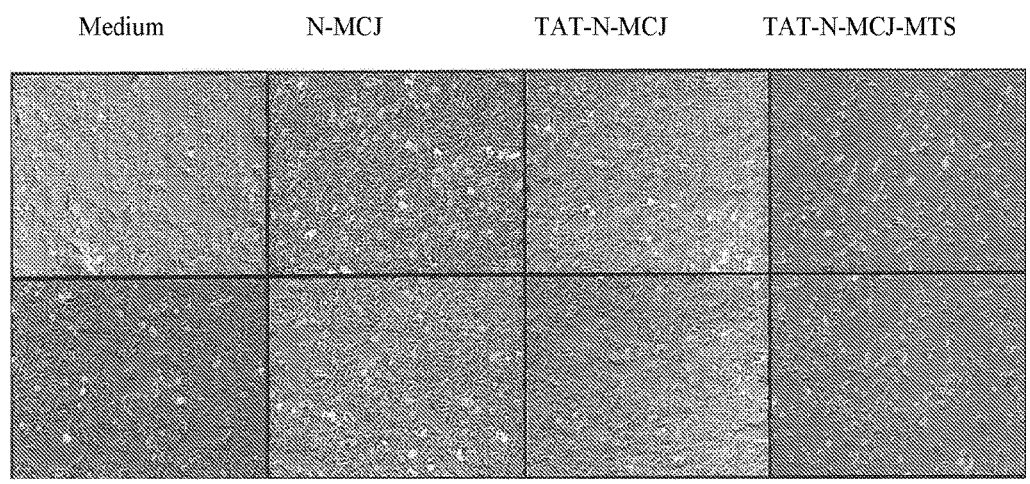
FIG. 3 provides photomicrographic images of MCF7/ADR cells that were incubated for two days in column (1) media alone; column (2) media that included a 50 μM concentration of an N-MCJ polypeptide (SEQ ID NO:2); column (3) media that included a 50 μM concentration of the TAT-N-MCJ polypeptide (SEQ ID NO:18); and column (4) media that included a 50 μM concentration of the TAT-N-MCJ-MTS polypeptide (SEQ ID NO:6).

FIG. 2 shows results of the testing, which showed a significantly greater reduction in the cell number when MCF7 (FIG. 2A) or MCF7/ADR (FIG. 2B) cells were incubated in media that included a 10 µM or a 50 µM concentration of the TAT-N-MCJ-MTS polypeptide, than when cells were incubated in media alone, or in 1 µM concentration of the TAT-N-MCJ-MTS polypeptide. FIG. 3 shows photomicrographic images of MCF7/ADR cells that were incubated for two days in (1) media alone; (2) media that included a 50 µM concentration of the N-MCJ polypeptide set forth as SEQ ID NO:2; (3) media that included a 50 µM concentration of the TAT-N-MCJ polypeptide set forth as SEQ ID NO:18; and (4) media that included a 50 µM concentration of the TAT-N-MCJ-MTS polypeptide set forth as SEQ ID NO:6. FIG. 3 shows two independent images (top and bottom rows) for each culture. The results show that the presence of N-MCJ or TAT-N-MCJ peptides did not affect proliferation of the cells (no difference relative to medium only), but very few cells remain attached to the culture plate when TAT-N-MCJ-MTS peptide was used Example 2: Experiments 3-7

Multidrug resistance of tumors is major problem in the treatment of cancer. A novel strategy to overcome the chemo-resistance of cancer cells to chemotherapeutic drugs has now been identified and tested. A major mechanism of chemoresistance is the presence in the tumor cells of ABC-drug efflux transporters that prevent the accumulation of drugs in the tumor cells. The ABC transporters are highly dependent on ATP. Although cancer cells primarily use glycolysis as a pathway to generate ATP and rapidly grow, mitochondrial-derived ATP has now been identified as a factor in specific localized processes due to the dynamic aspect of mitochondria. It has now been identified that mitochondria contribute to chemoresistance of cancers, a non-limiting example of which is breast cancer, because the cancer cell mitochondria provide increased local levels of ATP that can enhance the activity of ABC-drug efflux transporters. MCJ has now been identified as an endogenous negative regulator of mitochondrial respiratory chain and mitochondria-derived ATP production. The N-terminal region of MCJ is a unique sequence.

Experiments were performed to determine whether one or more N-terminal region MCJ polypeptides can be used as agonist for MCJ function and inhibit mitochondrial-derived ATP and thereby ABC-transporters in cancer cells. The experiments included delivering N-MCJ polypeptides to cells that lack MCJ to determine whether delivery of the polypeptides restored sensitivity of tumor cells to standard chemotherapy. Studies were performed in vitro and in vivo mouse models using a mitochondria-targeted N-MCJ peptide and the results showed that administration of an MCJ agonist polypeptide to a cancer cell increased chemosensensitivity of the cancer cell to a chemotherapeutic agent, doxorubicin. The experiments confirmed that N-MCJ-polypeptides and variants thereof are a novel treatment for breast cancer and other cancers that fail to respond standard chemotherapy.

Experiment 3

Figure 4:
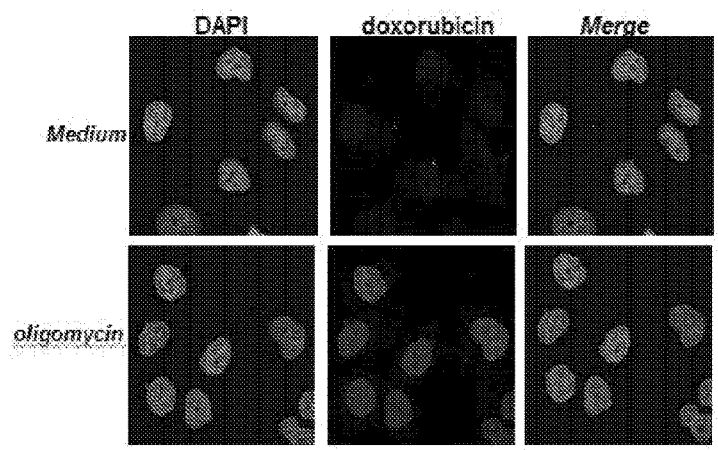
FIG. 4 shows results indicating that reducing mitochondrial respiration in cancer cells restores/increases the cells' sensitivity to chemotherapeutic agents. The confocal microscopy images and analysis showed doxorubicin accumulation only in MCF7/siMCJ cells (where MCJ expression was disrupted by an shRNA for MCJ) that were treated with doxorubicin and oligomycin.

Experiments were performed to determine whether reducing mitochondrial respiration in cancer cells restores the cells' sensitivity to chemotherapeutic agents. Results of the experiments demonstrated that inhibition of mitochondrial respiration restored drug accumulation in cells that were deficient in MCJ. MCF7/siMCJ cells were treated with doxorubicin alone or doxorubicin and oligomycin (an inhibitor of Complex V/ATP synthase) at a concentration of 5 µM for 4 h. Doxorubicin intrinsic fluorescence in the cells was viewed by confocal microscopy. The DAPI dye was used as a nuclear maker. Confocal microscopy analysis showed doxorubicin accumulation (in the nucleus) only in MCF7/siMCJ cells treated with doxorubicin and oligomycin. FIG. 4 shows photomicroscopic images showing DAPI staining alone (blue) to detect the nucleus of the cells (left column), doxorubicin fluorescence alone (red) to detect the intracellular accumulation of doxorubicin (second column), a merge of both DAPI and doxorubicin fluorescence (third column) showing the colocalization of doxorubicin and DAPI (purple color, combination of blue and red).

Experiment 4

Figure 5:
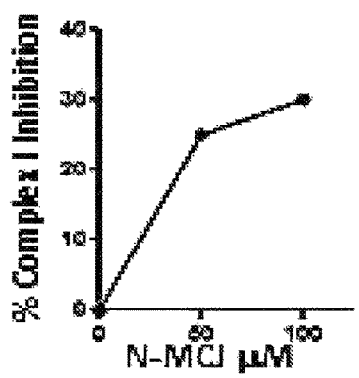
FIG. 5 provides a graph of % Complex I inhibition versus various concentrations of N-MCJ agonist polypeptide (SEQ ID NO:28). The graph illustrates that incubating in vitro mitochondrial extracts from siMCJ/MCF7 cells with different concentrations of an MCJ polypeptide inhibits Complex I activity relative to the activity from extracts without peptide.

MCJ interacts with Complex I of the respiratory chain and is an endogenous inhibitor of Complex I. The region of MCJ that mediates this inhibitory effect has been unknown. Experiments were performed to determine whether an endogenous N-MCJ peptide itself can reproduce this effect. The experiments demonstrated that adding an MCJ polypeptide to mitochondrial extracts generated from siMCJ/MCF7 cells (lacking MCJ) inhibited the in vitro activity of Complex I of the respiratory chain in those extracts, and that the degree of inhibition was dose-dependent. FIG. 5 shows a graph of results of experiments to determine whether an N-MCJ polypeptide at various concentrations could inhibit Complex I activity. Mitochondrial extracts were made from siMCJ/MCF7 cells and were incubated in the presence of various concentrations of the MCJ polypeptide having the amino acid sequence: MAARGVIAPVGESLRYAEYLQPSAK (SEQ ID NO:28) during the Complex I activity assay. The percent inhibition of Complex I activity in extracts from the mitochondria was determined. As indicated in the graph in FIG. 5, the percent of Complex I inhibition increased when incubated with increasing concentrations of the MCJ polypeptide. Inhibition of Complex I results in less ATP production by the mitochondria and increases sensitivity of the cancer cell to chemotherapeutic agents.

Experiment 5

Figure 6:
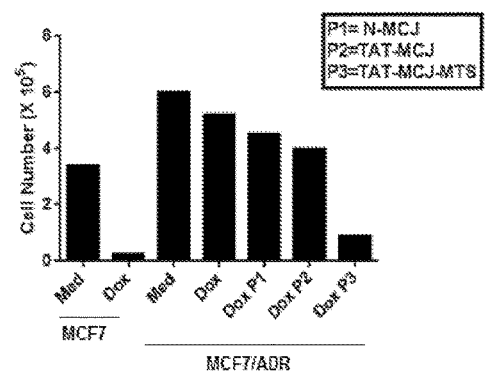
FIG. 6 provides a graph illustrating results obtained incubating MCF7/ADR cells, which lack endogenous MCJ, in media with and without different combinations of the chemotherapeutic agent doxorubicin and three MCJ agonist compounds: P1: N-MCJ, which had the amino acid sequence set forth as SEQ ID NO: 2; P2: TAT-MCJ, which had the amino acid sequence set for as SEQ ID NO:18; and P3: TAT-MCJ-MTS, which had the amino acid sequence set forth as SEQ ID NO:6. The graph also demonstrates results obtained from MCF7 cells that were treated with either media alone or media that included doxorubicin.

The results of the experiments are shown in FIG. 6, which illustrates that in MCF7/ADR cells, which lack endogenous MCJ, incubation of the cell in media that contained a 3 µM concentration of the chemotherapeutic agent doxorubicin, and a 50 µM concentration of a TAT-MCJ-MTS polypeptide (SEQ ID NO:6) resulted in a significantly higher level of cancer cell death than in similar cells that were treated with (1) a 3 µM concentration the chemotherapeutic agent alone;

(2) a 3 µM concentration of the chemotherapeutic agent plus a 50 µM concentration of a TAT-MCJ polypeptide, for example, SEQ ID NO:18; and (3) a 3 µM concentration of the chemotherapeutic agent plus a 50 µM concentration of an N-MCJ polypeptide, for example SEQ ID NO:2 The results also demonstrated that in MCF7 cells, treatment with media that contained a 3 µM concentration of doxorubicin resulted in significant level of cell death compared to MCF7 cells treated with media alone.

Experiment 6

Figure 7:
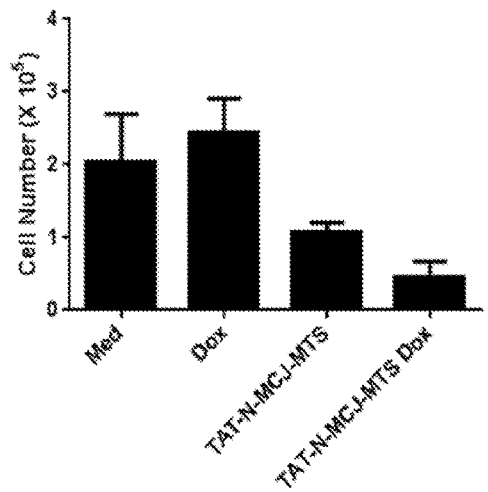
FIG. 7 provides a graph that illustrates results obtained incubating MCF7/ADR cells in media alone [Med], media that contained doxorubicin [Dox]; media that contained a TAT-MCJ-MTS polypeptide having an amino acid sequence of SEQ ID NO:6 [TAT-N-MCJ-MTS]; and media that contained the TAT-N-MCJ-MTS polypeptide (SEQ ID NO:6) and doxorubicin [TAT-N-MCJ-MTS Dox].

The results of the experiments are shown in FIG. 7, which illustrates that in MCF7/ADR cells, which lack endogenous MCJ, incubation of the cell in media that contained a 3 µM concentration of the chemotherapeutic agent doxorubicin, and a 2 µM concentration of a TAT-MCJ-MTS polypeptide (SEQ ID NO:6) resulted in a significantly higher level of cancer cell death than in similar cells that were treated with (1) media only; (2) a 3 µM concentration the chemotherapeutic agent alone. The results showed that contacting MDF7/ADR cells with media that contained a 2 µM concentration of the TAT-N-MCJ-MTS polypeptide (SEQ ID NO:6) without doxorubicin resulted in significantly more cell death than similar cells in (1) media only or (2) a 3 µM concentration the chemotherapeutic agent alone, though the level of cell death with the polypeptide alone was lower than treatment with the MCJ polypeptide (SEQ ID NO:6) and the chemotherapeutic agent.

Experiment 7

Figure 8:
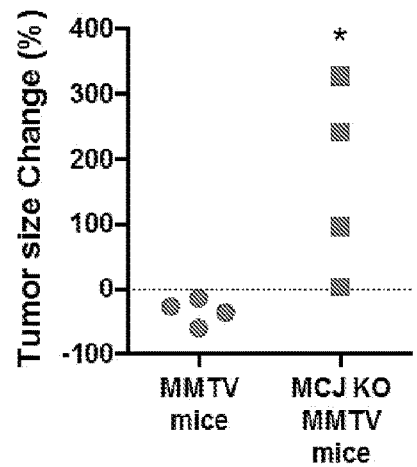
FIG. 8 provides a graph of results that demonstrated that MCJ polypeptide-deficient mammary tumors are resistant to chemotherapy treatment in vivo. MMTV (n=4) and MCJ KO MMTV (n=4) mice were treated with doxorubicin (2 mg/Kg) by i.p. administrations every other day for two weeks and change in tumor size over time was determined. The graph illustrates that the tumor size in MMTV mice decreased over time with the treatment of doxorubicin, while the tumor size in MCJ KO MMTV mice, which were deficient in the endogenous MCJ polypeptide, did not decrease, and continued to increase over time with doxorubicin treatment.

To address whether loss of MCJ can be the cause of chemo-resistance, experiments were performed using a mammary tumor mouse model. Previously generated MCJ knockout mice [Hatle, K. M. et al., (2013) Mol Cell Biol 33:2302-2314] were crossed with MMTV-PyMT transgenic mice that rapidly develop tumors [Guy, C. T. et al., (1992) Mol Cell Biol 12:954-961]. The tumor growth rate was comparable between WT and MCJ KO mice. Both groups of mice were then treated with doxorubicin (a standard chemotherapeutic drug for cancer treatment), and tumor size was followed for 12 days. The size of the tumors in MMTV-Py mice was reduced, but mammary tumors in MCJ KO MMTV-Py mice continued growing or did not shrink (FIG. 8). Thus, demonstrating that loss of MCJ in tumors contributed to a poor chemotherapy response, and supporting increase of MCJ function in methods to overcome chemoresistance.

Results of these experiments demonstrated that MCJ polypeptide-deficient mammary tumors are resistant to chemotherapy treatment in vivo. FIG. 8 shows a graph of results from MMTV (n=4) and MCJ KO MMTV (n=4) mice that were treated with doxorubicin (2 mg/Kg) by i.p. administrations every other day for two weeks. The size of a tumor over time was determined by caliper measurements, and is represented as a percentage relative to the initial size prior to the treatment. $p < 0.05$ as determined by a paired t-test. The results demonstrated that mice that were deficient in endogenous MCJ polypeptide had less reduction in tumor size when treated with the chemotherapeutic agent, doxorubicin.

Figure 9:
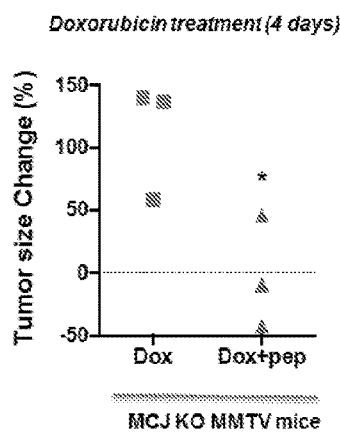
FIG. 9 provides a graph of results from experiments demonstrating that in vivo treatment with a TAT-N-MCJ-MTS polypeptide increased response of MCJ polypeptide deficient mammary tumors to chemotherapy. MCJ KO MMTV mice were treated with doxorubicin alone (Dox) or in combination with the TAT-N-MCJ-MTS polypeptide having the amino acid set forth as SEQ ID NO:6 (Dox+pep).

The experiments in FIG. 9 demonstrated that in vivo treatment with a TAT-N-MCJ-MTS polypeptide increased response of MCJ polypeptide deficient mammary tumors to chemotherapy. MCJ KO MMTV mice were treated with doxorubicin (2 mg/Kg) by i.p. administration alone (Dox) or in combination with the TAT-N-MCJ-MTS polypeptide (Dox+pep) administered s.c. The size of a tumor over time was determined by caliper measurements and the change in tumor size after 4 days of treatment is shown. $p < 0.05$ as determined by a paired t-test. The results shown in FIG. 9 demonstrate that administering to a mouse that has a tumor comprising cancer cells lacking endogenous MCJ polypeptide, an MCJ agonist compound (for example the TAT-N-MCJ-MTS polypeptide having an amino acid sequence YGKKRRQRRGMAARGVIAPVGESLRYAEYLG-TRTWVPKGLKSP (SEQ ID NO:6) and a chemotherapeutic agent such as doxorubicin results in a greater reduction in the tumor size than administering the chemotherapeutic agent to a similar mouse without administering the MCJ agonist compound. The results indicated that the combination treatment with a chemotherapeutic agent and an MCJ agonist compound increased the sensitivity of the cancer cells to the chemotherapeutic agent, and increased cancer cell death compared to treatment with the chemotherapeutic agent alone.

Figure 10:
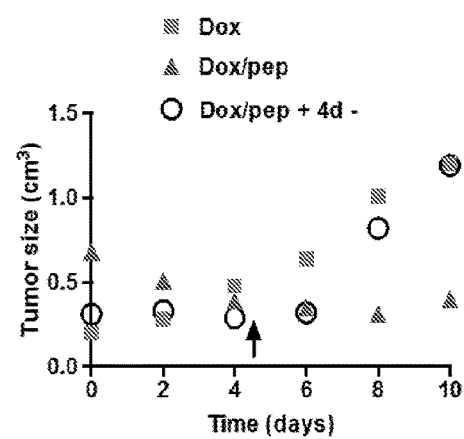
FIG. 10 provides a graph showing results obtained when MCJ KO MMTV mice were treated with a doxorubicin (2 mg/Kg) alone [Dox]; doxorubicin in combination with an MCJ agonist compound: TAT-N-MCJ-MTS polypeptide having an amino acid sequence set forth herein as SEQ ID NO:6 [Dox/pep]; or doxorubicin in combination with the MCJ agonist compound (SEQ ID NO:6) wherein after four days of the dox and MCJ agonist compound treatment, the MCJ compound treatment was stopped and the doxorubicin treatment was continued alone [Dox/pep+4d−].

In further experiments, MCJ KO MMTV mice were treated with a chemotherapeutic agent [doxorubicin (2 mg/Kg)] by i.p. administration alone (Dox) or in combination with an MCJ agonist compound: a TAT-N-MCJ-MTS polypeptide (Dox+pep) administered s.c. In a different situation, after 4 days of treatment with dox and peptide, the peptide treatment stopped while the doxorubicin treatment was continued alone (Dox/pep+4d−). The size of a tumor over time was determined by caliper measurements. Results are shown in FIG. 10, which illustrates that of the three treatments, the most successful at reducing tumor size was treatment with the doxorubicin in combination with the MCJ agonist compound for the full length of the treatment period. The MCJ agonist compound was a TAT-N-MCJ-MTS polypeptide, which has the amino acid sequence:

```
                                          (SEQ ID NO: 6)
YGKKRRQRRGMAARGVIAPVGESLRYAEYLGTRTWVPKGLKSP.
```

Example 3

Role of MCI in Cancer and Chemotherapy Response

Figure 11A:
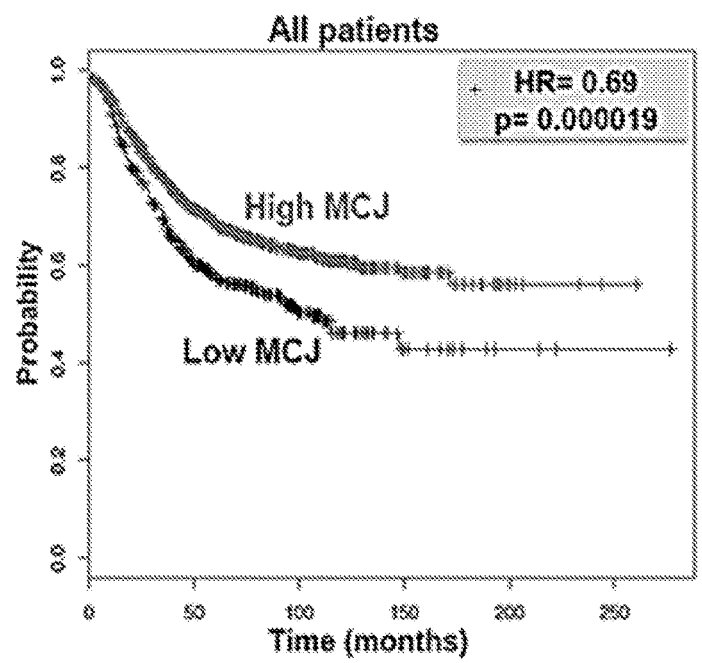
FIG. 11A-D provides Kaplan-Meier curves for relapse free survival (RFS) in breast cancer using the Kaplan-Meier Plotter (kmplot.com) database. "Low MCJ" indicates patients with tumors expressing MCJ in the lowest quartile, while "High MCJ" includes all other patients (MCJ expression in the top 3 quartiles).
Figure 11B:
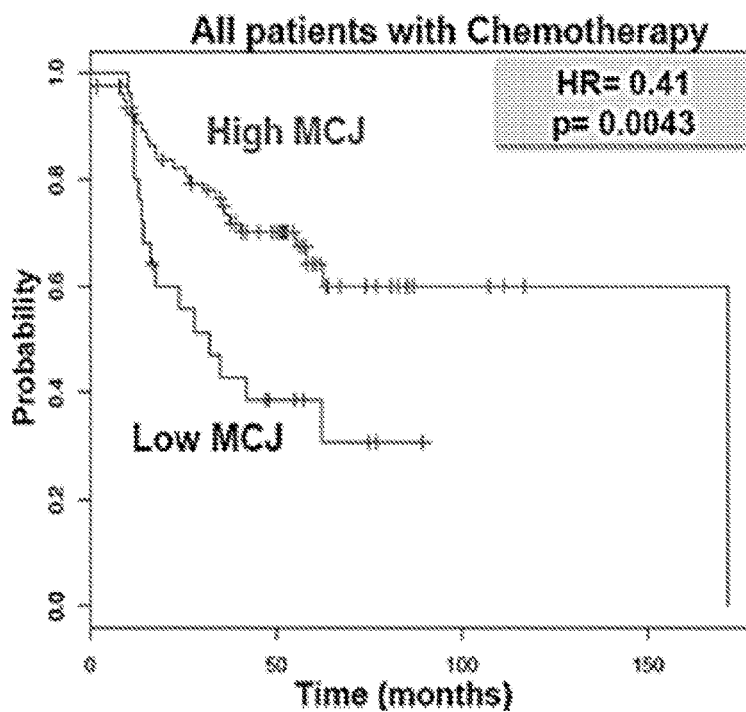
Figure 11:
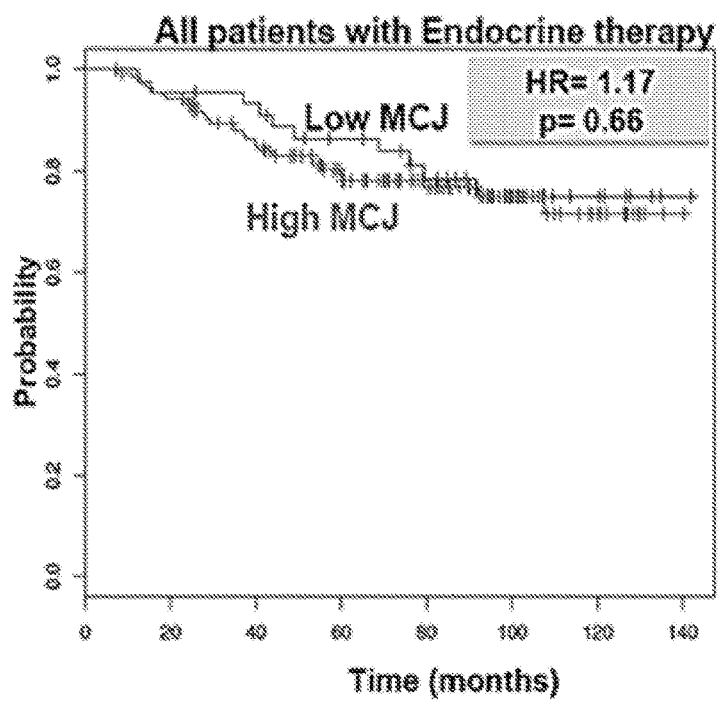
Figure 11D:
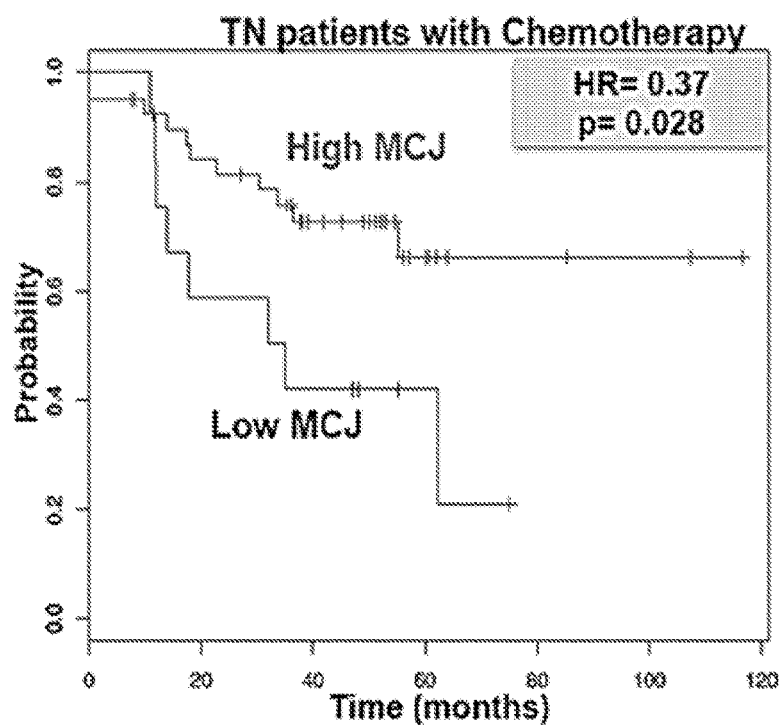

Using the Kaplan-Meier Plotter website that has combined data from three data bases (including TCGA) to examine gene expression in breast cancer, it was identified that patients whose breast cancers express low levels of MCJ exhibit substantially reduced survival relative to those patients whose tumors express higher levels of MCJ (FIG. 11A). The difference in survival was even more striking when the comparison is limited to patients who have received chemotherapy: patients treated with chemotherapy who had breast tumors with low MCJ have shorter survival than those with high MCJ (FIG. 11B). In contrast, there was no difference between low and high MCJ tumor patients when the patients received endocrine therapy (FIG. 11C). Among breast cancer patients, the group defined as "triple negative" (TN), because the lack ER, PR and HerR receptors, presents with the worst prognosis. TN patients cannot be treated with endocrine or Herceptin, leaving chemotherapy as the only option. Although these patients initially respond to chemotherapy well, the tumors relapse very quickly and often become metastatic and refractory to available treatments. Results indicated that there was a higher frequency of patients with low MCJ tumors in the TN group. In addition, survival analysis in the TN group treated with chemotherapy (most of them) indicated that low MCJ expression in the tumor predicted poor survival (FIG. 11D). Together results of these studies indicated that low MCJ expression in primary breast cancer_correlates with poor chemotherapy response of the breast cancer patients. Thus, loss of MCJ expression in tumors for multiple cancers may be used as a biomarker for poor outcome and poor response to chemotherapy.

Example 4

MCJ is an Endogenous Negative Regulator of Mitochondria.

Figure 12A:
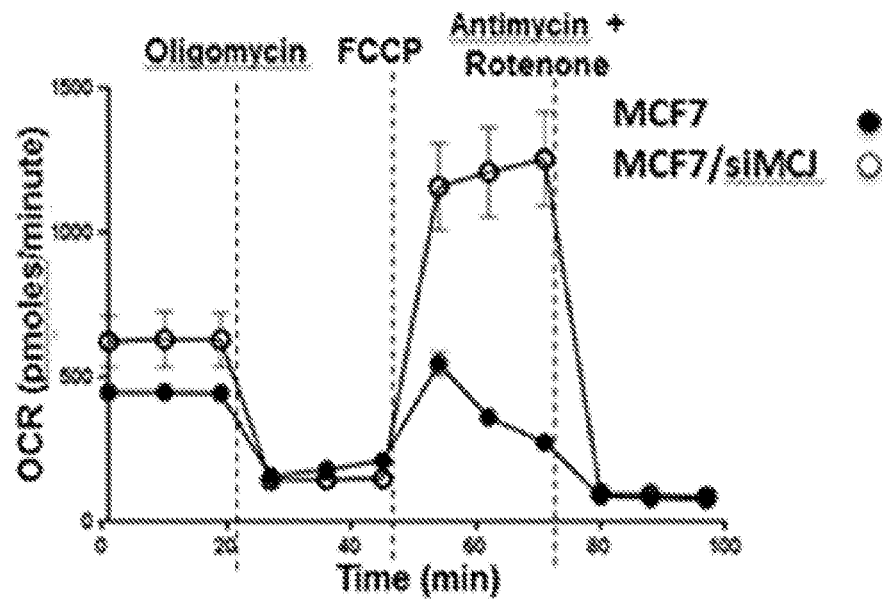
FIG. 12A-B provides graphs of results from MitoStress assays (Seahorse Bioscience, Billerica, Mass.).
Figure 12B:
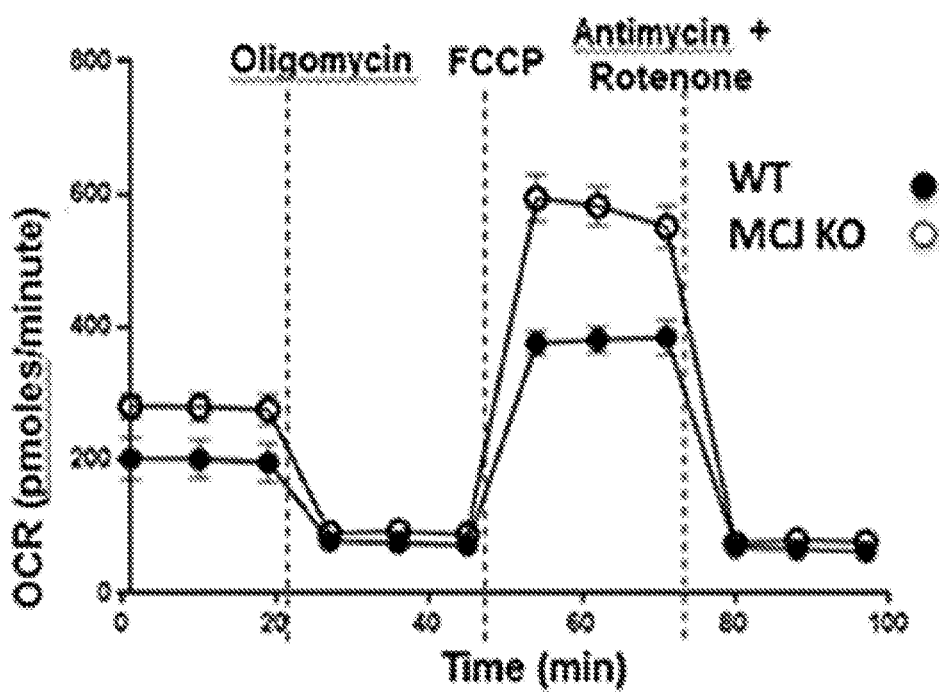

Human breast cancer cell lines MCF7 cells with siRNA-mediated knockdown of MCJ (MCF7/siMCJ cells) have increased Complex I activity. Experiments were performed to examine the effect of MCJ on mitochondrial respiration using the Seahorse X24 analyzer and the MitoStress assay (used in examples herein according to manufacturer's protocols) that measures mitochondrial oxygen consumption rate (OCR), a well-accepted proxy for mitochondrial respiration (Seahorse Bioscience, North Billerica, Mass.). Analysis of mitochondrial respiration in the human breast cancer MCF7 cells (sensitive to chemotherapy and expressing MCJ) and MCF7/siMCJ cells (chemo-resistant and lacking MCJ) showed higher basal OCR in MCF7/siMCJ cells relative to OCR in MCF7 cells (FIG. 12A). In addition, maximum respiratory capacity (determined after addition of the mitochondrial uncoupler FCCP) was also drastically higher in MCF7/siMCJ cells (FIG. 12A). Moreover, Seahorse MitoStress analysis of OCR in primary mammary tumor cells from MMTV-Py mice [Guy, C. T. et al., (1992) Mol Cell Biol 12:954-961] and MCJ KO MMTV-Py mice revealed that, similarly to human MCF7/siMCJ cells, basal OCR and maximum respiratory capacity were higher in MCJ KO tumor cells (FIG. 12B). These results demonstrate that loss of MCJ results in an enhanced mitochondrial respiration in human and mouse cancer cells.

Example 5

MCJ Agonistic Peptides that Restore MCJ Function and Impair Mitochondria Metabolism.

Studies were performed that demonstrated that restoring MCJ function may be used to overcome chemo-resistance in cancer. Deliverable MCJ agonists were developed that could restore MCJ function, reduce mitochondrial metabolism, and overcome cancer chemo-resistance, with minimal toxicity to normal tissues.

Figure 13:
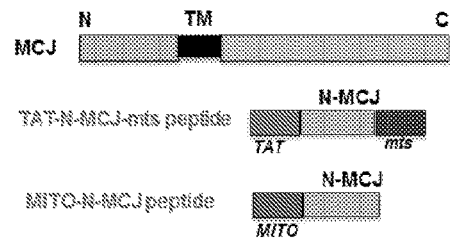
FIG. 13 is a schematic diagram showing an MCJ polypeptide (top); TAT-N-MCJ-mts polypeptide (middle); and MITO-N-MCJ polypeptide (bottom). Certain sequence regions are indicated.

Two different deliverable agonistic N-MCJ peptides (schematic diagram shown in FIG. 13) were developed. The first deliverable agonistic polypeptide is referred to herein as TAT-N-MCJ-mts polypeptide, and has an amino acid sequence set forth herein as SEQ ID NO:6, which includes: a) the HIV transactivator of transcription (TAT) tag (SEQ ID NO: 36 YGKKRRQRR), b) a partial N-MCJ region (20 aa), and c) a mitochondrial targeting sequence (mts) from cytochrome P4501A1 (SEQ ID NO: 37 TRTWVPK-GLKSP), and two glycine "G" spacers inserted between the two targeting tags and the N-MCJ sequence.

The second deliverable agonistic polypeptide is referred to herein as the MITO-N-MCJ peptide and has an amino acid sequence set forth herein as SEQ ID NO: 38 $F_xRF_xK$-$F_xRF_x$KMAARGVIAPVGESLRYAEYL. In SEQ ID NO: 38, the $F_x$ residue is cyclohexylalanine. The MITO-N-MCJ polypeptide comprises the same N-MCJ sequence that was included in the TAT-N-MCJ-mts polypeptide, and b) a "Mitochondrial peptide", also referred to herein as "MITO peptides" a synthetic peptide generated using synthetic amino acids that has been shown to be able to go through the cytoplasmic membrane and result in mitochondrial localization of certain sequences [Horton, K L., et al., (2008) Chemistry & Biology 15:375-382].

Figure 14A:
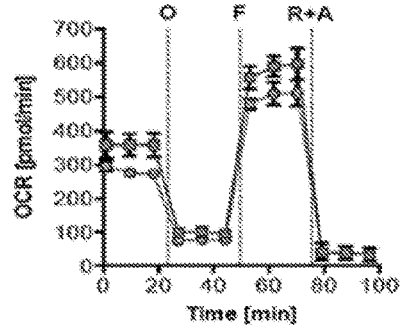
FIG. 14A-C provides graphs showing effect of MCJ agonist polypeptides on OCR and respiratory capacity of cells.
Figure 14B:
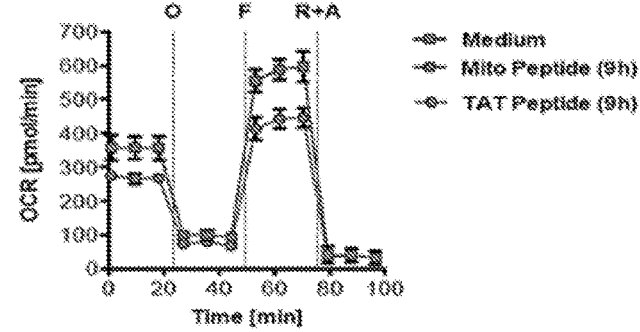

The agonist polypeptides were tested to determine whether they would restore particular MCJ functions and the effect of the agonist polypeptides in mitochondrial respiration was examined. MCF7/ADR cells are multidrug resistant breast cancer cells derived from MCF7 cells. In contrast to MCF7 cell, MCF7/ADR cells totally lack MCJ [see Hatle, K. M., et al., (2007) Mol Cell Biol 27:2952-2966]. Mitochondrial respiration in MCF7/ADR cells is very high compared with that of MCF7 cells. OCR was determined by the Seahorse analyzer in MCF7/ADR cells and MCF7/ADR cells that were pretreated with the TAT-N-MCJ-mts peptide for 9 h. TAT-N-MCJ-mts peptide decreased basal OCR levels as well as maximum respiratory capacity (OCR levels with FCCP) (FIG. 14A). The effect on OCR by the MITO-N-MCJ peptide was even more pronounced (FIG. 14B), and was observed at lower peptide concentrations. These data indicated that the peptide could penetrate cells and, more importantly, reached mitochondria to inhibit respiration. Because the only thing in common between these two peptides is the N-MCJ sequence, these data demonstrated that the effect was specific for the N-MCJ peptide.

Figure 14C:
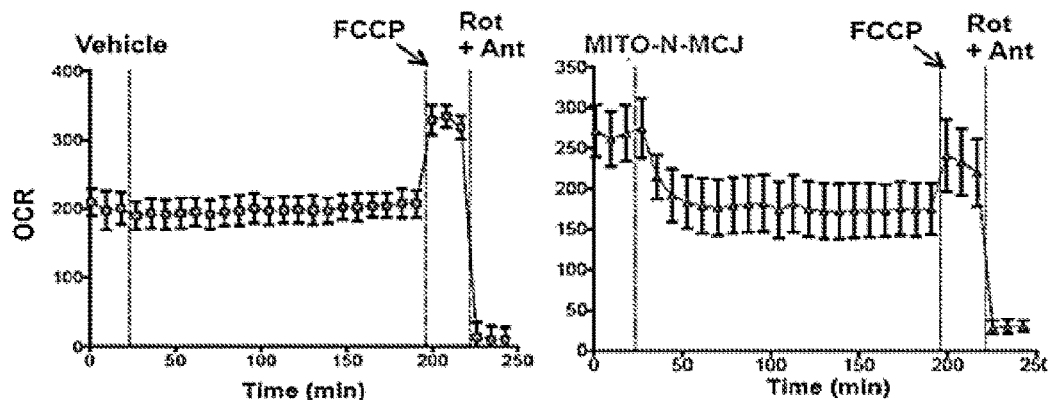

Assays were performed to examine the effect of MITO-N-MCJ peptide on mitochondrial respiration when added directly on cells ongoing Seahorse mito-stress analysis. In this case, OCR was first measured at the basal level and then either vehicle (Seahorse buffer) or the MITO-N-MCJ peptide was added in one of the ports from Seahorse. OCR measurements were then performed during 180 min, followed up by addition of FCCP to determine maximum respiratory capacity and finally Rotenone and antimycin (inhibitors of Complex I and Complex III). The MITO-N-MCJ peptide caused a marked reduction of mitochondrial respiration (FIG. 14C). In addition, compared with cells that were administered with vehicle only, the maximum respiratory capacity (after FCCP) was severely compromised by the addition of the MTIO-N-MCJ peptide (FIG. 14C). The results showed that both of the agonistic MCJ peptides were deliverable, could penetrate cells and reach mitochondria, and that both were effective as inhibitor compounds of mitochondrial respiration.

Example 6

Treatment with MCJ Agonistic Peptides can Overcome Chemoresistance of Breast Cancer Cells.

As described elsewhere herein, MCF7/ADR cells are resistant to a broad spectrum of chemotherapeutic drugs including doxorubicin, paclitaxel, vincristine among others. Notably, contrasting with parental MCF7 cells, they totally lack MCJ expression (FIG. 15A), and they are more dependent on mitochondria for proliferation [see Alakhova, E. Y., et al., (2010) J. Control Release 142:89-100]. Although doxorubicin had no effect on the expansion of MCF7/ADR cells (FIG. 15B), both the TAT-N-MCJ-mts and MITO-N-MCJ peptides by themselves, had a drastic effect in limiting the expansion of these resistant cells (FIG. 15B). The experimental results indicated that the efficacy of the MITO-N-MCJ peptide was greater (2-3 times) than the efficacy of the TAT-N-MCJ peptide. A control TAT-N-MCJ peptide lacking the "mts" had no effect. In contrast to the effect on MCF7/ADR cells, neither of the two MCJ agonists had an effect on MCF7 cells (FIG. 15C), even though these cells were sensitive to doxorubicin (FIG. 15C). These results showed that the two MCJ agonists by themselves could block proliferation of multidrug resistant breast cancer cells, and showed greater efficacy than standard chemotherapy. In addition, because these MCJ agonists did not affect MCF7 cells that already maintain MCJ expression, the results indicated that the effect on MCF7/ADR cells was not the result of a global toxicity, but a specific effect mediated by restoration of MCJ activity in these cells. MCF7/ADR cells have evolved to have low MCJ expression as a mechanism for drug resistance.

To determine whether the MCJ agonists could also synergize with standard chemotherapy in multidrug resistant breast cancer cells experiments were performed that tested the effect of the TAT-N-MCJ-mts peptide at a lower dose (10 times lower) that by itself did not impact cell viability. MCF7/ADR cells were treated with doxorubicin, TAT-N-MCJ-mts peptide alone or in combination. The TAT-N-MCJ-mts peptide by itself did not have a significant effect, but it clearly increased the response to doxorubicin (see FIG. 16A). Thus, at lower doses, MCJ agonists could overcome chemo-resistance of breast cancer cells in vitro. A study was also performed that tested the effect of the TAT-N-MCJ-mts peptide in combination with chemotherapy in vivo using the MMTV mammary tumor mouse model. As noted elsewhere herein, tumors lacking MCJ in the MCJ KO MMTV mice do not respond or respond poorly to doxorubicin treatment. Therefore MCJ KO MMTV mice were treated with doxorubicin alone or doxorubicin and the TAT-N-MCJ-mts peptide and followed tumor size. Tumors from MCJ KO mice treated with doxorubicin alone continued growing, but there was a regression or retarded growth in tumors from mice treated with doxorubicin and peptide (see FIG. 16B). These results supported a conclusion that MCJ agonists can enhance the response to chemotherapy of chemo-resistant tumors in vivo. These results also suggested that administration of the MCJ agonists does not cause much toxicity in vivo because no obvious abnormality was observed in these treated mice.

Example 7

Therapeutic Effect of MCJ Agonists on AML.

Figure 17A:
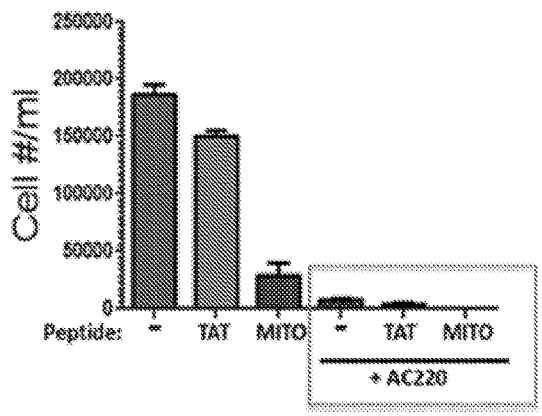
FIG. 17A-D provides graphs of results showing MCJ agonist inhibition of AML.
Figure 17B:
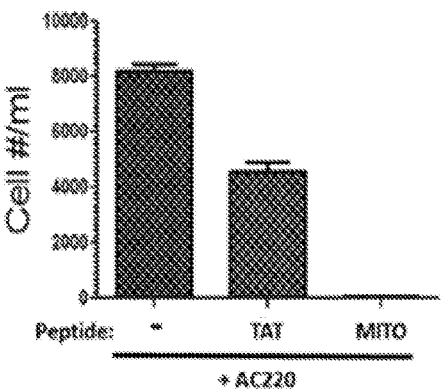

Acute myeloid leukemia (AML) is the most common adult acute leukemia and comprises 20% of childhood leukemia. Although frontline treatment of AML with cytotoxic chemotherapy achieves high remission rates, 75-80% of patients will either not respond or will relapse after initial therapy, and most patients will die of their disease [see: Stone, R. M., et al., (2004) Hematology Am soc Hematol Edu Program, pp 98-117]. Although responses are better for children with AML, cure rates remain unacceptably low (<60%) and current therapies exert a heavy toll on the patients, with substantial immediate and long-term side effects. Experiments were performed to assess the therapeutic potential of administering MCJ agonists to restore MCJ as a treatment in AML. It was found that Molm13 and Mv411 AML cells totally lack MCJ expression. Molm13 AML cells were treated with either of the two MCJ agonists, the Flt3 inhibitor AC220 or a combination of AC220 with our MCJ agonists. After three days of treatment, viability was determined. The MITO-N-MCJ agonist had a profound effect on Molm13 cells, leading to substantial cell death (see for example, FIG. 17A). The TAT-N-MCJ-mts also had more modest effects alone (FIG. 17A). AC220 was effective at inducing Molm13 cell death (due to their Flt3 mutation), but there was a fraction of cells refractory to AC220 that remained alive (FIGS. 17A and 17B), and it is believed that this refractory subpopulation may be responsible for the relapse of the disease in AML patients [see Alverez-Calderon, M. A., et al., (2015) Clin Cancer Res 21:1360-1372]. The experimental results indicated that the combination of AC220 with MCJ agonists effectively eliminated this resistant group (FIG. 17B), particularly for MITO-N-MCJ. Similar results were obtained with a second Flt3 mutant AML, Mv411 (data not shown).

Figure 17C:
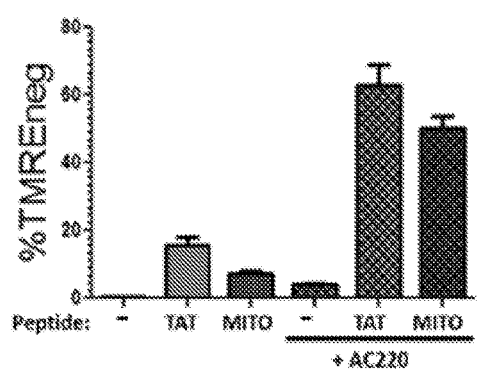
Figure 17D:
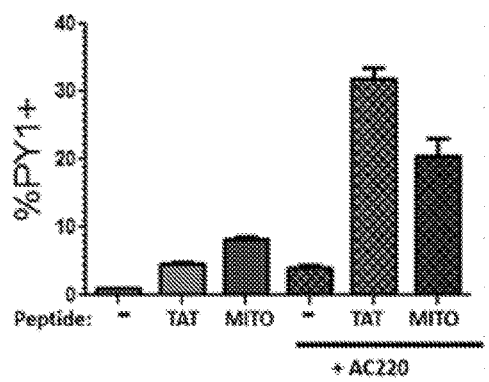

Experiments were also performed to assess the effect of MCJ agonists on mitochondrial membrane potential by staining with the TMRE dye. Given the more modest effects observed for TAT-N-MCJ-mts (FIG. 17A-B), 50 µM of this peptide was used in the experiments. After 22 h of treatment, both MCJ agonistic peptides caused a loss of mitochondrial membrane potential (TMRE negative cells) in a fraction of Molm13 cells (FIG. 17C). However, the most remarkable effect was obtained by treatment of cells with AC220 in combination with either of the two MCJ agonists (FIG. 17C). AML cells are sensitive to the levels of reactive oxygen species (ROS), which are primarily generated in mitochondria as a result of electron leakage from the ETC. It was previously shown that MCJ can interfere with the formation of ETC respiratory supercomplexes [Hatle, K., et al., (2013) Mol Cell boil 33:2302-2314] that are formed to facilitate electron transport between complexes and minimize electron leakage [see Acin-Perez, R. et al., (2008) Mol Cell 32:529-539 and Lapuente-Brun, E. et al., (2013) Science 340:1567-1570]. Analysis of mitochondrial ROS (mROS) levels by staining with PY1 dye, showed that both MCJ agonists could induce the production of mROS by 22 h of treatment (FIG. 17D), and that they clearly synergized with AC220 to cause a massive production of mROS (FIG. 17D). The effect of the MCJ agonists was already observed after 5 h of treatment. Thus, the MCJ agonists, MITO-N-MCJ and TAT-N-MCJ-mts peptides, may be used therapeutically to treat AML when MCJ is lost by the malignant cells, and can be used synergistically in combination with the Flt3 inhibitors currently in clinical trials. The combination of MCJ agonists and the Flt3 inhibitors may prevent or delay the AML relapse.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

What is claimed is:

1. A method of increasing a chemo-sensitivity of a cancer cell, the method comprising, contacting a cancer cell with one or more exogenous MCJ agonist compounds in an amount effective to increase sensitivity of the cancer cell to one or more chemotherapeutic agents, wherein the exogenous MCJ agonist compound comprises an MCJ molecule and the exogenous MCJ agonist compound further comprises one or more targeting agents.

2. The method of claim 1, wherein the exogenous MCJ agonist compound comprises one or more mitochondrial-targeting agents.

3. The method of claim 2, wherein the one or more mitochondrial-targeting agents is a polypeptide, and optionally comprises the amino acid sequence set forth as GTRTWVPKGLKSP (SEQ ID NO: 10), or a variant thereof.

4. The method of claim 1, wherein the cancer cell is a vertebrate cancer cell, and optionally is a mammalian cancer cell.

5. The method of claim 1, wherein the cancer cell is in a subject.

6. The method of claim 1, further comprising contacting the cancer cell with one or more chemotherapeutic agents.

7. The method of claim 1, wherein the MCJ molecule is an MCJ polypeptide and the MCJ polypeptide comprises one or more acetylated amino acid residues.

8. A method of treating a cancer in one or more cells, the method comprising,
contacting one or more cancer cells with an effective amount of at least one exogenous MCJ agonist compound to treat the cancer in the one or more cancer cells, wherein the exogenous MCJ agonist compound comprises an MCJ molecule and one or more targeting agents.

9. The method of claim 8, wherein the exogenous MCJ agonist compound comprises one or more mitochondrial-targeting agents.

10. The method of claim 8, wherein the one or more cancer cells is a vertebrate cancer cell, and optionally is a mammalian cancer cell.

11. The method of claim 8, wherein the one or more cancer cells is in a subject.

12. The method of claim 8, further comprising contacting the one or more cancer cells with an effective amount of one or more chemotherapeutic agents.

13. A composition comprising an exogenous MCJ agonist compound that comprises an MCJ molecule, a targeting agent, and optionally, a cell internalization agent, wherein the MCJ molecule is an MCJ polypeptide.

14. The composition of claim 13, wherein the cell internalization agent comprises a TAT polypeptide sequence, and optionally comprises a TAT polypeptide sequence set forth as YGKKRRQRRG (SEQ ID NO: 9), or a variant thereof.

15. The composition of claim 13, wherein the exogenous MCJ agonist compound comprises one or more mitochondrial-targeting agents, and optionally at least one of the mitochondrial-targeting agent is a polypeptide, and optionally the polypeptide comprises the amino acid sequence set forth as GTRTWVPKGLKSP (SEQ ID NO: 10), or a variant thereof.

16. The composition of claim 15, wherein the mitochondrial-targeting agent is a peptide comprising the amino acid sequence set forth as $F_xRF_xKF_xRF_xK$ (SEQ ID NO: 39), or a variant thereof.

17. The composition of claim 13, wherein the MCJ polypeptide comprises a sequence set forth as MAARGVIAPVGESLRYAEYLQPSAKRPDADVDQQRLVRSL (SEQ ID NO: 1), MAARGVIAPVGESLRYAEYL (SEQ ID NO: 2), VIAPVGESL (SEQ ID NO: 3), VGESLRYAEY (SEQ ID NO: 4), MAARGVIAPVGESLRYAEYLQPSAK*RPDADVDQQRLVRSL (SEQ ID NO: 5), or a variant thereof.

18. The composition of claim 13, wherein the MCJ polypeptide comprises one or more acetylated amino acid residues, and wherein one of the acetylated amino residues is a lysine (K) residue that corresponds to the K25 position in the sequence set forth as SEQ ID NO: 1 when the amino acid sequence of the MCJ polypeptide is aligned with the amino acid sequence set forth as SEQ ID NO: 1.

19. The composition of claim 13, wherein the composition is a pharmaceutical composition comprises and a pharmaceutically acceptable carrier.

* * * * *

SEQUENCE LISTING

```
<160> NUMBER OF SEQ ID NOS: 39

<210> SEQ ID NO 1
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 1

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Arg Leu Val Arg Ser Leu
        35                  40

<210> SEQ ID NO 2
<211> LENGTH: 20
<212> TYPE: PRT
<213> ORGANISM: Homo sapiens

<400> SEQUENCE: 2

Met Ala Ala Arg Gly Val Ile Ala Pro Val Gly Glu Ser Leu Arg Tyr
1               5                   10                  15

Ala Glu Tyr Leu
            20

<210> SEQ ID NO 3
<211> LENGTH: 9
<212> TYPE: PRT
<213> ORGANISM: Homo sapiens

<400> SEQUENCE: 3

Val Ile Ala Pro Val Gly Glu Ser Leu
1               5

<210> SEQ ID NO 4
<211> LENGTH: 10
<212> TYPE: PRT
<213> ORGANISM: Homo sapiens

<400> SEQUENCE: 4

Val Gly Glu Ser Leu Arg Tyr Ala Glu Tyr
1               5                   10

<210> SEQ ID NO 5
<211> LENGTH: 40
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<222> LOCATION: (25)..(25)
<223> OTHER INFORMATION: Lysine is acetylated

<400> SEQUENCE: 5
```

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Arg Leu Val Arg Ser Leu
        35                  40

```
<210> SEQ ID NO 6
<211> LENGTH: 43
<212> TYPE: PRT
<213> ORGANISM: Artificial Sequence
<220> FEATURE:
<223> OTHER INFORMATION: Synthetic Polypeptide

<400> SEQUENCE: 6
```

Tyr Gly Lys Lys Arg Arg Gln Arg Arg Gly Met Ala Ala Arg Gly Val
1               5                   10                  15

Ile Ala Pro Val Gly Glu Ser Leu Arg Tyr Ala Glu Tyr Leu Gly Thr
            20                  25                  30

Arg Thr Trp Val Pro Lys Gly Leu Lys Ser Pro
        35                  40

```
<210> SEQ ID NO 7
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 7
```

Tyr Gly Lys Lys Arg Arg Gln Arg Arg Gly Val Ile Ala Pro Val Gly
1               5                   10                  15

Glu Ser Leu Gly Thr Arg Thr Trp Val Pro Lys Gly Leu Lys Ser Pro
            20                  25                  30

```
<210> SEQ ID NO 8
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 8
```

Tyr Gly Lys Lys Arg Arg Gln Arg Arg Gly Val Gly Glu Ser Leu Arg
1               5                   10                  15

Tyr Ala Glu Tyr Gly Thr Arg Thr Trp Val Pro Lys Gly Leu Lys Ser
            20                  25                  30

Pro

```
<210> SEQ ID NO 9
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 9
```

Tyr Gly Lys Lys Arg Gln Arg Arg Gly
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 10

Gly Thr Arg Thr Trp Val Pro Lys Gly Leu Lys Ser Pro
1               5                   10

<210> SEQ ID NO 11
<211> LENGTH: 150
<212> TYPE: PRT
<213> ORGANISM: Homo sapiens

<400> SEQUENCE: 11

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Gly Leu Val Arg Ser Leu Ile Ala Val Gly Leu Gly Val Ala
        35                  40                  45

Ala Leu Ala Phe Ala Gly Arg Tyr Ala Phe Arg Ile Trp Lys Pro Leu
    50                  55                  60

Glu Gln Val Ile Thr Glu Thr Ala Lys Lys Ile Ser Thr Pro Ser Phe
65                  70                  75                  80

Ser Ser Tyr Tyr Lys Gly Gly Phe Glu Gln Lys Met Ser Arg Arg Glu
                85                  90                  95

Ala Gly Leu Ile Leu Gly Val Ser Pro Ser Ala Gly Lys Ala Lys Ile
            100                 105                 110

Arg Thr Ala His Arg Arg Val Met Ile Leu Asn His Pro Asp Lys Gly
        115                 120                 125

Gly Ser Pro Tyr Val Ala Ala Lys Ile Asn Glu Ala Lys Asp Leu Leu
    130                 135                 140

Glu Thr Thr Thr Lys His
145                 150

<210> SEQ ID NO 12
<211> LENGTH: 1074
<212> TYPE: DNA
<213> ORGANISM: Homo sapiens

<400> SEQUENCE: 12
ggtcaggaaa gctcaggcaa gcccaccctc aggcattaca gctagactcc gagcttactg    60
ggcagtcatc tgattcgacc aacatcagtt cgcagggctt aagcccagtc ccttacggcg   120
gctggggagg gaccaggccc aagtatataa agctccctga gggtccgcgt tggctttgcg   180
cctgtgagtg tgattcaaga acgtcccagt gcccttggct cctttcggag tgtgaccccg   240
tgcttgcacg ggacacgtta cccagctcgg gtgagaaggg tatcttccgg gaacctcgcc   300
tttaatagca caacgagcgc agagtccact ggatctgcga agaaaaccg cgctaactag    360 tttgtcccta cggccgcctc gtagtcactg ccgcggcgcc ttgagtctcc gggccgcctt   420
gccatggctg cccgtggtgt catcgctcca gttggcgaga gtttgcgcta cgctgagtac   480

-continued

```
ttgcagccct cggccaaacg gccagacgcc gacgtcgacc agcagggact ggtaagaagt    540
ttgatagctg taggactggg tgttgcagct cttgcatttg caggtcgcta cgcatttcgg    600
atctggaaac tctagaaca agttatcaca gaaactgcaa agaagatttc aactcctagc    660
ttttcatcct actataaagg aggatttgaa cagaaaatga gtaggcgaga agctggtctt    720
attttaggtg taagcccatc tgctggcaag gctaagatta aacagctca taggagagtc     780 atgattttga atcacccaga taaaggtgga tctccttacg tagcagccaa aataaatgaa    840
gcaaaagact tgctagaaac aaccaccaaa cattgatgct taaggaccac actgaaggaa    900
aaaaaaagag gggacttcga aaaaaaaaaa agccctgcaa aatattctaa acatggtct     960 tcttaatttt ctatatggat tgaccacagt cttatcttcc accattaagc tgtataacaa   1020
taaaatgtta atagtcttgc tttttattat cttttaaaga tctccttaaa ttct         1074
```

<210> SEQ ID NO 13
<211> LENGTH: 149
<212> TYPE: PRT
<213> ORGANISM: Mus musculus

<400> SEQUENCE: 13

Met Ala Thr Gly Gly Val Thr Ser Arg Glu Ser Leu Arg Tyr Ala
1               5                   10                  15

Glu Tyr Leu Pro Pro Ser Ala Gln Arg Ser Asp Ala Asp Ile Asp His
            20                  25                  30

Thr Ala Gly Arg Arg Leu Ile Ala Val Gly Leu Gly Val Ala Ala Val
        35                  40                  45

Ala Phe Ala Gly Arg Tyr Ala Phe Gln Ile Trp Lys Pro Leu Glu Gln
    50                  55                  60

Val Ile Thr Ala Thr Ala Arg Lys Ile Ser Ser Pro Ser Phe Ser Ser
65                  70                  75                  80

Tyr Tyr Lys Gly Gly Phe Glu Gln Lys Met Ser Lys Arg Glu Ala Ser
                85                  90                  95

Leu Ile Leu Gly Val Ser Pro Ser Ala Gly Lys Ala Lys Ile Arg Thr
            100                 105                 110

Ala His Lys Arg Ile Met Ile Leu Asn His Pro Asp Lys Gly Gly Ser
        115                 120                 125

Pro Tyr Val Ala Ser Lys Ile Asn Glu Ala Lys Asp Leu Leu Glu Ala
    130                 135                 140

Ser Ser Lys Ala Asn
145

<210> SEQ ID NO 14
<211> LENGTH: 150
<212> TYPE: PRT
<213> ORGANISM: Homo sapiens

<400> SEQUENCE: 14

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Arg Leu Val Arg Ser Leu Ile Ala Val Gly Leu Gly Val Ala
        35                  40                  45

Ala Leu Ala Phe Ala Gly Arg Tyr Ala Phe Arg Ile Trp Lys Pro Leu
    50                  55                  60

Glu Gln Val Ile Thr Glu Thr Ala Lys Lys Ile Ser Thr Pro Ser Phe

| | | | | 65 | | | | 70 | | | | 75 | | | | 80 | |
|---|---|---|---|---|---|---|---|---|---|---|---|---|---|---|---|---|---|
| Ser | Ser | Tyr | Tyr | Lys | Gly | Gly | Phe | Glu | Gln | Lys | Met | Ser | Arg | Arg | Glu | | |
| | | | | | | 85 | | | | | 90 | | | | | 95 | |
| Ala | Gly | Leu | Ile | Leu | Gly | Val | Ser | Pro | Ser | Ala | Gly | Lys | Ala | Lys | Ile | | |
| | | | | 100 | | | | | 105 | | | | | 110 | | | |
| Arg | Thr | Ala | His | Arg | Arg | Val | Met | Ile | Leu | Asn | His | Pro | Asp | Lys | Gly | | |
| | | | | 115 | | | | | 120 | | | | | 125 | | | |
| Gly | Ser | Pro | Tyr | Val | Ala | Ala | Lys | Ile | Asn | Glu | Ala | Lys | Asp | Leu | Leu | | |
| | | 130 | | | | | 135 | | | | | 140 | | | | | |
| Glu | Thr | Thr | Thr | Lys | His | | | | | | | | | | | | |
| 145 | | | | | 150 | | | | | | | | | | | | |

<210> SEQ ID NO 15
<211> LENGTH: 2404
<212> TYPE: DNA
<213> ORGANISM: Homo sapien

<400> SEQUENCE: 15

| | |
|---|---|
| agtctccggg ccgccttgcc atggctgccc gtggtgtcat cgctccagtt ggcgagagtt | 60 |
| tgcgctacgc tgagtacttg cagccctcgg ccaaacggcc agacgccgac gtcgaccagc | 120 |
| agagactggt aagaagtttg atagctgtag gcctgggtgt tgcagctctt gcatttgcag | 180 |
| gtcgctacgc atttcggatc tggaaacctc tagaacaagt tatcacagaa actgcaaaga | 240 |
| agatttcaac tcctagcttt tcatcctact ataaggagg atttgaacag aaaatgagta | 300 |
| ggcgagaagc tggtcttatt ttaggtgtaa gcccatctgc tggcaaggct aagattagaa | 360 |
| cagctcatag gagagtcatg attttgaatc acccagataa aggtggatct ccttacgtag | 420 |
| cagccaaaat aaatgaagca aaagacttgc tagaaacaac caccaaacat tgatgcttaa | 480 |
| ggaccacact gaaggaaaaa aaaagagggg acttcaaaaa aaaaaaaaaa gccctgcaaa | 540 |
| atattctaaa acatggtctt cttaattttc tatatggatt gaccacagtc ttatcttcca | 600 |
| ccattaagct gtataacaat aaaatgttaa tagtcttgct ttttattatc ttttaaagat | 660 |
| ctccttaaat tctataactg atcttttttc ttattttgtt tgtgacattc atacattttt | 720 |
| aagatttttg ttatgttctg aattcccccc tacacacaca cacacacaca cacacacaca | 780 |
| cgtgcaaaaa atatgatcaa gaatgcaatt gggatttgtg agcaatgagt agacctctta | 840 |
| ttgtttatat ttgtaccctc attgtcaatt ttttttttagg gaatttggga ctctgcctat | 900 |
| ataaggtgtt ttaaatgtct tgagaacaag cactggctga tacctcttgg agatatgatc | 960 |
| tgaaatgtaa tggaatttat taaatggtgt ttagtaaagt aggggttaag gacttgttaa | 1020 |
| agaaccccac tatctctgag accctatagc caaagcatga ggacttggag agctactaaa | 1080 |
| atgattcagg tttacaaaat gagccctgtg aggaaaggtt gagagaagtc tgaggagttt | 1140 |
| gtatttaatt atagtcttcc agtactgtat attcattcat tactcattct acaaatattt | 1200 |
| attgacccct tttgatgtgc aaggcactat cgtgcgtccc ctgagagttg caagtatgaa | 1260 |
| gcagtcatgg atcatgaacc aaaggaactt atatgtagag aaggataaa tcacaaatag | 1320 |
| tgaatactgt tagatacaga tgatatattt taaaagttca aaggaagaaa agaatgtgtt | 1380 |
| aaacactgca tgagaggagg aataagtggc atagagctag ctttagaaa agaaaaatat | 1440 |
| tccgatacca tatgattggt gaggtaagtg ttattctgag atgagaatta gcagaaatag | 1500 |
| atatatcaat cggagtgatt agagtgcagg gtttctggaa agcaaggttt ggacagagtg | 1560 |
| gtcatcaaag gccagccctg tgacttacac tgcattaaat taatttctta gaacatagtc | 1620 |

```
cctgatcatt atcactttac tattccaaag gtgagagaac agattcagat agagtgccag    1680
cattgtttcc cagtattcct ttacaaatct tgggttcatt ccaggtaaac tgaactactg    1740
cattgtttct atcttaaaat acttttaga tatcctagat gcatctttca acttctaaca    1800
ttctgtagtt taggagttct caaccttggc attattgaca tgttaggcca ataattttt    1860 tttgtgggag gtctcttgtg cgttttagat gattagcaat aatccctgac ctgttatcta    1920
ctaaagacta gtcgtttctc atcagttgtg acaacaaaaa tggttccaga tattgccaaa    1980 tgcccttag aggacagtaa tcgcccccag ttgagaacca tttcagtaaa actttaatta    2040 ctatttttc ttttggttta taaaataatg atcctgaatt aaattgatgg aaccttgaag    2100
tcgataaaat atatttcttg ctttaaagtc cccatacgtg tcctactaat tttctcatgc    2160
tttagtgttt tcacttttct cctgttatcc ttgtacctaa gaatgccatc ccaatcccca    2220
gatgtccacc tgcccaaagt ctaggcatag ctgaaggcca agctaaaatg tatccctctt    2280
tttctggtac atgcagcaaa agtaatatga attatcagct ttctgagagc aggcattgta    2340
tctgtcttgt ttggtgttac attggcaccc aataaatatt tgttgagcga aaaaaaaaa    2400 aaaa                                                                 2404

<210> SEQ ID NO 16
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 16

Met Ala Ala Arg Gly Val Ile Ala Pro Val Gly Glu Ser Leu Arg Tyr
1               5                   10                  15

Ala Glu Tyr Leu Cys
            20

<210> SEQ ID NO 17
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 17

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Arg Leu Val Arg
        35

<210> SEQ ID NO 18
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 18

Tyr Gly Lys Lys Arg Arg Gln Arg Arg Gly Met Ala Ala Arg Gly Val
1               5                   10                  15

Ile Ala Pro Val Gly Glu Ser Leu Arg Tyr Ala Glu Tyr Leu
            20                  25                  30
```

<210> SEQ ID NO 19
<211> LENGTH: 29
<212> TYPE: PRT
<213> ORGANISM: Homo sapiens

<400> SEQUENCE: 19

Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala
            20                  25

<210> SEQ ID NO 20
<211> LENGTH: 24
<212> TYPE: PRT
<213> ORGANISM: Homo sapiens

<400> SEQUENCE: 20

Met Ala Ala Arg Gly Val Ile Ala Pro Val Gly Glu Ser Leu Arg Tyr
1               5                   10                  15

Ala Glu Tyr Leu Gln Pro Ser Ala
            20

<210> SEQ ID NO 21
<211> LENGTH: 18
<212> TYPE: PRT
<213> ORGANISM: Homo sapiens

<400> SEQUENCE: 21

Met Ala Ala Arg Gly Val Ile Ala Pro Val Gly Glu Ser Leu Arg Tyr
1               5                   10                  15

Ala Glu

<210> SEQ ID NO 22
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 22

Arg Gly Val Ile Ala Pro Val Gly Glu Ser Leu Arg Tyr Ala Glu Tyr
1               5                   10                  15

Leu Cys

<210> SEQ ID NO 23
<211> LENGTH: 19
<212> TYPE: PRT
<213> ORGANISM: Homo sapiens

<400> SEQUENCE: 23

Ala Ala Arg Gly Val Ile Ala Pro Val Gly Glu Ser Leu Arg Tyr Ala
1               5                   10                  15

Glu Tyr Leu

<210> SEQ ID NO 24
<211> LENGTH: 31
<212> TYPE: PRT
<213> ORGANISM: Homo sapiens

<400> SEQUENCE: 24

Met Ala Ala Arg Gly Val Ile Ala Pro Val Gly Glu Ser Leu Arg Tyr
1               5                   10                  15

```
Ala Glu Tyr Leu Gln Pro Ser Ala Lys Arg Pro Asp Ala Asp Val
            20                  25                  30
```

<210> SEQ ID NO 25
<211> LENGTH: 39
<212> TYPE: PRT
<213> ORGANISM: Homo sapiens

<400> SEQUENCE: 25

```
Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Gly Leu Val Arg Ser
        35
```

<210> SEQ ID NO 26
<211> LENGTH: 36
<212> TYPE: PRT
<213> ORGANISM: Homo sapiens

<400> SEQUENCE: 26

```
Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30

Gln Gln Gly Leu
        35
```

<210> SEQ ID NO 27
<211> LENGTH: 32
<212> TYPE: PRT
<213> ORGANISM: Homo sapiens

<400> SEQUENCE: 27

```
Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp Val Asp
            20                  25                  30
```

<210> SEQ ID NO 28
<211> LENGTH: 25
<212> TYPE: PRT
<213> ORGANISM: Homo sapiens

<400> SEQUENCE: 28

```
Met Ala Ala Arg Gly Val Ile Ala Pro Val Gly Glu Ser Leu Arg Tyr
1               5                   10                  15

Ala Glu Tyr Leu Gln Pro Ser Ala Lys
            20                  25
```

<210> SEQ ID NO 29
<211> LENGTH: 30
<212> TYPE: PRT
<213> ORGANISM: Homo sapiens

<400> SEQUENCE: 29

```
Met Ala Ala Arg Gly Val Ile Ala Pro Val Gly Glu Ser Leu Arg Tyr
1               5                   10                  15

Ala Glu Tyr Leu Gln Pro Ser Ala Lys Arg Pro Asp Ala Asp
            20                  25                  30
```

<210> SEQ ID NO 30
<211> LENGTH: 22
<212> TYPE: PRT
<213> ORGANISM: Homo sapiens

<400> SEQUENCE: 30

Met Ala Ala Arg Gly Val Ile Ala Pro Val Gly Glu Ser Leu Arg Tyr
1               5                   10                  15

Ala Glu Tyr Leu Gln Pro
            20

<210> SEQ ID NO 31
<211> LENGTH: 26
<212> TYPE: PRT
<213> ORGANISM: Homo sapiens

<400> SEQUENCE: 31

Met Ala Ala Arg Gly Val Ile Ala Pro Val Gly Glu Ser Leu Arg Tyr
1               5                   10                  15

Ala Glu Tyr Leu Gln Pro Ser Ala Lys Arg
            20                  25

<210> SEQ ID NO 32
<211> LENGTH: 16
<212> TYPE: PRT
<213> ORGANISM: Homo sapiens

<400> SEQUENCE: 32

Gly Val Ile Ala Pro Val Gly Glu Ser Leu Arg Tyr Ala Glu Tyr Leu
1               5                   10                  15

<210> SEQ ID NO 33
<211> LENGTH: 18
<212> TYPE: PRT
<213> ORGANISM: Homo sapiens

<400> SEQUENCE: 33

Ala Arg Gly Val Ile Ala Pro Val Gly Glu Ser Leu Arg Tyr Ala Glu
1               5                   10                  15

Tyr Leu

<210> SEQ ID NO 34
<211> LENGTH: 15
<212> TYPE: PRT
<213> ORGANISM: Homo sapiens

<400> SEQUENCE: 34

Val Ile Ala Pro Val Gly Glu Ser Leu Arg Tyr Ala Glu Tyr Leu
1               5                   10                  15

<210> SEQ ID NO 35
<211> LENGTH: 13
<212> TYPE: PRT
<213> ORGANISM: Homo sapiens

<400> SEQUENCE: 35

Met Ala Ala Arg Gly Val Ile Ala Pro Val Gly Glu Ser
1               5                   10

<210> SEQ ID NO 36
<211> LENGTH: 9
<212> TYPE: PRT

```
<213> ORGANISM: Artificial Sequence
<220> FEATURE:
<223> OTHER INFORMATION: Synthetic Polypeptide

<400> SEQUENCE: 36

Tyr Gly Lys Lys Arg Arg Gln Arg Arg
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 37

Thr Arg Thr Trp Val Pro Lys Gly Leu Lys Ser Pro
1               5                   10

<210> SEQ ID NO 38
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: X is cyclohexylalanine
<220> FEATURE:
<221> NAME/KEY: MOD_RES
<222> LOCATION: (3)..(3)
<223> OTHER INFORMATION: X is cyclohexylalanine
<220> FEATURE:
<221> NAME/KEY: MOD_RES
<222> LOCATION: (3)..(3)
<223> OTHER INFORMATION: X is cyclohexylalanine
<220> FEATURE:
<221> NAME/KEY: MOD_RES
<222> LOCATION: (5)..(5)
<223> OTHER INFORMATION: X is cyclohexylalanine
<220> FEATURE:
<221> NAME/KEY: MOD_RES
<222> LOCATION: (7)..(7)
<223> OTHER INFORMATION: X is cyclohexylalanine

<400> SEQUENCE: 38

Xaa Arg Xaa Lys Xaa Arg Xaa Lys Met Ala Ala Arg Gly Val Ile Ala
1               5                   10                  15

Pro Val Gly Glu Ser Leu Arg Tyr Ala Glu Tyr Leu
            20                  25

<210> SEQ ID NO 39
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: X is cyclohexylalanine
<220> FEATURE:
<221> NAME/KEY: MOD_RES
<222> LOCATION: (3)..(3)
<223> OTHER INFORMATION: X is cyclohexylalanine
<220> FEATURE:
<221> NAME/KEY: MOD_RES
<222> LOCATION: (5)..(5)
<223> OTHER INFORMATION: X is cyclohexylalanine
<220> FEATURE:
<221> NAME/KEY: MOD_RES
```

```
<222> LOCATION: (7)..(7)
<223> OTHER INFORMATION: X is cyclohexylalanine

<400> SEQUENCE: 39

Xaa Arg Xaa Lys Xaa Arg Xaa Lys
1               5
```